(12) United States Patent
Lofgren et al.

(10) Patent No.: US 11,495,334 B2
(45) Date of Patent: Nov. 8, 2022

(54) MEDICAL DEVICE SYSTEM AND METHOD HAVING A DISTRIBUTED DATABASE

(71) Applicant: GAMBRO LUNDIA AB, Lund (SE)

(72) Inventors: Par Lofgren, Lund (SE); Sture Hobro, Lund (SE); Roger Nilsson, Hoor (SE); Roland Persson, Limhamn (SE); Peter Ridell, Sodra Sandby (SE)

(73) Assignee: Gambro Lundia AB, Lund (SE)

( * ) Notice: Subject to any disclaimer, the term of this patent is extended or adjusted under 35 U.S.C. 154(b) by 574 days.

(21) Appl. No.: 15/571,965

(22) PCT Filed: Jun. 22, 2016

(86) PCT No.: PCT/EP2016/064392
§ 371 (c)(1),
(2) Date: Nov. 6, 2017

(87) PCT Pub. No.: WO2016/207206
PCT Pub. Date: Dec. 29, 2016

(65) Prior Publication Data
US 2018/0144817 A1 May 24, 2018

(30) Foreign Application Priority Data
Jun. 25, 2015 (SE) .................................. 1550885-6

(51) Int. Cl.
*G16H 10/60* (2018.01)
*G06F 16/182* (2019.01)
(Continued)

(52) U.S. Cl.
CPC .............. *G16H 10/60* (2018.01); *A61M 5/14* (2013.01); *G06F 11/0709* (2013.01);
(Continued)

(58) Field of Classification Search
CPC ........ G16H 10/60; G16H 15/00; G16H 20/17; G06F 11/0709; G06F 16/182; G06F 19/3418; G06F 19/3468; A61M 5/14
See application file for complete search history.

(56) References Cited

U.S. PATENT DOCUMENTS

| 250,868 A | 12/1881 | Abbott |
| 927,476 A | 7/1909 | Barker |

(Continued)

FOREIGN PATENT DOCUMENTS

| CH | 296007 | 1/1954 |
| DE | 1806654 | 5/1970 |

(Continued)

OTHER PUBLICATIONS

Notice of Reasons for Rejection dated Dec. 5, 2017 in corresponding JP Application No. 2013-257132.
(Continued)

*Primary Examiner* — Evangeline Barr
*Assistant Examiner* — Anthony Balaj
(74) *Attorney, Agent, or Firm* — K&L Gates LLP

(57) ABSTRACT

A medical device system (10) including a distributed database (10a to 10f); a plurality of medical devices (12) operating with the distributed database (10a to 10f); and a logic implementer (20) associated with each medical device (12), wherein each logic implementer (20) is programmed to access the distributed database (10a to 10f), so that each medical device (12) of system (10) periodically (i) delivers at least one of prescription input parameters or treatment output data to and (ii) retrieves at least one of prescription input parameters or treatment output data from each of the other medical devices (12).

32 Claims, 19 Drawing Sheets

(51) Int. Cl.
  *A61M 5/14* (2006.01)
  *G16H 20/40* (2018.01)
  *G16H 40/40* (2018.01)
  *G16H 20/17* (2018.01)
  *G16H 15/00* (2018.01)
  *G06F 11/07* (2006.01)

(52) U.S. Cl.
  CPC .......... *G06F 16/182* (2019.01); *G16H 15/00* (2018.01); *G16H 20/17* (2018.01); *G16H 20/40* (2018.01); *G16H 40/40* (2018.01)

(56) References Cited

U.S. PATENT DOCUMENTS

| | | |
|---|---|---|
| 1,505,050 A | 8/1924 | Lauritsen |
| 2,292,007 A | 8/1942 | Morgan |
| 2,529,028 A | 7/1947 | Landon |
| 2,122,509 A | 7/1948 | Beliaeff |
| 2,736,332 A | 2/1956 | Simmons |
| 3,044,236 A | 7/1962 | Bearden et al. |
| 3,074,645 A | 1/1963 | Main |
| 3,095,062 A | 6/1963 | Neely |
| 3,229,445 A | 1/1966 | Kraft |
| 3,287,031 A | 11/1966 | Simmons et al. |
| 3,287,885 A | 11/1966 | Sommer |
| 3,295,297 A | 1/1967 | Collins |
| 3,332,737 A | 7/1967 | Krause |
| 3,342,019 A | 9/1967 | Smythe |
| 3,388,803 A | 6/1968 | Scott |
| 3,412,760 A | 11/1968 | Franck |
| 3,426,150 A | 2/1969 | Tygart |
| 3,463,728 A | 8/1969 | Kolobow et al. |
| 3,485,245 A | 12/1969 | Lahr et al. |
| 3,490,479 A | 1/1970 | Mott et al. |
| 3,527,572 A | 9/1970 | Urkiewicz |
| 3,528,550 A | 9/1970 | Cappelen, Jr. |
| 3,540,477 A | 11/1970 | Hogel |
| 3,545,438 A | 12/1970 | De Vries |
| 3,563,381 A | 2/1971 | Edelson et al. |
| 3,581,464 A | 6/1971 | Bhuta et al. |
| 3,598,727 A | 8/1971 | Wilock |
| 3,608,729 A | 9/1971 | Haselden |
| 3,617,545 A | 11/1971 | Dabois et al. |
| 3,619,423 A | 11/1971 | Galletti et al. |
| 3,667,612 A | 6/1972 | Leonard |
| 3,669,878 A | 6/1972 | Marantz et al. |
| 3,669,880 A | 6/1972 | Marantz et al. |
| 3,677,710 A | 7/1972 | Hirsch |
| 3,682,817 A | 8/1972 | Marx |
| 3,685,680 A | 8/1972 | Tenckhoff et al. |
| 3,697,418 A | 10/1972 | Johnson |
| 3,703,959 A | 11/1972 | Raymond |
| 3,707,967 A | 1/1973 | Kitrilakis et al. |
| 3,727,612 A | 4/1973 | Sayers et al. |
| 3,730,183 A | 5/1973 | Goldsmith et al. |
| 3,739,943 A | 6/1973 | Williamsen et al. |
| 3,742,938 A | 7/1973 | Stern |
| 3,744,492 A | 7/1973 | Leibinsohn |
| 3,744,636 A | 7/1973 | Commarmot |
| 3,756,234 A | 9/1973 | Kopp |
| 3,756,752 A | 9/1973 | Stenner |
| 3,769,207 A | 10/1973 | Baer |
| 3,771,288 A | 11/1973 | Wisman et al. |
| 3,774,762 A | 11/1973 | Lichtenstein |
| 3,786,190 A | 1/1974 | Pori |
| 3,795,088 A | 3/1974 | Esmond |
| 3,799,873 A | 3/1974 | Brown |
| 3,809,241 A | 5/1974 | Alvine |
| 3,809,871 A | 5/1974 | Howard et al. |
| 3,810,102 A | 5/1974 | Parks, III et al. |
| 3,814,249 A | 6/1974 | Eaton |
| 3,825,493 A | 7/1974 | Brown et al. |
| 3,827,561 A | 8/1974 | Serfass et al. |
| 3,827,975 A | 8/1974 | Bizot et al. |
| 3,830,234 A | 8/1974 | Kopp |
| 3,834,386 A | 9/1974 | Sisley |
| 3,848,112 A | 11/1974 | Weichselbaum et al. |
| 3,849,071 A | 11/1974 | Kayser |
| 3,850,835 A | 11/1974 | Marantz et al. |
| 3,858,574 A | 1/1975 | Page |
| 3,878,095 A | 4/1975 | Frasier et al. |
| 3,878,564 A | 4/1975 | Yao et al. |
| 3,884,808 A | 5/1975 | Scott |
| 3,908,653 A | 9/1975 | Kettering |
| 3,910,257 A | 10/1975 | Fletcher et al. |
| 3,910,260 A | 10/1975 | Sarnoff et al. |
| 3,911,915 A | 10/1975 | Seifter et al. |
| 3,915,802 A | 10/1975 | Kominek |
| 3,921,196 A | 11/1975 | Patterson |
| 3,926,797 A | 12/1975 | Gigou et al. |
| 3,939,069 A | 2/1976 | Granger et al. |
| 3,946,731 A | 3/1976 | Lichtenstein |
| 3,964,479 A | 6/1976 | Boag et al. |
| 3,971,000 A | 7/1976 | Cromwell |
| 3,976,311 A | 8/1976 | Spendlove |
| 3,979,284 A | 9/1976 | Granger et al. |
| 3,985,134 A | 10/1976 | Lissot et al. |
| 3,989,622 A | 11/1976 | Marantz et al. |
| 3,996,027 A | 12/1976 | Schnell et al. |
| 3,998,103 A | 12/1976 | Bjorklund et al. |
| 4,000,072 A | 12/1976 | Sato et al. |
| 4,031,010 A | 6/1977 | Nose |
| 4,031,891 A | 6/1977 | Jess |
| 4,032,908 A | 6/1977 | Rice et al. |
| 4,036,747 A | 7/1977 | Hori et al. |
| 4,038,190 A | 7/1977 | Baudet et al. |
| 4,047,563 A | 9/1977 | Kurata |
| 4,048,995 A | 9/1977 | Mittleman |
| 4,054,522 A | 10/1977 | Pinkerton |
| 4,060,485 A | 11/1977 | Eaton |
| 4,061,031 A | 12/1977 | Grimsrud |
| 4,067,803 A | 1/1978 | Quentin |
| 4,078,562 A | 3/1978 | Friedman |
| 4,081,372 A | 3/1978 | Atkin et al. |
| 4,102,655 A | 7/1978 | Jeffery et al. |
| 4,115,259 A | 9/1978 | Bigi |
| 4,118,314 A | 10/1978 | Yoshida |
| 4,137,160 A | 1/1979 | Ebling et al. |
| 4,144,496 A | 3/1979 | Cunningham et al. |
| 4,149,860 A | 4/1979 | Kulik |
| 4,151,088 A | 4/1979 | Wolf, Jr. et al. |
| 4,151,407 A | 4/1979 | McBride et al. |
| 4,156,867 A | 5/1979 | Bench et al. |
| 4,164,320 A | 8/1979 | Irazoqui et al. |
| 4,173,537 A | 11/1979 | Newhart et al. |
| 4,173,971 A | 11/1979 | Karz |
| 4,180,460 A | 12/1979 | Calari |
| 4,181,245 A | 1/1980 | Garrett et al. |
| 4,190,047 A | 2/1980 | Jacobsen et al. |
| 4,191,182 A | 3/1980 | Popovich et al. |
| 4,191,646 A | 3/1980 | Larsson et al. |
| 4,192,748 A | 3/1980 | Hyden |
| 4,194,536 A | 3/1980 | Stine et al. |
| 4,199,307 A | 4/1980 | Jassawalla |
| 4,200,095 A | 4/1980 | Reti |
| 4,209,402 A | 6/1980 | Gentles |
| 4,212,738 A | 7/1980 | Henne |
| 4,213,859 A | 7/1980 | Smakman et al. |
| 4,229,299 A | 10/1980 | Savitz et al. |
| 4,240,408 A | 12/1980 | Schael |
| 4,244,816 A | 1/1981 | Vogler et al. |
| 4,247,393 A | 1/1981 | Wallace |
| 4,256,718 A | 3/1981 | McArthur et al. |
| 4,263,647 A | 4/1981 | Merrell et al. |
| 4,267,040 A | 5/1981 | Schal |
| 4,267,047 A | 5/1981 | Henne et al. |
| 4,269,708 A | 5/1981 | Bounomini et al. |
| 4,270,532 A | 6/1981 | Franetzki et al. |
| 4,273,121 A | 6/1981 | Jassawalla |
| 4,276,175 A | 6/1981 | Bower |
| 4,282,872 A | 8/1981 | Franetzki et al. |
| 4,293,413 A | 10/1981 | Schnell |
| 4,293,762 A | 10/1981 | Ogawa |
| 4,303,376 A | 12/1981 | Siekmann |

(56) References Cited

U.S. PATENT DOCUMENTS

| | | |
|---|---|---|
| 4,303,521 A | 12/1981 | Lehmann |
| 4,304,670 A | 12/1981 | Watanabe et al. |
| 4,308,866 A | 1/1982 | Jelliffe et al. |
| 4,311,137 A | 1/1982 | Gerard |
| 4,313,831 A | 2/1982 | Lehmann et al. |
| 4,319,338 A | 3/1982 | Grudowski et al. |
| 4,320,757 A | 3/1982 | Whitney et al. |
| 4,325,715 A | 4/1982 | Bowman et al. |
| 4,332,264 A | 6/1982 | Gortz et al. |
| 4,338,190 A | 7/1982 | Kraus et al. |
| 4,344,777 A | 8/1982 | Siposs |
| 4,345,919 A | 8/1982 | Wilkinson et al. |
| 4,345,999 A | 8/1982 | Sigdell et al. |
| 4,348,280 A | 9/1982 | George et al. |
| 4,353,368 A | 10/1982 | Slovak et al. |
| 4,354,252 A | 10/1982 | Lamb et al. |
| 4,360,323 A | 11/1982 | Anderson |
| 4,360,507 A | 11/1982 | McArthur et al. |
| 4,363,641 A | 12/1982 | Finn, III |
| 4,364,747 A | 12/1982 | Blackshear et al. |
| 4,368,118 A | 1/1983 | Siposs |
| 4,369,780 A | 1/1983 | Sakai |
| 4,370,983 A | 2/1983 | Lichtenstein |
| 4,373,527 A | 2/1983 | Fischell |
| 4,381,003 A | 4/1983 | Buoncristiani |
| 4,381,776 A | 5/1983 | Latham, Jr. |
| 4,385,630 A | 5/1983 | Gilcher et al. |
| 4,386,634 A | 6/1983 | Stasz et al. |
| 4,398,289 A | 8/1983 | Schoute |
| 4,398,908 A | 8/1983 | Siposs |
| 4,416,654 A | 11/1983 | Schoendorfer et al. |
| 4,425,114 A | 1/1984 | Schoendorfer et al. |
| 4,427,009 A | 1/1984 | Wells et al. |
| 4,428,381 A | 1/1984 | Hepp |
| 4,433,971 A | 2/1984 | Lindsay et al. |
| 4,443,216 A | 4/1984 | Chappell |
| 4,445,174 A | 4/1984 | Fletcher |
| 4,447,224 A | 5/1984 | DeCant, Jr. et al. |
| 4,449,538 A | 5/1984 | Corbitt et al. |
| 4,451,255 A | 5/1984 | Bujan et al. |
| 4,457,750 A | 7/1984 | Hill |
| 4,458,693 A | 7/1984 | Badzinski et al. |
| 4,460,358 A | 7/1984 | Somerville et al. |
| 4,460,555 A | 7/1984 | Thompson |
| 4,464,172 A | 8/1984 | Lichtenstein |
| 4,464,563 A | 8/1984 | Jewett |
| 4,469,481 A | 9/1984 | Kobayashi |
| 4,473,449 A | 9/1984 | Michaels et al. |
| 4,475,901 A | 10/1984 | Kraegen et al. |
| 4,476,381 A | 10/1984 | Rubin |
| 4,477,342 A | 10/1984 | Allan et al. |
| 4,480,751 A | 11/1984 | Lueptow |
| 4,481,670 A | 11/1984 | Freeburg |
| 4,487,604 A | 12/1984 | Iwatschenko et al. |
| 4,490,798 A | 12/1984 | Franks et al. |
| 4,493,705 A | 1/1985 | Gordon et al. |
| 4,496,351 A | 1/1985 | Hillel et al. |
| 4,498,900 A | 2/1985 | Buoncristiani |
| 4,511,352 A | 4/1985 | Theeuwes et al. |
| 4,512,163 A | 4/1985 | Wells et al. |
| 4,525,861 A | 6/1985 | Freeburg |
| 4,529,401 A | 7/1985 | Leslie et al. |
| 4,531,527 A | 7/1985 | Reinhold, Jr. et al. |
| 4,531,937 A | 7/1985 | Yates |
| 4,532,414 A | 7/1985 | Shah et al. |
| 4,538,138 A | 8/1985 | Harvey et al. |
| 4,542,015 A | 9/1985 | Smakman et al. |
| 4,545,071 A | 10/1985 | Freeburg |
| 4,551,133 A | 11/1985 | Zegers de Beyl et al. |
| 4,559,038 A | 12/1985 | Berg et al. |
| 4,560,472 A | 12/1985 | Granzow et al. |
| 4,560,979 A | 12/1985 | Rosskopf |
| 4,561,443 A | 12/1985 | Hogrefe et al. |
| 4,562,751 A | 1/1986 | Nason |
| 4,568,333 A | 2/1986 | Sawyer et al. |
| 4,574,283 A | 3/1986 | Arakawa et al. |
| 4,581,141 A | 4/1986 | Ash |
| 4,583,981 A | 4/1986 | Urquhart et al. |
| 4,586,920 A | 5/1986 | Peabody |
| 4,586,925 A | 5/1986 | Carlsson et al. |
| 4,590,473 A | 5/1986 | Burke et al. |
| 4,602,249 A | 7/1986 | Abbott |
| 4,618,343 A | 10/1986 | Polaschegg |
| 4,619,653 A | 10/1986 | Fischell |
| 4,622,032 A | 11/1986 | Katsura et al. |
| 4,622,979 A | 11/1986 | Katchis et al. |
| 4,624,661 A | 11/1986 | Arimond |
| RE32,303 E | 12/1986 | Lasker et al. |
| 4,636,950 A | 1/1987 | Caswell et al. |
| 4,637,817 A | 1/1987 | Archibald et al. |
| 4,643,713 A | 2/1987 | Viitala |
| 4,643,715 A | 2/1987 | Isono et al. |
| 4,650,458 A | 3/1987 | Dahlberg et al. |
| 4,650,464 A | 3/1987 | Ruiz et al. |
| 4,650,469 A | 3/1987 | Berg et al. |
| 4,650,857 A | 3/1987 | May |
| 4,652,262 A | 3/1987 | Veracchi |
| 4,655,941 A | 4/1987 | Suzuki |
| 4,657,490 A | 4/1987 | Abbott |
| 4,661,246 A | 4/1987 | Ash |
| 4,664,891 A | 5/1987 | Cosentino et al. |
| 4,666,598 A | 5/1987 | Heath et al. |
| 4,670,007 A | 6/1987 | Wheeldon et al. |
| 4,676,776 A | 6/1987 | Howson |
| 4,678,460 A | 7/1987 | Rosner |
| 4,680,445 A | 7/1987 | Ogawa |
| 4,681,563 A | 7/1987 | Deckert et al. |
| 4,681,606 A | 7/1987 | Swan, Jr. et al. |
| 4,684,460 A | 8/1987 | Issautier |
| 4,688,167 A | 8/1987 | Agarwal |
| 4,691,580 A | 9/1987 | Fosslien |
| 4,695,944 A | 9/1987 | Zandveld et al. |
| 4,695,954 A | 9/1987 | Rose et al. |
| 4,696,671 A | 9/1987 | Epstein et al. |
| 4,697,928 A | 10/1987 | Csongor |
| 4,702,595 A | 10/1987 | Mutschler et al. |
| 4,702,829 A | 10/1987 | Polaschegg et al. |
| 4,703,913 A | 11/1987 | Hunkapiller |
| 4,705,506 A | 11/1987 | Archibald |
| 4,707,778 A | 11/1987 | Yamada et al. |
| 4,708,802 A | 11/1987 | Rath et al. |
| 4,714,462 A | 12/1987 | DiComenico |
| 4,717,042 A | 1/1988 | McLaughlin |
| 4,718,576 A | 1/1988 | Tamura et al. |
| 4,718,890 A | 1/1988 | Peabody |
| 4,722,224 A | 2/1988 | Scheller et al. |
| 4,722,349 A | 2/1988 | Baumberg |
| 4,722,725 A | 2/1988 | Sawyer et al. |
| 4,722,731 A | 2/1988 | Vailancourt |
| 4,722,734 A | 2/1988 | Kolln |
| 4,725,694 A | 2/1988 | Auer et al. |
| 4,730,849 A | 3/1988 | Siegel |
| 4,731,058 A | 3/1988 | Doan |
| 4,731,731 A | 3/1988 | Cochran |
| 4,732,411 A | 3/1988 | Siegel |
| 4,734,198 A | 3/1988 | Harm et al. |
| 4,734,269 A | 3/1988 | Clarke et al. |
| 4,735,609 A | 4/1988 | Comeau et al. |
| 4,741,732 A | 5/1988 | Crankshaw et al. |
| 4,741,736 A | 5/1988 | Brown |
| 4,747,822 A | 5/1988 | Peabody |
| 4,756,706 A | 7/1988 | Kerns et al. |
| 4,759,756 A | 7/1988 | Forman et al. |
| 4,765,907 A | 8/1988 | Scott |
| 4,767,399 A | 8/1988 | Bollish |
| 4,769,151 A | 9/1988 | Shouldice |
| 4,778,449 A | 10/1988 | Weber et al. |
| 4,778,451 A | 10/1988 | Kamen |
| 4,779,626 A | 10/1988 | Peel et al. |
| 4,784,645 A | 11/1988 | Fischell |
| 4,785,799 A | 11/1988 | Schoon et al. |
| 4,785,969 A | 11/1988 | McLaughlin |
| 4,796,634 A | 1/1989 | Huntsman et al. |
| 4,796,644 A | 1/1989 | Polaschegg |

(56) References Cited

U.S. PATENT DOCUMENTS

| | | |
|---|---|---|
| 4,797,840 A | 1/1989 | Fraden |
| 4,803,625 A | 2/1989 | Fu et al. |
| 4,804,474 A | 2/1989 | Blum |
| 4,806,135 A | 2/1989 | Siposs |
| 4,810,090 A | 3/1989 | Boucher |
| 4,810,243 A | 3/1989 | Howson |
| 4,811,844 A | 3/1989 | Moulding, Jr. et al. |
| 4,816,208 A | 3/1989 | Woods et al. |
| 4,817,044 A | 3/1989 | Ogren |
| 4,823,256 A | 4/1989 | Bishop et al. |
| 4,828,543 A | 5/1989 | Weiss et al. |
| 4,828,545 A | 5/1989 | Epstein et al. |
| 4,830,018 A | 5/1989 | Treach |
| 4,831,562 A | 5/1989 | McIntosh et al. |
| 4,832,033 A | 5/1989 | Maher et al. |
| 4,835,372 A | 5/1989 | Beard et al. |
| 4,835,521 A | 5/1989 | Andrejasich et al. |
| 4,838,275 A | 6/1989 | Lee |
| 4,838,865 A | 6/1989 | Flank et al. |
| 4,839,806 A | 6/1989 | Goldfischer et al. |
| 4,844,074 A | 7/1989 | Kurucz |
| 4,845,644 A | 7/1989 | Anthias et al. |
| 4,847,470 A | 7/1989 | Bakke |
| 4,847,764 A | 7/1989 | Halvorson |
| 4,850,009 A | 7/1989 | Zook et al. |
| 4,850,972 A | 7/1989 | Schulman et al. |
| 4,853,521 A | 8/1989 | Claeys et al. |
| 4,854,324 A | 8/1989 | Hirschman et al. |
| 4,857,713 A | 8/1989 | Brown |
| 4,857,716 A | 8/1989 | Gombrich et al. |
| 4,865,584 A | 9/1989 | Epstein et al. |
| 4,871,351 A | 10/1989 | Feingold |
| 4,878,175 A | 10/1989 | Norden-Paul et al. |
| 4,889,132 A | 12/1989 | Hutcheson et al. |
| 4,889,134 A | 12/1989 | Greenwold et al. |
| 4,893,270 A | 1/1990 | Beck et al. |
| 4,897,777 A | 1/1990 | Janke et al. |
| 4,897,784 A | 1/1990 | Nay |
| 4,898,576 A | 2/1990 | Philip |
| 4,898,578 A | 2/1990 | Rubalcaba, Jr. |
| 4,901,728 A | 2/1990 | Hutchison |
| 4,906,816 A | 3/1990 | van Leerdam |
| 4,908,017 A | 3/1990 | Howson et al. |
| 4,912,623 A | 3/1990 | Rantala et al. |
| 4,916,441 A | 4/1990 | Gombrich et al. |
| 4,922,922 A | 5/1990 | Pollock et al. |
| 4,923,612 A | 5/1990 | Trivett et al. |
| 4,925,444 A | 5/1990 | Orkin et al. |
| 4,932,987 A | 6/1990 | Molina |
| 4,933,843 A | 6/1990 | Scheller et al. |
| 4,937,777 A | 6/1990 | Flood et al. |
| 4,941,808 A | 7/1990 | Qureshi et al. |
| 4,941,875 A | 7/1990 | Brennan |
| 4,943,279 A | 7/1990 | Samiotes et al. |
| 4,946,439 A | 8/1990 | Eggers |
| 4,949,274 A | 8/1990 | Hollander et al. |
| 4,950,259 A | 8/1990 | Geary et al. |
| 4,952,928 A | 8/1990 | Carroll et al. |
| 4,953,074 A | 8/1990 | Kametani et al. |
| 4,955,508 A | 9/1990 | Capanna et al. |
| D311,061 S | 10/1990 | Vrana et al. |
| 4,960,230 A | 10/1990 | Marelli |
| 4,966,579 A | 10/1990 | Polaschegg |
| 4,967,928 A | 11/1990 | Carter |
| 4,968,295 A | 11/1990 | Neumann |
| 4,976,683 A | 12/1990 | Gauthier et al. |
| 4,976,685 A | 12/1990 | Block, Jr. |
| 4,977,590 A | 12/1990 | Milovancevic |
| 4,978,335 A | 12/1990 | Arthur |
| 4,990,258 A | 2/1991 | Bjare et al. |
| 4,991,091 A | 2/1991 | Allen |
| 4,992,926 A | 2/1991 | Janke et al. |
| 4,993,068 A | 2/1991 | Piosenka et al. |
| 4,997,464 A | 3/1991 | Kopf |
| 4,998,249 A | 3/1991 | Bennett et al. |
| 5,002,055 A | 3/1991 | Merki et al. |
| 5,002,471 A | 3/1991 | Perlov |
| 5,003,296 A | 3/1991 | Lee |
| 5,004,459 A | 4/1991 | Peabody et al. |
| 5,006,699 A | 4/1991 | Felkner et al. |
| 5,007,429 A | 4/1991 | Treatch et al. |
| 5,011,607 A | 4/1991 | Shinzato |
| 5,012,402 A | 4/1991 | Akiyama |
| 5,012,411 A | 4/1991 | Policastro et al. |
| 5,014,875 A | 5/1991 | McLaughlin et al. |
| 5,016,172 A | 5/1991 | Dessertine |
| 5,023,770 A | 6/1991 | Siverling |
| 5,025,374 A | 6/1991 | Roizen et al. |
| 5,032,265 A | 7/1991 | Jha et al. |
| 5,036,852 A | 8/1991 | Leishman |
| 5,038,800 A | 8/1991 | Oba |
| 5,041,086 A | 8/1991 | Koenig et al. |
| 5,045,048 A | 9/1991 | Kaleskas et al. |
| 5,047,147 A | 9/1991 | Chevallet et al. |
| 5,047,959 A | 9/1991 | Phillips et al. |
| 5,049,492 A | 9/1991 | Sauer et al. |
| 5,053,031 A | 10/1991 | Borsanyi |
| 5,053,684 A | 10/1991 | Nooyan |
| 5,053,990 A | 10/1991 | Kreifels et al. |
| 5,055,001 A | 10/1991 | Natwick et al. |
| 5,057,076 A | 10/1991 | Polaschegg |
| 5,059,173 A | 10/1991 | Sacco |
| 5,061,236 A | 10/1991 | Sutherland et al. |
| 5,061,243 A | 10/1991 | Winchell et al. |
| 5,061,365 A | 10/1991 | Utterberg |
| 5,062,774 A | 11/1991 | Kramer et al. |
| 5,072,356 A | 12/1991 | Watt et al. |
| 5,072,383 A | 12/1991 | Brimm et al. |
| 5,072,412 A | 12/1991 | Henderson, Jr. et al. |
| 5,073,167 A | 12/1991 | Carr et al. |
| 5,078,683 A | 1/1992 | Sancoff et al. |
| 5,084,828 A | 1/1992 | Kaufman et al. |
| 5,087,245 A | 2/1992 | Doan |
| 5,088,515 A | 2/1992 | Kamen |
| 5,088,904 A | 2/1992 | Okada |
| 5,088,981 A | 2/1992 | Howson et al. |
| 5,088,990 A | 2/1992 | Hivale et al. |
| 5,091,094 A | 2/1992 | Veech |
| 5,096,385 A | 3/1992 | Georgi et al. |
| 5,098,377 A | 3/1992 | Borsanyi et al. |
| 5,100,380 A | 3/1992 | Adaniya et al. |
| 5,104,374 A | 4/1992 | Bishko et al. |
| 5,108,363 A | 4/1992 | Tuttle et al. |
| 5,108,367 A | 4/1992 | Epstein et al. |
| 5,108,372 A | 4/1992 | Swenson |
| 5,109,487 A | 4/1992 | Ohgomori et al. |
| 5,109,849 A | 5/1992 | Goodman et al. |
| 5,112,319 A | 5/1992 | Lai |
| 5,112,480 A | 5/1992 | Hukasawa |
| 5,114,580 A | 5/1992 | Ahmad et al. |
| 5,116,203 A | 5/1992 | Natwick et al. |
| 5,116,312 A | 5/1992 | Blankenship et al. |
| 5,120,303 A | 6/1992 | Hombrouckx |
| 5,122,516 A | 6/1992 | Watanabe et al. |
| 5,125,069 A | 6/1992 | O'Boyle |
| 5,131,092 A | 7/1992 | Sackmann et al. |
| 5,134,574 A | 7/1992 | Beaverstock et al. |
| 5,135,500 A | 8/1992 | Zdeb |
| 5,137,023 A | 8/1992 | Mendelson et al. |
| 5,141,492 A | 8/1992 | Dadson et al. |
| 5,141,493 A | 8/1992 | Jacobsen et al. |
| 5,151,978 A | 9/1992 | Bronikowski et al. |
| 5,152,296 A | 10/1992 | Simons |
| 5,153,416 A | 10/1992 | Neeley |
| 5,153,827 A | 10/1992 | Coutre et al. |
| 5,155,693 A | 10/1992 | Altmayer et al. |
| 5,157,595 A | 10/1992 | Lovrenich |
| 5,158,091 A | 10/1992 | Butterfield et al. |
| 5,159,673 A | 10/1992 | Sackmann et al. |
| 5,160,320 A | 11/1992 | Yum et al. |
| 5,161,211 A | 11/1992 | Taguchi et al. |
| 5,167,235 A | 12/1992 | Seacord et al. |
| 5,167,921 A | 12/1992 | Gordon |
| 5,172,698 A | 12/1992 | Stanko |

(56) References Cited

U.S. PATENT DOCUMENTS

| | | |
|---|---|---|
| 5,173,125 A | 12/1992 | Felding |
| 5,176,004 A | 1/1993 | Gaudet |
| 5,178,763 A | 1/1993 | Delaunay |
| 5,179,569 A | 1/1993 | Sawyer |
| 5,179,700 A | 1/1993 | Aihara et al. |
| 5,180,896 A | 1/1993 | Gibby et al. |
| 5,181,910 A | 1/1993 | Scanlon |
| 5,186,609 A | 2/1993 | Inoue et al. |
| 5,190,185 A | 3/1993 | Blechl |
| 5,190,522 A | 3/1993 | Wojcicki et al. |
| 5,191,891 A | 3/1993 | Righter |
| 5,204,000 A | 4/1993 | Steadman et al. |
| 5,208,907 A | 5/1993 | Shelton et al. |
| 5,211,849 A | 5/1993 | Kitaevich et al. |
| 5,213,099 A | 5/1993 | Tripp, Jr. |
| 5,213,232 A | 5/1993 | Kraft et al. |
| 5,213,568 A | 5/1993 | Lattin et al. |
| 5,219,330 A | 6/1993 | Bollish et al. |
| 5,219,331 A | 6/1993 | Vanderveen |
| 5,221,267 A | 6/1993 | Folden |
| 5,225,974 A | 7/1993 | Mathews et al. |
| 5,226,425 A | 7/1993 | Righter |
| 5,228,450 A | 7/1993 | Sellers |
| 5,228,889 A | 7/1993 | Cortial et al. |
| 5,231,990 A | 8/1993 | Gauglitz |
| 5,234,404 A | 8/1993 | Tuttle et al. |
| 5,235,510 A | 8/1993 | Yamada et al. |
| 5,236,416 A | 8/1993 | McDaniel et al. |
| 5,236,476 A | 8/1993 | Klick |
| 5,238,001 A | 8/1993 | Gallant et al. |
| 5,240,007 A | 8/1993 | Pytel et al. |
| 5,244,463 A | 9/1993 | Cordner, Jr. et al. |
| 5,245,693 A | 9/1993 | Ford et al. |
| 5,245,704 A | 9/1993 | Weber et al. |
| 5,246,560 A | 9/1993 | Nekoksa et al. |
| 5,254,096 A | 10/1993 | Rondelet et al. |
| 5,256,156 A | 10/1993 | Kern et al. |
| 5,256,157 A | 10/1993 | Samiotes et al. |
| 5,256,371 A | 10/1993 | Pippert |
| 5,259,954 A | 11/1993 | Taylor |
| 5,259,961 A | 11/1993 | Eigendorf |
| 5,265,010 A | 11/1993 | Evans-Paganelli et al. |
| 5,265,431 A | 11/1993 | Gaudet et al. |
| 5,267,174 A | 11/1993 | Kaufman et al. |
| 5,268,077 A | 12/1993 | Bubik et al. |
| 5,271,405 A | 12/1993 | Boyer et al. |
| 5,272,318 A | 12/1993 | Gorman |
| 5,272,321 A | 12/1993 | Otsuka et al. |
| 5,273,517 A | 12/1993 | Barone et al. |
| 5,274,434 A | 12/1993 | Morioka et al. |
| 5,276,611 A | 1/1994 | Ghiraldi |
| 5,277,188 A | 1/1994 | Selker |
| 5,277,820 A | 1/1994 | Ash |
| 5,283,861 A | 2/1994 | Dangler et al. |
| 5,284,150 A | 2/1994 | Butterfield et al. |
| 5,284,470 A | 2/1994 | Beltz |
| 5,286,252 A | 2/1994 | Tuttle et al. |
| 5,292,029 A | 3/1994 | Pearson |
| 5,295,505 A | 3/1994 | Polaschegg et al. |
| 5,297,257 A | 3/1994 | Struger et al. |
| 5,298,021 A | 3/1994 | Sherer |
| 5,304,126 A | 4/1994 | Epstein et al. |
| 5,307,263 A | 4/1994 | Brown |
| 5,307,372 A | 4/1994 | Sawyer et al. |
| 5,307,463 A | 4/1994 | Hyatt et al. |
| 5,311,908 A | 5/1994 | Barone et al. |
| 5,314,243 A | 5/1994 | McDonald et al. |
| 5,315,505 A | 5/1994 | Pratt et al. |
| 5,317,506 A | 5/1994 | Coutre et al. |
| 5,318,750 A | 6/1994 | Lascombes |
| 5,319,363 A | 6/1994 | Welch et al. |
| 5,319,543 A | 6/1994 | Wilhelm |
| 5,321,618 A | 6/1994 | Gessman |
| 5,321,829 A | 6/1994 | Zifferer |
| 5,325,478 A | 6/1994 | Shelton et al. |
| 5,326,473 A | 7/1994 | Lascombes et al. |
| 5,326,476 A | 7/1994 | Grogan et al. |
| 5,327,341 A | 7/1994 | Whalen et al. |
| 5,330,420 A | 7/1994 | Lee |
| 5,331,549 A | 7/1994 | Crawford, Jr. |
| 5,336,165 A | 8/1994 | Twardowski |
| 5,336,173 A | 8/1994 | Folden |
| 5,336,245 A | 8/1994 | Adams et al. |
| 5,337,230 A | 8/1994 | Baumgartner et al. |
| 5,338,157 A | 8/1994 | Blomquist |
| 5,338,293 A | 8/1994 | Jeppsson et al. |
| 5,339,821 A | 8/1994 | Fujimoto |
| 5,341,291 A | 8/1994 | Roizen et al. |
| 5,341,412 A | 8/1994 | Ramot et al. |
| D350,822 S | 9/1994 | Lanigan |
| D350,823 S | 9/1994 | Lanigan |
| 5,348,008 A | 9/1994 | Bornn et al. |
| 5,348,539 A | 9/1994 | Herskowitz |
| 5,349,675 A | 9/1994 | Fitzgerald et al. |
| 5,350,357 A | 9/1994 | Kamen et al. |
| 5,356,376 A | 10/1994 | Milijasevic et al. |
| 5,356,378 A | 10/1994 | Doan |
| 5,358,481 A | 10/1994 | Todd et al. |
| 5,361,202 A | 11/1994 | Doue |
| 5,361,758 A | 11/1994 | Hall et al. |
| 5,366,630 A | 11/1994 | Chevallet |
| 5,366,896 A | 11/1994 | Margrey et al. |
| 5,366,904 A | 11/1994 | Qureshi et al. |
| 5,367,555 A | 11/1994 | Isoyama |
| 5,368,555 A | 11/1994 | Sussman et al. |
| 5,368,562 A | 11/1994 | Blomquist et al. |
| 5,370,612 A | 12/1994 | Maeda et al. |
| 5,370,674 A | 12/1994 | Farrell |
| 5,371,687 A | 12/1994 | Holmes, II et al. |
| 5,374,251 A | 12/1994 | Smith |
| 5,374,813 A | 12/1994 | Shipp |
| 5,374,965 A | 12/1994 | Kanno |
| 5,375,604 A | 12/1994 | Kelly et al. |
| 5,376,070 A | 12/1994 | Colman et al. |
| 5,376,263 A | 12/1994 | Fischel |
| 5,377,864 A | 1/1995 | Blechl et al. |
| 5,378,231 A | 1/1995 | Johnson et al. |
| 5,379,214 A | 1/1995 | Arbuckle et al. |
| 5,381,510 A | 1/1995 | Ford et al. |
| 5,385,564 A | 1/1995 | Slater et al. |
| 5,389,078 A | 2/1995 | Zalesky et al. |
| 5,390,238 A | 2/1995 | Kirk et al. |
| 5,392,951 A | 2/1995 | Gardner et al. |
| 5,394,732 A | 3/1995 | Johnson et al. |
| 5,395,320 A | 3/1995 | Padda et al. |
| 5,395,321 A | 3/1995 | Kawahara et al. |
| 5,398,336 A | 3/1995 | Tantry et al. |
| 5,401,059 A | 3/1995 | Ferrario |
| 5,401,342 A | 3/1995 | Vincent et al. |
| D357,312 S | 4/1995 | Riquier et al. |
| 5,404,292 A | 4/1995 | Hendrickson |
| 5,404,384 A | 4/1995 | Colburn et al. |
| 5,406,473 A | 4/1995 | Yoshikura et al. |
| 5,408,576 A | 4/1995 | Bishop |
| 5,411,472 A | 5/1995 | Steg, Jr. et al. |
| 5,411,705 A | 5/1995 | Thor et al. |
| 5,412,715 A | 5/1995 | Volpe |
| 5,415,167 A | 5/1995 | Wilk |
| 5,416,695 A | 5/1995 | Miller et al. |
| 5,417,222 A | 5/1995 | Dempsey et al. |
| 5,420,962 A | 5/1995 | Bakke |
| 5,420,977 A | 5/1995 | Sztipanovits et al. |
| 5,421,343 A | 6/1995 | Feng |
| 5,421,815 A | 6/1995 | Noguchi et al. |
| 5,423,746 A | 6/1995 | Burkett et al. |
| 5,429,595 A | 7/1995 | Wright, Jr. et al. |
| 5,429,602 A | 7/1995 | Hauser |
| 5,431,299 A | 7/1995 | Brewer et al. |
| 5,431,627 A | 7/1995 | Pastrone et al. |
| 5,433,736 A | 7/1995 | Nilsson |
| 5,438,510 A | 8/1995 | Bryant et al. |
| 5,438,607 A | 8/1995 | Przygoda, Jr. et al. |
| 5,440,699 A | 8/1995 | Farrand et al. |
| 5,441,047 A | 8/1995 | David et al. |

(56) References Cited

U.S. PATENT DOCUMENTS

| | | |
|---|---|---|
| 5,441,636 A | 8/1995 | Chevallet et al. |
| 5,445,294 A | 8/1995 | Gardner et al. |
| 5,445,610 A | 8/1995 | Evert |
| 5,445,621 A | 8/1995 | Poli et al. |
| 5,446,868 A | 8/1995 | Gardea, II et al. |
| 5,453,098 A | 9/1995 | Botts et al. |
| 5,455,851 A | 10/1995 | Chaco et al. |
| 5,458,123 A | 10/1995 | Unger |
| 5,460,294 A | 10/1995 | Williams |
| 5,460,605 A | 10/1995 | Tuttle et al. |
| 5,461,665 A | 10/1995 | Shur et al. |
| 5,462,051 A | 10/1995 | Oka et al. |
| 5,464,392 A | 11/1995 | Epstein et al. |
| 5,465,286 A | 11/1995 | Clare et al. |
| 5,467,773 A | 11/1995 | Bergelson et al. |
| 5,468,110 A | 11/1995 | McDonald et al. |
| 5,468,388 A | 11/1995 | Goddard et al. |
| 5,469,855 A | 11/1995 | Pompei et al. |
| 5,470,483 A | 11/1995 | Bene et al. |
| 5,471,382 A | 11/1995 | Tallman et al. |
| 5,472,614 A | 12/1995 | Rossi |
| 5,474,552 A | 12/1995 | Palti |
| 5,474,683 A | 12/1995 | Bryant et al. |
| 5,482,043 A | 1/1996 | Zulauf |
| 5,482,446 A | 1/1996 | Williamson et al. |
| 5,484,397 A | 1/1996 | Twardowski |
| 5,485,408 A | 1/1996 | Blomquist |
| 5,487,827 A | 1/1996 | Peterson et al. |
| 5,489,385 A | 2/1996 | Raabe et al. |
| 5,490,610 A | 2/1996 | Pearson |
| 5,490,925 A | 2/1996 | Eigendorf |
| 5,494,592 A | 2/1996 | Latham, Jr. et al. |
| 5,496,265 A | 3/1996 | Langley et al. |
| 5,496,273 A | 3/1996 | Pastrone et al. |
| 5,498,338 A | 3/1996 | Kruger et al. |
| 5,502,944 A | 4/1996 | Kraft et al. |
| 5,503,801 A | 4/1996 | Brugger |
| 5,507,412 A | 4/1996 | Ebert et al. |
| 5,508,912 A | 4/1996 | Schneiderman |
| 5,509,422 A | 4/1996 | Fukami |
| 5,509,895 A | 4/1996 | Noguchi et al. |
| 5,513,957 A | 5/1996 | O'Leary |
| 5,514,088 A | 5/1996 | Zakko |
| 5,514,095 A | 5/1996 | Brightbill et al. |
| 5,515,426 A | 5/1996 | Yacenda et al. |
| 5,520,450 A | 5/1996 | Colson, Jr. et al. |
| 5,520,637 A | 5/1996 | Pager et al. |
| 5,520,640 A | 5/1996 | Utterberg |
| 5,522,396 A | 6/1996 | Langer et al. |
| 5,522,798 A | 6/1996 | Johnson et al. |
| 5,522,998 A | 6/1996 | Polaschegg |
| 5,526,428 A | 6/1996 | Arnold |
| 5,528,503 A | 6/1996 | Moore et al. |
| 5,529,063 A | 6/1996 | Hill |
| 5,531,680 A | 7/1996 | Dumas et al. |
| 5,531,697 A | 7/1996 | Olsen et al. |
| 5,531,698 A | 7/1996 | Olsen |
| 5,533,079 A | 7/1996 | Colburn et al. |
| 5,533,981 A | 7/1996 | Mandro et al. |
| 5,534,691 A | 7/1996 | Holdaway et al. |
| 5,536,084 A | 7/1996 | Curtis et al. |
| 5,537,313 A | 7/1996 | Pirelli |
| 5,537,853 A | 7/1996 | Finburgh et al. |
| 5,540,808 A | 7/1996 | Vincent et al. |
| 5,540,842 A | 7/1996 | Aoyama et al. |
| 5,542,420 A | 8/1996 | Goldman et al. |
| 5,542,919 A | 8/1996 | Simon et al. |
| 5,544,649 A | 8/1996 | David et al. |
| 5,544,651 A | 8/1996 | Wilk |
| 5,544,661 A | 8/1996 | Davis et al. |
| 5,545,131 A | 8/1996 | Davankov |
| 5,545,140 A | 8/1996 | Conero et al. |
| 5,546,580 A | 8/1996 | Seliger et al. |
| 5,547,470 A | 8/1996 | Johnson et al. |
| 5,549,117 A | 8/1996 | Tacklind et al. |
| 5,549,460 A | 8/1996 | O'Leary |
| 5,553,609 A | 9/1996 | Chen et al. |
| 5,558,638 A | 9/1996 | Evers et al. |
| 5,558,640 A | 9/1996 | Pfeiler et al. |
| 5,560,352 A | 10/1996 | Heim et al. |
| 5,562,232 A | 10/1996 | Pearson |
| 5,562,621 A | 10/1996 | Claude et al. |
| 5,563,347 A | 10/1996 | Martin et al. |
| 5,564,803 A | 10/1996 | McDonald et al. |
| 5,568,912 A | 10/1996 | Minami et al. |
| 5,569,186 A | 10/1996 | Lord et al. |
| 5,569,187 A | 10/1996 | Kaiser |
| 5,570,026 A | 10/1996 | Buffaloe, IV et al. |
| 5,571,258 A | 11/1996 | Pearson |
| 5,573,502 A | 11/1996 | LeCocq et al. |
| 5,573,506 A | 11/1996 | Vasko |
| 5,575,632 A | 11/1996 | Morris et al. |
| 5,576,952 A | 11/1996 | Stutman et al. |
| 5,578,070 A | 11/1996 | Utterberg |
| 5,579,001 A | 11/1996 | Dempsey et al. |
| 5,579,378 A | 11/1996 | Arlinghaus, Jr. |
| 5,581,369 A | 12/1996 | Righter et al. |
| 5,581,687 A | 12/1996 | Lyle et al. |
| 5,582,593 A | 12/1996 | Hultman |
| 5,583,758 A | 12/1996 | McIlroy et al. |
| 5,588,815 A | 12/1996 | Zaleski, II |
| 5,588,816 A | 12/1996 | Abbott et al. |
| 5,589,932 A | 12/1996 | Garcia-Rubio et al. |
| 5,590,648 A | 1/1997 | Mitchell et al. |
| 5,591,251 A | 1/1997 | Brugger |
| 5,591,344 A | 1/1997 | Kenley et al. |
| 5,593,267 A | 1/1997 | McDonald et al. |
| 5,594,637 A | 1/1997 | Eisenberg et al. |
| 5,594,786 A | 1/1997 | Chaco et al. |
| 5,597,995 A | 1/1997 | Williams et al. |
| 5,598,536 A | 1/1997 | Slaughter, III et al. |
| 5,601,445 A | 2/1997 | Schipper et al. |
| 5,605,540 A | 2/1997 | Utterberg |
| 5,609,572 A | 3/1997 | Lang |
| 5,609,575 A | 3/1997 | Larson et al. |
| 5,609,576 A | 3/1997 | Voss et al. |
| 5,609,770 A | 3/1997 | Zimmerman et al. |
| 5,613,115 A | 3/1997 | Gihl et al. |
| 5,614,677 A | 3/1997 | Wamsiedler et al. |
| 5,616,248 A | 4/1997 | Schal |
| 5,618,441 A | 4/1997 | Rosa et al. |
| 5,619,428 A | 4/1997 | Lee et al. |
| 5,619,991 A | 4/1997 | Sloane |
| 5,620,608 A | 4/1997 | Rosa et al. |
| 5,623,652 A | 4/1997 | Vora et al. |
| 5,623,925 A | 4/1997 | Swenson et al. |
| 5,626,144 A | 5/1997 | Tacklind et al. |
| 5,628,619 A | 5/1997 | Wilson |
| 5,628,908 A | 5/1997 | Kamen |
| 5,629,871 A | 5/1997 | Love et al. |
| 5,630,710 A | 5/1997 | Tune et al. |
| 5,631,844 A | 5/1997 | Margrey et al. |
| 5,633,910 A | 5/1997 | Cohen |
| D380,260 S | 6/1997 | Hyman |
| 5,634,893 A | 6/1997 | Rishton |
| 5,637,081 A | 6/1997 | Noguchi et al. |
| 5,637,082 A | 6/1997 | Pages et al. |
| 5,637,093 A | 6/1997 | Hyman et al. |
| 5,640,301 A | 6/1997 | Roecher et al. |
| 5,640,953 A | 6/1997 | Bishop et al. |
| 5,640,995 A | 6/1997 | Packard et al. |
| 5,641,405 A | 6/1997 | Keshaviah et al. |
| 5,641,628 A | 6/1997 | Bianchi |
| 5,643,193 A | 7/1997 | Papillon et al. |
| 5,643,201 A | 7/1997 | Peabody et al. |
| 5,643,212 A | 7/1997 | Coutre et al. |
| 5,643,250 A | 7/1997 | Utterberg |
| 5,645,734 A | 7/1997 | Kenley et al. |
| 5,647,853 A | 7/1997 | Feldmann et al. |
| 5,647,854 A | 7/1997 | Olsen et al. |
| 5,650,071 A | 7/1997 | Brugger et al. |
| 5,651,775 A | 7/1997 | Walker et al. |
| 5,652,566 A | 7/1997 | Lambert |
| 5,658,240 A | 8/1997 | Urdahl et al. |

(56) References Cited

U.S. PATENT DOCUMENTS

| | | |
|---|---|---|
| 5,658,250 A | 8/1997 | Blomquist et al. |
| 5,658,456 A | 8/1997 | Kenley et al. |
| 5,661,978 A | 9/1997 | Holmes et al. |
| 5,664,270 A | 9/1997 | Bell et al. |
| 5,666,404 A | 9/1997 | Ciccotelli et al. |
| 5,674,199 A | 10/1997 | Brugger |
| 5,678,562 A | 10/1997 | Sellers |
| 5,678,568 A | 10/1997 | Uchikubo et al. |
| 5,681,285 A | 10/1997 | Ford et al. |
| 5,681,294 A | 10/1997 | Osborne et al. |
| 5,682,526 A | 10/1997 | Smokoff et al. |
| 5,683,355 A | 11/1997 | Fini et al. |
| 5,683,367 A | 11/1997 | Jordan et al. |
| 5,683,381 A | 11/1997 | Carr et al. |
| 5,685,844 A | 11/1997 | Marttila |
| 5,685,988 A | 11/1997 | Malchesky |
| 5,685,989 A | 11/1997 | Krivitski et al. |
| 5,687,717 A | 11/1997 | Halpern |
| 5,687,734 A | 11/1997 | Dempsey et al. |
| 5,690,614 A | 11/1997 | Carr et al. |
| 5,690,831 A | 11/1997 | Kenley et al. |
| 5,695,473 A | 12/1997 | Olsen |
| 5,697,951 A | 12/1997 | Harpstead |
| 5,700,998 A | 12/1997 | Palti |
| 5,701,894 A | 12/1997 | Cherry et al. |
| 5,702,597 A | 12/1997 | Chevallet et al. |
| 5,702,606 A | 12/1997 | Peter, Jr. et al. |
| 5,704,351 A | 1/1998 | Mortara et al. |
| 5,704,364 A | 1/1998 | Saltzstein et al. |
| 5,704,366 A | 1/1998 | Tacklind et al. |
| 5,712,798 A | 1/1998 | Langley et al. |
| 5,712,912 A | 1/1998 | Tomko et al. |
| 5,713,485 A | 2/1998 | Liff et al. |
| 5,713,856 A | 2/1998 | Eggers et al. |
| 5,715,823 A | 2/1998 | Wood et al. |
| 5,716,114 A | 2/1998 | Holmes et al. |
| 5,716,194 A | 2/1998 | Butterfield et al. |
| 5,718,562 A | 2/1998 | Lawless et al. |
| 5,719,761 A | 2/1998 | Gatti et al. |
| RE35,743 E | 3/1998 | Pearson |
| 5,722,947 A | 3/1998 | Jeppsson et al. |
| 5,724,025 A | 3/1998 | Tavori |
| 5,724,478 A | 3/1998 | Thweatt |
| 5,724,580 A | 3/1998 | Levin et al. |
| 5,725,511 A | 3/1998 | Urrutia |
| 5,725,776 A | 3/1998 | Kenley et al. |
| 5,729,653 A | 3/1998 | Magliochetti et al. |
| 5,730,712 A | 3/1998 | Falkvall et al. |
| 5,730,730 A | 3/1998 | Darling, Jr. |
| 5,732,709 A | 3/1998 | Tacklind et al. |
| 5,733,259 A | 3/1998 | Valcke et al. |
| 5,735,887 A | 4/1998 | Barreras, Sr. et al. |
| 5,737,539 A | 4/1998 | Edelson et al. |
| 5,740,185 A | 4/1998 | Bosse |
| 5,740,800 A | 4/1998 | Hendrickson et al. |
| 5,744,042 A | 4/1998 | Stange et al. |
| 5,745,366 A | 4/1998 | Higham et al. |
| 5,745,378 A | 4/1998 | Barker et al. |
| 5,752,917 A | 5/1998 | Fuchs |
| 5,752,976 A | 5/1998 | Duffin et al. |
| 5,755,563 A | 5/1998 | Clegg et al. |
| 5,759,044 A | 6/1998 | Redmond |
| 5,762,782 A | 6/1998 | Kenley et al. |
| 5,763,266 A | 6/1998 | Palsson et al. |
| 5,764,923 A | 6/1998 | Tallman et al. |
| 5,766,155 A | 6/1998 | Hyman et al. |
| 5,769,811 A | 6/1998 | Stacey et al. |
| 5,771,657 A | 6/1998 | Lasher et al. |
| 5,772,585 A | 6/1998 | Lavin et al. |
| 5,772,586 A | 6/1998 | Heinonen et al. |
| 5,772,635 A | 6/1998 | Dastur et al. |
| 5,772,637 A | 6/1998 | Heinzmann et al. |
| 5,776,057 A | 7/1998 | Swenson et al. |
| 5,776,091 A | 7/1998 | Brugger et al. |
| 5,776,345 A | 7/1998 | Truitt et al. |
| 5,778,345 A | 7/1998 | McCartney |
| 5,778,882 A | 7/1998 | Raymond et al. |
| 5,781,442 A | 7/1998 | Chamberlain et al. |
| 5,782,575 A | 7/1998 | Vincent et al. |
| 5,782,805 A | 7/1998 | Meinzer et al. |
| 5,782,878 A | 7/1998 | Morgan et al. |
| 5,784,547 A | 7/1998 | Dittmar et al. |
| 5,785,650 A | 7/1998 | Akasaka et al. |
| 5,788,669 A | 8/1998 | Peterson |
| 5,788,851 A | 8/1998 | Kenley et al. |
| 5,790,409 A | 8/1998 | Fedor et al. |
| 5,790,752 A | 8/1998 | Anglin et al. |
| 5,791,342 A | 8/1998 | Woodard |
| 5,791,880 A | 8/1998 | Wilson |
| 5,793,861 A | 8/1998 | Haigh |
| 5,793,969 A | 8/1998 | Kamentsky et al. |
| 5,795,317 A | 8/1998 | Brierton et al. |
| 5,795,327 A | 8/1998 | Wilson et al. |
| 5,797,515 A | 8/1998 | Liff et al. |
| 5,800,387 A | 9/1998 | Duffy et al. |
| 5,803,906 A | 9/1998 | Pratt et al. |
| 5,805,442 A | 9/1998 | Crater et al. |
| 5,805,456 A | 9/1998 | Higham et al. |
| 5,805,505 A | 9/1998 | Zheng et al. |
| 5,807,321 A | 9/1998 | Stoker et al. |
| 5,807,322 A | 9/1998 | Lindsey et al. |
| 5,807,336 A | 9/1998 | Chen et al. |
| 5,810,747 A | 9/1998 | Brudny et al. |
| 5,814,015 A | 9/1998 | Cowen et al. |
| 5,815,566 A | 9/1998 | Ramot et al. |
| 5,816,779 A | 10/1998 | Lawless et al. |
| 5,822,418 A | 10/1998 | Yacenda et al. |
| 5,822,544 A | 10/1998 | Chaco et al. |
| 5,823,949 A | 10/1998 | Goltra |
| 5,826,237 A | 10/1998 | Macrae et al. |
| 5,829,438 A | 11/1998 | Gibbs et al. |
| 5,830,185 A | 11/1998 | Block, Jr. |
| 5,832,448 A | 11/1998 | Brown |
| 5,832,450 A | 11/1998 | Myers et al. |
| 5,833,599 A | 11/1998 | Schrier et al. |
| 5,836,908 A | 11/1998 | Beden et al. |
| 5,841,975 A | 11/1998 | Layne et al. |
| 5,842,841 A | 12/1998 | Danby et al. |
| 5,842,976 A | 12/1998 | Williamson |
| 5,845,253 A | 12/1998 | Rensimer et al. |
| 5,846,419 A | 12/1998 | Nederlof |
| 5,848,593 A | 12/1998 | McGrady et al. |
| 5,849,065 A | 12/1998 | Wojke |
| 5,851,186 A | 12/1998 | Wood et al. |
| 5,851,202 A | 12/1998 | Carlsson |
| 5,852,590 A | 12/1998 | De La Huerga |
| 5,853,387 A | 12/1998 | Clegg et al. |
| 5,855,550 A | 1/1999 | Buyan et al. |
| 5,857,967 A | 1/1999 | Frid et al. |
| 5,858,238 A | 1/1999 | McRea et al. |
| 5,858,239 A | 1/1999 | Kenley et al. |
| 5,859,972 A | 1/1999 | Subramaniam et al. |
| 5,863,421 A | 1/1999 | Peter, Jr. et al. |
| 5,865,745 A | 2/1999 | Schmitt et al. |
| 5,865,786 A | 2/1999 | Sibalis et al. |
| 5,866,880 A | 2/1999 | Seitz et al. |
| 5,867,821 A | 2/1999 | Ballantyne et al. |
| 5,871,465 A | 2/1999 | Vasko |
| 5,871,694 A | 2/1999 | Beden et al. |
| 5,873,853 A | 2/1999 | Keilman et al. |
| 5,875,282 A | 2/1999 | Jordan et al. |
| 5,876,611 A | 3/1999 | Shettigar |
| 5,876,926 A | 3/1999 | Beecham |
| 5,880,443 A | 3/1999 | McDonald et al. |
| 5,882,338 A | 3/1999 | Gray |
| 5,883,370 A | 3/1999 | Walker et al. |
| 5,883,576 A | 3/1999 | De La Huerga |
| 5,885,245 A | 3/1999 | Lynch et al. |
| 5,891,035 A | 4/1999 | Wood et al. |
| 5,891,734 A | 4/1999 | Gill et al. |
| 5,893,697 A | 4/1999 | Zini et al. |
| 5,894,273 A | 4/1999 | Meador et al. |
| 5,895,368 A | 4/1999 | Utterberg |
| 5,895,371 A | 4/1999 | Jordan et al. |

(56) References Cited

U.S. PATENT DOCUMENTS

| | | |
|---|---|---|
| 5,895,578 A | 4/1999 | Simard et al. |
| 5,897,493 A | 4/1999 | Brown |
| 5,897,530 A | 4/1999 | Jackson |
| 5,897,989 A | 4/1999 | Beecham |
| 5,899,665 A | 5/1999 | Makino et al. |
| 5,899,855 A | 5/1999 | Brown |
| 5,899,998 A | 5/1999 | McGauley et al. |
| 5,901,150 A | 5/1999 | Dupouy et al. |
| 5,902,336 A | 5/1999 | Mishkin |
| 5,902,476 A | 5/1999 | Twardowski |
| 5,904,668 A | 5/1999 | Hyman et al. |
| 5,905,653 A | 5/1999 | Higham et al. |
| 5,907,291 A | 5/1999 | Chen et al. |
| 5,908,027 A | 6/1999 | Butterfield et al. |
| 5,910,107 A | 6/1999 | Iliff |
| 5,910,252 A | 6/1999 | Truitt et al. |
| 5,911,132 A | 6/1999 | Sloane |
| 5,911,687 A | 6/1999 | Sano et al. |
| 5,912,818 A | 6/1999 | McGrady et al. |
| 5,913,197 A | 6/1999 | Kameda |
| 5,913,310 A | 6/1999 | Brown |
| 5,915,240 A | 6/1999 | Karpf |
| 5,919,154 A | 7/1999 | Toavs et al. |
| 5,919,369 A | 7/1999 | Ash |
| 5,921,938 A | 7/1999 | Aoyama et al. |
| 5,921,951 A | 7/1999 | Morris |
| 5,923,018 A | 7/1999 | Kameda et al. |
| 5,924,074 A | 7/1999 | Evans |
| 5,924,103 A | 7/1999 | Ahmed et al. |
| 5,925,011 A | 7/1999 | Faict et al. |
| 5,927,540 A | 7/1999 | Godlewski |
| 5,928,744 A | 7/1999 | Heilmann et al. |
| 5,928,889 A | 7/1999 | Bakich et al. |
| 5,931,791 A | 8/1999 | Saltzstein et al. |
| 5,931,990 A | 8/1999 | Andrews |
| 5,932,103 A | 8/1999 | Kenley et al. |
| 5,932,110 A | 8/1999 | Shah |
| 5,935,060 A | 8/1999 | Iliff |
| 5,935,099 A | 8/1999 | Peterson et al. |
| 5,935,106 A | 8/1999 | Olsen |
| 5,938,413 A | 8/1999 | Makino et al. |
| 5,938,634 A | 8/1999 | Packard |
| 5,939,326 A | 8/1999 | Chupp et al. |
| 5,939,699 A | 8/1999 | Perttunen et al. |
| 5,940,306 A | 8/1999 | Gardner et al. |
| 5,940,802 A | 8/1999 | Hildebrand et al. |
| 5,941,829 A | 8/1999 | Saltzstein et al. |
| 5,942,986 A | 8/1999 | Shabot et al. |
| 5,943,423 A | 8/1999 | Muftic |
| 5,943,633 A | 8/1999 | Wilson et al. |
| 5,944,659 A | 8/1999 | Flach et al. |
| 5,944,684 A | 8/1999 | Roberts et al. |
| 5,945,651 A | 8/1999 | Chorosinski et al. |
| 5,946,083 A | 8/1999 | Melendez et al. |
| 5,946,659 A | 8/1999 | Lancelot et al. |
| 5,947,937 A | 9/1999 | Urrutia et al. |
| 5,948,251 A | 9/1999 | Brugger |
| 5,950,006 A | 9/1999 | Crater et al. |
| 5,951,300 A | 9/1999 | Brown |
| 5,951,510 A | 9/1999 | Barak |
| 5,951,870 A | 9/1999 | Utterberg |
| 5,954,640 A | 9/1999 | Szabo |
| 5,954,885 A | 9/1999 | Bollish et al. |
| 5,954,958 A | 9/1999 | Folden |
| 5,954,971 A | 9/1999 | Pages et al. |
| 5,956,023 A | 9/1999 | Lyle et al. |
| 5,957,153 A | 9/1999 | Frey et al. |
| 5,957,885 A | 9/1999 | Bollish et al. |
| 5,959,529 A | 9/1999 | Kail, IV |
| 5,960,085 A | 9/1999 | De La Huerga |
| 5,960,160 A | 9/1999 | Clark et al. |
| 5,960,403 A | 9/1999 | Brown |
| 5,960,991 A | 10/1999 | Ophardt |
| 5,961,446 A | 10/1999 | Beller et al. |
| 5,961,448 A | 10/1999 | Swenson et al. |
| 5,961,487 A | 10/1999 | Davis |
| 5,964,700 A | 10/1999 | Tallman et al. |
| 5,966,304 A | 10/1999 | Cook et al. |
| 5,967,975 A | 10/1999 | Ridgeway |
| 5,970,423 A | 10/1999 | Langley et al. |
| 5,971,593 A | 10/1999 | McGrady |
| 5,971,921 A | 10/1999 | Timbel |
| 5,971,948 A | 10/1999 | Pages et al. |
| 5,974,124 A | 10/1999 | Schlueter, Jr. et al. |
| 5,975,737 A | 11/1999 | Crater et al. |
| 5,980,481 A | 11/1999 | Gorsuch |
| 5,980,490 A | 11/1999 | Tsoukalis |
| 5,980,741 A | 11/1999 | Schnell et al. |
| 5,983,193 A | 11/1999 | Heinonen et al. |
| 5,983,947 A | 11/1999 | Utterberg |
| 5,984,891 A | 11/1999 | Keilman et al. |
| 5,987,519 A | 11/1999 | Peifer et al. |
| 5,989,238 A | 11/1999 | Ginsburg |
| 5,989,318 A | 11/1999 | Schroll |
| 5,989,423 A | 11/1999 | Kamen et al. |
| 5,991,731 A | 11/1999 | Colon et al. |
| 5,993,046 A | 11/1999 | McGrady et al. |
| 5,993,420 A | 11/1999 | Hyman et al. |
| 5,995,077 A | 11/1999 | Wilcox et al. |
| 5,995,965 A | 11/1999 | Experton |
| 5,997,167 A | 12/1999 | Crater et al. |
| 5,997,476 A | 12/1999 | Brown |
| 6,001,201 A | 12/1999 | Vincent et al. |
| 6,003,006 A | 12/1999 | Colella et al. |
| 6,004,020 A | 12/1999 | Bartur |
| 6,004,276 A | 12/1999 | Wright et al. |
| 6,004,311 A | 12/1999 | Heilmann et al. |
| 6,006,191 A | 12/1999 | DiRienzo |
| 6,009,333 A | 12/1999 | Chaco |
| 6,010,454 A | 1/2000 | Arieff et al. |
| 6,010,623 A | 1/2000 | Schnell et al. |
| 6,011,858 A | 1/2000 | Stock et al. |
| 6,011,999 A | 1/2000 | Holmes |
| 6,012,034 A | 1/2000 | Hamparian et al. |
| 6,013,057 A | 1/2000 | Danby et al. |
| 6,014,631 A | 1/2000 | Teagarden et al. |
| 6,016,444 A | 1/2000 | John |
| 6,017,318 A | 1/2000 | Gauthier et al. |
| 6,018,713 A | 1/2000 | Coli et al. |
| 6,019,745 A | 2/2000 | Gray |
| 6,019,824 A | 2/2000 | Schnell |
| 6,021,392 A | 2/2000 | Lester et al. |
| 6,022,315 A | 2/2000 | Iliff |
| 6,023,522 A | 2/2000 | Draganoff et al. |
| 6,024,539 A | 2/2000 | Blomquist |
| 6,024,699 A | 2/2000 | Allen et al. |
| 6,024,720 A | 2/2000 | Chandler et al. |
| 6,027,217 A | 2/2000 | McClure et al. |
| 6,029,138 A | 2/2000 | Khorasani et al. |
| 6,032,119 A | 2/2000 | Brown et al. |
| 6,032,155 A | 2/2000 | de la Huerga |
| 6,033,076 A | 3/2000 | Braeuning et al. |
| 6,039,251 A | 3/2000 | Crone et al. |
| 6,039,467 A | 3/2000 | Holmes |
| 6,042,784 A | 3/2000 | Wamsiedler et al. |
| 6,046,806 A | 4/2000 | Thompson |
| 6,047,259 A | 4/2000 | Campbell et al. |
| 6,050,940 A | 4/2000 | Braun et al. |
| 6,051,134 A | 4/2000 | Schnell et al. |
| 6,052,752 A | 4/2000 | Kwon |
| 6,053,967 A | 4/2000 | Heilmann et al. |
| 6,055,487 A | 4/2000 | Margery et al. |
| 6,057,758 A | 5/2000 | Dempsey et al. |
| 6,059,736 A | 5/2000 | Tapper |
| 6,061,603 A | 5/2000 | Papadopoulos et al. |
| 6,065,819 A | 5/2000 | Holmes et al. |
| 6,066,111 A | 5/2000 | Brockhoff |
| 6,068,153 A | 5/2000 | Young et al. |
| 6,069,343 A | 5/2000 | Kolowich |
| 6,071,269 A | 6/2000 | Schnell et al. |
| 6,073,046 A | 6/2000 | Patel et al. |
| 6,074,345 A | 6/2000 | van Oostrom et al. |
| 6,074,359 A | 6/2000 | Keshaviah et al. |
| 6,079,621 A | 6/2000 | Vardanyan et al. |

(56) References Cited

U.S. PATENT DOCUMENTS

| | | |
|---|---|---|
| 6,080,106 A | 6/2000 | Lloyd et al. |
| 6,081,048 A | 6/2000 | Bergmann et al. |
| 6,082,776 A | 7/2000 | Feinberg |
| 6,083,206 A | 7/2000 | Molko |
| 6,093,146 A | 7/2000 | Filangeri |
| 6,095,985 A | 8/2000 | Raymond et al. |
| 6,101,407 A | 8/2000 | Groezinger |
| 6,101,478 A | 8/2000 | Brown |
| 6,102,856 A | 8/2000 | Groff et al. |
| 6,108,399 A | 8/2000 | Hernandez-Guerra et al. |
| 6,108,588 A | 8/2000 | McGrady |
| 6,109,774 A | 8/2000 | Holmes et al. |
| 6,112,224 A | 8/2000 | Peifer et al. |
| RE36,871 E | 9/2000 | Epstein et al. |
| 6,113,554 A | 9/2000 | Gilcher et al. |
| 6,116,461 A | 9/2000 | Broadfield et al. |
| 6,117,342 A | 9/2000 | Schnell et al. |
| 6,117,940 A | 9/2000 | Bond et al. |
| 6,123,524 A | 9/2000 | Danby et al. |
| 6,125,350 A | 9/2000 | Dirbas |
| 6,129,517 A | 10/2000 | Danby et al. |
| 6,129,699 A | 10/2000 | Haight et al. |
| 6,132,371 A | 10/2000 | Dempsey et al. |
| 6,132,616 A | 10/2000 | Twardowski et al. |
| 6,134,504 A | 10/2000 | Douglas et al. |
| 6,135,949 A | 10/2000 | Russo et al. |
| 6,137,776 A | 10/2000 | Bauerschmidt et al. |
| 6,139,495 A | 10/2000 | De La Huerga |
| 6,139,528 A | 10/2000 | Kistner et al. |
| 6,139,748 A | 10/2000 | Ericson et al. |
| 6,139,754 A | 10/2000 | Hartranft |
| 6,139,757 A | 10/2000 | Ohmura |
| 6,142,974 A | 11/2000 | Kistner et al. |
| 6,142,975 A | 11/2000 | Kistner et al. |
| 6,144,922 A | 11/2000 | Douglas et al. |
| 6,145,695 A | 11/2000 | Garrigues |
| 6,146,359 A | 11/2000 | Carr et al. |
| 6,146,523 A | 11/2000 | Kenley et al. |
| 6,146,536 A | 11/2000 | Twardowski |
| 6,148,297 A | 11/2000 | Swor et al. |
| 6,149,063 A | 11/2000 | Reynolds et al. |
| 6,151,298 A | 11/2000 | Bernhardsson et al. |
| 6,151,536 A | 11/2000 | Arnold et al. |
| 6,152,364 A | 11/2000 | Schoonen et al. |
| 6,154,668 A | 11/2000 | Pedersen et al. |
| 6,154,726 A | 11/2000 | Rensimer et al. |
| 6,157,914 A | 12/2000 | Seto et al. |
| 6,158,965 A | 12/2000 | Butterfield et al. |
| 6,160,478 A | 12/2000 | Jacobsen et al. |
| 6,161,095 A | 12/2000 | Brown |
| 6,163,737 A | 12/2000 | Fedor et al. |
| 6,165,154 A | 12/2000 | Gray et al. |
| 6,168,563 B1 | 1/2001 | Brown |
| 6,168,578 B1 | 1/2001 | Diamond |
| 6,170,007 B1 | 1/2001 | Venkatraman et al. |
| 6,170,746 B1 | 1/2001 | Brook et al. |
| 6,171,112 B1 | 1/2001 | Clark et al. |
| 6,171,237 B1 | 1/2001 | Boaz et al. |
| 6,171,264 B1 | 1/2001 | Bader |
| 6,171,484 B1 | 1/2001 | Schnell et al. |
| 6,173,198 B1 | 1/2001 | Schulze et al. |
| 6,175,688 B1 | 1/2001 | Cassidy et al. |
| 6,175,779 B1 | 1/2001 | Barrett |
| 6,175,977 B1 | 1/2001 | Schumacher et al. |
| 6,176,903 B1 | 1/2001 | Wamsiedler |
| 6,182,047 B1 | 1/2001 | Dirbas |
| 6,183,417 B1 | 2/2001 | Geheb et al. |
| 6,186,145 B1 | 2/2001 | Brown |
| 6,187,198 B1 | 2/2001 | Utterberg |
| 6,188,988 B1 | 2/2001 | Barry et al. |
| 6,192,320 B1 | 2/2001 | Margrey et al. |
| 6,193,480 B1 | 2/2001 | Butterfield |
| 6,193,684 B1 | 2/2001 | Burbank et al. |
| 6,195,887 B1 | 3/2001 | Danby et al. |
| 6,196,992 B1 | 3/2001 | Keilman et al. |
| 6,198,394 B1 | 3/2001 | Jacobsen et al. |
| 6,200,264 B1 | 3/2001 | Satherley et al. |
| 6,200,289 B1 | 3/2001 | Hochman et al. |
| 6,203,495 B1 | 3/2001 | Bardy |
| 6,203,528 B1 | 3/2001 | Deckert et al. |
| 6,206,238 B1 | 3/2001 | Ophardt |
| 6,206,829 B1 | 3/2001 | Iliff |
| 6,206,954 B1 | 3/2001 | Schnell et al. |
| 6,210,361 B1 | 4/2001 | Kamen et al. |
| 6,213,391 B1 | 4/2001 | Lewis |
| 6,213,738 B1 | 4/2001 | Danby et al. |
| 6,219,439 B1 | 4/2001 | Burger |
| 6,219,587 B1 | 4/2001 | Ahlin et al. |
| 6,220,299 B1 | 4/2001 | Arvidsson et al. |
| 6,221,011 B1 | 4/2001 | Bardy |
| 6,221,012 B1 | 4/2001 | Maschke et al. |
| 6,222,619 B1 | 4/2001 | Herron et al. |
| 6,224,549 B1 | 5/2001 | Van Drongelen |
| 6,225,901 B1 | 5/2001 | Kail, IV |
| 6,226,564 B1 | 5/2001 | Stuart |
| 6,228,047 B1 | 5/2001 | Dadson |
| 6,229,957 B1 | 5/2001 | Baker |
| 6,230,927 B1 | 5/2001 | Schoonen et al. |
| 6,234,991 B1 | 5/2001 | Gorsuch |
| 6,234,992 B1 | 5/2001 | Haight et al. |
| 6,234,997 B1 | 5/2001 | Kamen et al. |
| 6,236,809 B1 | 5/2001 | Cassidy et al. |
| 6,245,013 B1 | 6/2001 | Minoz et al. |
| 6,245,039 B1 | 6/2001 | Brugger et al. |
| 6,246,473 B1 | 6/2001 | Smith, Jr. et al. |
| 6,248,063 B1 | 6/2001 | Barnhill et al. |
| 6,248,065 B1 | 6/2001 | Brown |
| 6,251,167 B1 | 6/2001 | Berson |
| 6,251,279 B1 | 6/2001 | Peterson et al. |
| 6,254,567 B1 | 7/2001 | Treu et al. |
| 6,255,951 B1 | 7/2001 | De La Huerga |
| 6,256,643 B1 | 7/2001 | Cork et al. |
| 6,256,967 B1 | 7/2001 | Hebron et al. |
| 6,259,355 B1 | 7/2001 | Chaco et al. |
| 6,259,654 B1 | 7/2001 | De La Huerga |
| 6,260,715 B1 | 7/2001 | Simard et al. |
| 6,261,261 B1 | 7/2001 | Gordon |
| 6,261,809 B1 | 7/2001 | Bertling et al. |
| 6,266,645 B1 | 7/2001 | Simpson |
| 6,269,340 B1 | 7/2001 | Ford et al. |
| D446,854 S | 8/2001 | Cheney, II et al. |
| 6,270,455 B1 | 8/2001 | Brown |
| 6,270,457 B1 | 8/2001 | Bardy |
| 6,272,394 B1 | 8/2001 | Lipps |
| 6,272,505 B1 | 8/2001 | De La Huerga |
| 6,274,034 B1 | 8/2001 | Nikaido et al. |
| 6,274,103 B1 | 8/2001 | Taylor |
| 6,277,072 B1 | 8/2001 | Bardy |
| 6,280,632 B1 | 8/2001 | Polaschegg |
| 6,280,634 B1 | 8/2001 | Shah et al. |
| 6,283,322 B1 | 9/2001 | Liff et al. |
| 6,283,944 B1 | 9/2001 | McMullen et al. |
| 6,287,516 B1 | 9/2001 | Matson et al. |
| 6,290,646 B1 | 9/2001 | Cosentino |
| 6,290,650 B1 | 9/2001 | Butterfield et al. |
| 6,290,669 B1 | 9/2001 | Zicherman |
| 6,293,921 B1 | 9/2001 | Shinmoto et al. |
| 6,294,999 B1 | 9/2001 | Yarin et al. |
| 6,295,506 B1 | 9/2001 | Heinonen |
| 6,302,653 B1 | 10/2001 | Bryant et al. |
| 6,304,788 B1 | 10/2001 | Eady et al. |
| 6,306,088 B1 | 10/2001 | Krausman et al. |
| 6,307,956 B1 | 10/2001 | Black |
| 6,308,171 B1 | 10/2001 | De La Huerga |
| 6,309,673 B1 | 10/2001 | Duponchelle |
| 6,311,163 B1 | 10/2001 | Sheehan et al. |
| 6,312,227 B1 | 11/2001 | Davis |
| 6,312,378 B1 | 11/2001 | Bardy |
| 6,312,414 B1 | 11/2001 | Brockhoff et al. |
| 6,314,384 B1 | 11/2001 | Goetz |
| 6,315,895 B1 | 11/2001 | Summerton et al. |
| 6,317,719 B1 | 11/2001 | Schrier et al. |
| 6,319,200 B1 | 11/2001 | Lai |
| 6,319,221 B1 | 11/2001 | Savage et al. |

(56) References Cited

U.S. PATENT DOCUMENTS

| | | |
|---|---|---|
| 6,321,203 B1 | 11/2001 | Kameda |
| 6,322,504 B1 | 11/2001 | Kirshner |
| 6,322,515 B1 | 11/2001 | Goor et al. |
| 6,322,551 B1 | 11/2001 | Brugger |
| 6,331,252 B1 | 12/2001 | El Sayyid et al. |
| RE37,531 E | 1/2002 | Chaco et al. |
| 6,337,631 B1 | 1/2002 | Pai |
| 6,338,007 B1 | 1/2002 | Broadfield et al. |
| 6,339,732 B1 | 1/2002 | Phoon et al. |
| 6,344,139 B1 | 2/2002 | Utterberg |
| 6,345,260 B1 | 2/2002 | Cummings, Jr. et al. |
| 6,346,886 B1 | 2/2002 | De La Huerga |
| 6,348,162 B1 | 2/2002 | Ash |
| 6,352,200 B1 | 3/2002 | Schoonen et al. |
| 6,353,817 B1 | 3/2002 | Jacobs et al. |
| 6,357,600 B1 | 3/2002 | Scagliarini |
| 6,358,225 B1 | 3/2002 | Butterfield |
| 6,358,237 B1 | 3/2002 | Paukovits |
| 6,361,201 B1 | 3/2002 | Russell et al. |
| 6,361,263 B1 | 3/2002 | Dewey et al. |
| 6,362,591 B1 | 3/2002 | Moberg |
| 6,363,282 B1 | 3/2002 | Nichols et al. |
| 6,363,290 B1 | 3/2002 | Lyle et al. |
| 6,364,143 B1 | 4/2002 | Knierbein |
| 6,364,834 B1 | 4/2002 | Reuss et al. |
| 6,364,857 B1 | 4/2002 | Gray et al. |
| 6,366,282 B1 | 4/2002 | Nichols et al. |
| 6,368,273 B1 | 4/2002 | Brown |
| 6,370,841 B1 | 4/2002 | Chudy et al. |
| 6,381,577 B1 | 4/2002 | Brown |
| 6,382,923 B1 | 5/2002 | Gray |
| 6,385,505 B1 | 5/2002 | Lipps |
| 6,391,541 B1 | 5/2002 | Petersen et al. |
| 6,391,638 B1 | 5/2002 | Shaaltiel |
| 6,393,369 B1 | 5/2002 | Carr |
| 6,397,190 B1 | 5/2002 | Goetz |
| 6,402,702 B1 | 6/2002 | Gilcher et al. |
| 6,406,426 B1 | 6/2002 | Reuss et al. |
| 6,406,631 B1 | 6/2002 | Collins et al. |
| 6,407,335 B1 | 6/2002 | Franklin-Lees et al. |
| 6,408,330 B1 | 6/2002 | De La Huerga |
| 6,416,293 B1 | 7/2002 | Bouchard et al. |
| 6,416,471 B1 | 7/2002 | Kumar et al. |
| 6,421,650 B1 | 7/2002 | Goetz et al. |
| 6,426,056 B2 | 7/2002 | Taylor |
| 6,427,088 B1 | 7/2002 | Bowman, IV et al. |
| 6,434,531 B1 | 8/2002 | Lancelot et al. |
| 6,434,569 B1 | 8/2002 | Tomlinson et al. |
| 6,449,927 B2 | 9/2002 | Hebron et al. |
| 6,450,956 B1 | 9/2002 | Rappaport et al. |
| 6,458,102 B1 | 10/2002 | Mann et al. |
| 6,464,977 B2 | 10/2002 | Kai et al. |
| 6,468,242 B1 | 10/2002 | Wilson et al. |
| 6,470,234 B1 | 10/2002 | McGrady |
| 6,471,089 B2 | 10/2002 | Liff et al. |
| 6,471,645 B1 | 10/2002 | Warkentin et al. |
| 6,475,146 B1 | 11/2002 | Frelburger et al. |
| 6,475,148 B1 | 11/2002 | Jackson et al. |
| 6,475,180 B2 | 11/2002 | Peterson et al. |
| 6,478,737 B2 | 11/2002 | Bardy |
| 6,485,465 B2 | 11/2002 | Moberg et al. |
| 6,489,301 B1 | 12/2002 | Kobira et al. |
| 6,511,138 B1 | 1/2003 | Gardner et al. |
| 6,519,569 B1 | 2/2003 | White et al. |
| 6,537,244 B2 | 3/2003 | Paukovits et al. |
| 6,542,902 B2 | 4/2003 | Dulong et al. |
| 6,542,910 B2 | 4/2003 | Cork et al. |
| 6,544,174 B2 | 4/2003 | West et al. |
| 6,544,228 B1 | 4/2003 | Heitmeier |
| 6,551,243 B2 | 4/2003 | Bocionek et al. |
| 6,551,276 B1 | 4/2003 | Mann et al. |
| 6,554,791 B1 | 4/2003 | Cartledge et al. |
| 6,554,798 B1 | 4/2003 | Mann et al. |
| 6,555,986 B2 | 4/2003 | Moberg |
| 6,558,321 B1 | 5/2003 | Burd et al. |
| 6,561,975 B1 | 5/2003 | Pool et al. |
| 6,562,001 B2 | 5/2003 | Lebel et al. |
| 6,564,104 B2 | 5/2003 | Nelson et al. |
| 6,564,105 B2 | 5/2003 | Starkweather et al. |
| 6,571,128 B2 | 5/2003 | Lebel et al. |
| 6,575,900 B1 | 6/2003 | Zweig et al. |
| 6,577,899 B2 | 6/2003 | Lebel et al. |
| 6,579,232 B2 | 6/2003 | Sakamaki et al. |
| 6,579,253 B1 | 6/2003 | Burbank et al. |
| 6,581,069 B1 | 6/2003 | Robinson et al. |
| 6,582,385 B2 | 6/2003 | Burbank et al. |
| 6,584,336 B1 | 6/2003 | Ali et al. |
| 6,585,157 B2 | 7/2003 | Brandt et al. |
| 6,585,644 B2 | 7/2003 | Lebel et al. |
| 6,585,675 B1 | 7/2003 | O'Mahony et al. |
| 6,592,551 B1 | 7/2003 | Cobb |
| 6,593,528 B2 | 7/2003 | Franklin-Lees et al. |
| 6,595,944 B2 | 7/2003 | Balschat et al. |
| 6,595,948 B2 | 7/2003 | Suzuki et al. |
| 6,602,502 B1 | 8/2003 | Strahilevitz |
| 6,607,485 B2 | 8/2003 | Bardy |
| 6,613,009 B1 | 9/2003 | Bainbridge et al. |
| 6,623,709 B2 | 9/2003 | Taylor |
| 6,635,014 B2 | 10/2003 | Starkweather et al. |
| 6,648,821 B2 | 11/2003 | Lebel et al. |
| 6,656,355 B2 | 12/2003 | Sano |
| 6,659,948 B2 | 12/2003 | Lebel et al. |
| 6,664,893 B1 | 12/2003 | Eveland et al. |
| 6,668,196 B1 | 12/2003 | Villegas et al. |
| 6,673,314 B1 | 1/2004 | Burbank et al. |
| 6,673,376 B1 | 1/2004 | Knerr et al. |
| 6,676,621 B1 | 1/2004 | Menninger |
| 6,685,831 B2 | 2/2004 | Donig et al. |
| 6,687,546 B2 | 2/2004 | Lebel et al. |
| 6,689,091 B2 | 2/2004 | Bui et al. |
| 6,694,191 B2 | 2/2004 | Starkweather et al. |
| 6,694,334 B2 | 2/2004 | DuLong et al. |
| 6,733,446 B2 | 5/2004 | Lebel et al. |
| 6,733,447 B2 | 5/2004 | Lai et al. |
| 6,740,075 B2 | 5/2004 | Lebel et al. |
| 6,745,903 B2 | 6/2004 | Grandics |
| 6,746,398 B2 | 6/2004 | Hervy et al. |
| 6,746,607 B1 | 6/2004 | Vijayalakshmi et al. |
| 6,749,818 B2 | 6/2004 | Sano et al. |
| 6,752,928 B2 | 6/2004 | Pfeil et al. |
| 6,758,810 B2 | 7/2004 | Lebel et al. |
| 6,758,975 B2 | 7/2004 | Peabody et al. |
| 6,768,425 B2 | 7/2004 | Flaherty et al. |
| 6,787,032 B2 | 9/2004 | Kurome et al. |
| 6,790,198 B1 | 9/2004 | White et al. |
| 6,804,656 B1 | 10/2004 | Rosenfeld et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,811,707 B2 | 11/2004 | Rovatti et al. |
| 6,813,519 B2 | 11/2004 | Lebel et al. |
| 6,820,093 B2 | 11/2004 | De La Huerga |
| 6,854,088 B2 | 2/2005 | Massengale et al. |
| 6,861,033 B2 | 3/2005 | Mullins et al. |
| 6,868,309 B1 | 3/2005 | Begelman |
| 6,871,211 B2 | 3/2005 | Labounty et al. |
| 6,873,268 B2 | 3/2005 | Lebel et al. |
| 6,880,034 B2 | 4/2005 | Manke et al. |
| 6,885,288 B2 | 4/2005 | Pincus |
| 6,902,670 B2 | 6/2005 | Ho |
| 6,908,546 B2 | 6/2005 | Smith |
| 6,912,549 B2 | 6/2005 | Rotter et al. |
| 6,913,590 B2 | 7/2005 | Sorenson et al. |
| 6,923,987 B2 | 8/2005 | Kai et al. |
| 6,928,452 B2 | 8/2005 | De La Huerga |
| 6,950,708 B2 | 9/2005 | Bowman, IV et al. |
| 6,958,705 B2 | 10/2005 | Lebel et al. |
| 6,960,179 B2 | 11/2005 | Gura |
| 6,974,437 B2 | 12/2005 | Lebel et al. |
| 6,976,628 B2 | 12/2005 | Krupa |
| 6,979,306 B2 | 12/2005 | Moll |
| 6,980,958 B1 | 12/2005 | Surwit et al. |
| 6,986,872 B2 | 1/2006 | Taylor |
| 7,024,245 B2 | 4/2006 | Lebel et al. |

(56) References Cited

U.S. PATENT DOCUMENTS

| | | |
|---|---|---|
| 7,039,878 B2 | 5/2006 | Auer et al. |
| 7,044,927 B2 | 5/2006 | Mueller et al. |
| 7,045,061 B2 | 5/2006 | Nishimura et al. |
| 7,051,002 B2 | 5/2006 | Keresman, III et al. |
| 7,061,831 B2 | 6/2006 | De La Huerga |
| 7,072,769 B2 | 7/2006 | Fletcher-Haynes et al. |
| 7,076,520 B2 | 7/2006 | Nelson et al. |
| 7,077,956 B2 | 7/2006 | Rovatti |
| 7,089,780 B2 | 8/2006 | Sunshine et al. |
| 7,092,796 B2 | 8/2006 | Vanderveen |
| 7,096,072 B2 | 8/2006 | Engleson et al. |
| 7,108,790 B2 | 9/2006 | Collins et al. |
| 7,117,239 B1 | 10/2006 | Hansen |
| 7,122,210 B2 | 10/2006 | Paola |
| 7,152,469 B2 | 12/2006 | Milleker et al. |
| 7,156,808 B2 | 1/2007 | Quy |
| 7,161,484 B2 | 1/2007 | Tsoukalis |
| 7,165,221 B2 | 1/2007 | Monteleone et al. |
| 7,171,274 B2 | 1/2007 | Starkweather et al. |
| 7,188,151 B2 | 3/2007 | Kumar et al. |
| 7,194,336 B2 | 3/2007 | DiGianfilippo et al. |
| 7,208,092 B2 | 4/2007 | Micheli |
| 7,216,802 B1 | 5/2007 | De La Huerga |
| 7,231,263 B2 | 6/2007 | Choi |
| 7,238,156 B1 | 7/2007 | Adamczyk |
| 7,241,272 B2 | 7/2007 | Karoor et al. |
| 7,250,619 B2 | 7/2007 | Taylor et al. |
| 7,251,610 B2 | 7/2007 | Alban et al. |
| 7,264,148 B2 | 9/2007 | Tachibana |
| 7,274,799 B2 | 9/2007 | Cohen et al. |
| 7,275,220 B2 | 9/2007 | Brummel et al. |
| 7,290,680 B2 | 11/2007 | Henry et al. |
| 7,292,141 B2 | 11/2007 | Staats et al. |
| 7,300,418 B2 | 11/2007 | Zaleski |
| 7,304,582 B2 | 12/2007 | Robert et al. |
| 7,306,736 B2 | 12/2007 | Collins et al. |
| 7,308,894 B2 | 12/2007 | Hickle |
| 7,309,323 B2 | 12/2007 | Gura et al. |
| 7,315,825 B2 | 1/2008 | Rosenfeld et al. |
| 7,316,648 B2 | 1/2008 | Kelly et al. |
| 7,316,662 B2 | 1/2008 | Delnevo et al. |
| 7,317,967 B2 | 1/2008 | DiGianfilippo et al. |
| 7,319,386 B2 | 1/2008 | Collins, Jr. et al. |
| 7,321,862 B2 | 1/2008 | Rosenfeld et al. |
| 7,343,224 B2 | 3/2008 | DiGianfilippo et al. |
| 7,347,819 B2 | 3/2008 | Lebel et al. |
| 7,356,382 B2 | 4/2008 | Vanderveen |
| 7,369,913 B2 | 5/2008 | Heminway et al. |
| 7,383,196 B1 | 6/2008 | Tang et al. |
| 7,384,410 B2 | 6/2008 | Eggers et al. |
| 7,419,587 B2 | 9/2008 | Valbjoern et al. |
| 7,419,597 B2 | 9/2008 | Brugger et al. |
| 7,544,300 B2 | 6/2009 | Brugger et al. |
| 7,749,393 B2 | 7/2010 | Brugger et al. |
| 7,805,407 B1 | 9/2010 | Verbeke |
| 7,892,423 B2 | 2/2011 | Rohde et al. |
| 7,942,851 B2 | 5/2011 | Fairies et al. |
| 7,976,711 B2 | 7/2011 | Brugger et al. |
| 8,071,055 B2 | 12/2011 | Newcombe |
| 8,177,977 B2 | 5/2012 | Gaignet |
| 8,192,387 B2 | 6/2012 | Brugger et al. |
| 8,216,452 B2 | 7/2012 | Rohde et al. |
| 8,226,595 B2 | 7/2012 | Childers et al. |
| 8,354,029 B2 | 1/2013 | Hank |
| 8,425,767 B2 | 4/2013 | Fava et al. |
| 9,053,033 B1 * | 6/2015 | Derbeko .............. G06F 12/06 |
| 9,180,238 B2 | 11/2015 | Bedingfield et al. |
| 9,860,302 B2 | 1/2018 | Wittner et al. |
| 9,934,540 B2 | 4/2018 | Schneider et al. |
| 2001/0001237 A1 | 5/2001 | Stroda et al. |
| 2001/0003177 A1 | 6/2001 | Schena et al. |
| 2001/0007053 A1 | 7/2001 | Bardy |
| 2001/0007932 A1 | 7/2001 | Kamen et al. |
| 2001/0011153 A1 | 8/2001 | Bardy |
| 2001/0016699 A1 | 8/2001 | Burbank et al. |
| 2001/0017817 A1 | 8/2001 | De La Huerga |
| 2001/0021801 A1 | 9/2001 | Bardy |
| 2001/0021817 A1 | 9/2001 | Brugger et al. |
| 2001/0025138 A1 | 9/2001 | Bardy |
| 2001/0025156 A1 | 9/2001 | Bui et al. |
| 2001/0027289 A1 | 10/2001 | Treu et al. |
| 2001/0027634 A1 | 10/2001 | Hebron et al. |
| 2001/0028308 A1 | 10/2001 | De La Huerga |
| 2001/0030234 A1 | 10/2001 | Wiklof |
| 2001/0031944 A1 | 10/2001 | Peterson et al. |
| 2001/0032101 A1 | 10/2001 | Statius Muller |
| 2001/0034502 A1 | 10/2001 | Moberg et al. |
| 2001/0034616 A1 | 10/2001 | Giannini |
| 2001/0037057 A1 | 11/2001 | Bardy |
| 2001/0037079 A1 | 11/2001 | Burbank et al. |
| 2001/0037083 A1 | 11/2001 | Hartlaub et al. |
| 2001/0037217 A1 | 11/2001 | Abensour et al. |
| 2001/0037220 A1 | 11/2001 | Merry et al. |
| 2001/0041892 A1 | 11/2001 | Burbank et al. |
| 2001/0041920 A1 | 11/2001 | Starkweather et al. |
| 2001/0042441 A1 | 11/2001 | Purdom et al. |
| 2001/0044588 A1 | 11/2001 | Mault |
| 2001/0044731 A1 | 11/2001 | Coffman et al. |
| 2001/0051764 A1 | 12/2001 | Bardy |
| 2001/0053885 A1 | 12/2001 | Gielen et al. |
| 2002/0002326 A1 | 1/2002 | Causey, III et al. |
| 2002/0002473 A1 | 1/2002 | Schrier et al. |
| 2002/0004645 A1 | 1/2002 | Carlisle et al. |
| 2002/0010568 A1 | 1/2002 | Rubbert et al. |
| 2002/0013612 A1 | 1/2002 | Whitehurst |
| 2002/0016567 A1 | 2/2002 | Hochman et al. |
| 2002/0016568 A1 | 2/2002 | Lebel et al. |
| 2002/0016719 A1 | 2/2002 | Nemeth et al. |
| 2002/0016722 A1 | 2/2002 | Kameda |
| 2002/0019606 A1 | 2/2002 | Lebel et al. |
| 2002/0019748 A1 | 2/2002 | Brown |
| 2002/0022776 A1 | 2/2002 | Bardy |
| 2002/0025796 A1 | 2/2002 | Taylor et al. |
| 2002/0026104 A1 | 2/2002 | Bardy |
| 2002/0029157 A1 | 3/2002 | Marchosky |
| 2002/0029776 A1 | 3/2002 | Blomquist |
| 2002/0032602 A1 | 3/2002 | Lanzillo, Jr. et al. |
| 2002/0038392 A1 | 3/2002 | De La Huerga |
| 2002/0040208 A1 | 4/2002 | Flaherty et al. |
| 2002/0044043 A1 | 4/2002 | Chaco et al. |
| 2002/0046062 A1 | 4/2002 | Kameda |
| 2002/0046185 A1 | 4/2002 | Villart et al. |
| 2002/0046346 A1 | 4/2002 | Evans |
| 2002/0052539 A1 | 5/2002 | Haller et al. |
| 2002/0052542 A1 | 5/2002 | Bardy |
| 2002/0052574 A1 | 5/2002 | Hochman et al. |
| 2002/0065540 A1 | 5/2002 | Lebel et al. |
| 2002/0067273 A1 | 6/2002 | Jaques et al. |
| 2002/0068015 A1 | 6/2002 | Polaschegg et al. |
| 2002/0072718 A1 | 6/2002 | Brugger et al. |
| 2002/0072733 A1 | 6/2002 | Flaherty |
| 2002/0077852 A1 | 6/2002 | Ford et al. |
| 2002/0077865 A1 | 6/2002 | Sullivan |
| 2002/0082480 A1 | 6/2002 | Riff et al. |
| 2002/0082865 A1 | 6/2002 | Bianco et al. |
| 2002/0082868 A1 | 6/2002 | Pories et al. |
| 2002/0084904 A1 | 7/2002 | De La Huerga |
| 2002/0087120 A1 | 7/2002 | Rogers et al. |
| 2002/0099283 A1 | 7/2002 | Christ et al. |
| 2002/0099301 A1 | 7/2002 | Bardy |
| 2002/0100762 A1 | 8/2002 | Liff et al. |
| 2002/0107476 A1 | 8/2002 | Mann et al. |
| 2002/0107707 A1 | 8/2002 | Naparstek et al. |
| 2002/0116509 A1 | 8/2002 | De La Huerga |
| 2002/0128606 A1 | 9/2002 | Cowan et al. |
| 2002/0128871 A1 | 9/2002 | Adamson et al. |
| 2002/0128880 A1 | 9/2002 | Kunikiyo |
| 2002/0131332 A1 | 9/2002 | Kaelin |
| 2002/0133377 A1 | 9/2002 | Brown |
| 2002/0140675 A1 | 10/2002 | Ali et al. |
| 2002/0143254 A1 | 10/2002 | Maruyama |
| 2002/0156462 A1 | 10/2002 | Stultz |
| 2002/0158128 A1 | 10/2002 | Ashiura |
| 2002/0162778 A1 | 11/2002 | Peabody et al. |

(56) References Cited

U.S. PATENT DOCUMENTS

| | | |
|---|---|---|
| 2002/0165491 A1 | 11/2002 | Reilly |
| 2002/0169636 A1 | 11/2002 | Eggers et al. |
| 2002/0187940 A1 | 12/2002 | Masuda et al. |
| 2002/0198513 A1 | 12/2002 | Lebel et al. |
| 2003/0000876 A1 | 1/2003 | Kawaguchi |
| 2003/0023177 A1 | 1/2003 | Bardy |
| 2003/0036783 A1 | 2/2003 | Bauhahn et al. |
| 2003/0050621 A1 | 3/2003 | Lebel et al. |
| 2003/0052787 A1 | 3/2003 | Zerhusen et al. |
| 2003/0060753 A1 | 3/2003 | Starkweather et al. |
| 2003/0060754 A1 | 3/2003 | Reilly |
| 2003/0060765 A1 | 3/2003 | Campbell et al. |
| 2003/0060768 A1 | 3/2003 | Kiyatake |
| 2003/0065287 A1 | 4/2003 | Spohn et al. |
| 2003/0078534 A1 | 4/2003 | Hochman et al. |
| 2003/0083901 A1 | 5/2003 | Bosch et al. |
| 2003/0088238 A1 | 5/2003 | Poulsen et al. |
| 2003/0097092 A1 | 5/2003 | Flaherty |
| 2003/0105424 A1 | 6/2003 | Karoor et al. |
| 2003/0114836 A1 | 6/2003 | Estes et al. |
| 2003/0125611 A1 | 7/2003 | Bardy |
| 2003/0135250 A1 | 7/2003 | Lauman et al. |
| 2003/0139701 A1 | 7/2003 | White et al. |
| 2003/0140929 A1 | 7/2003 | Wilkes et al. |
| 2003/0141368 A1 | 7/2003 | Pascual et al. |
| 2003/0144878 A1 | 7/2003 | Wilkes et al. |
| 2003/0144880 A1 | 7/2003 | Talachian et al. |
| 2003/0144881 A1 | 7/2003 | Talachian et al. |
| 2003/0144882 A1 | 7/2003 | Talachian et al. |
| 2003/0154108 A1 | 8/2003 | Fletcher-Haynes et al. |
| 2003/0160683 A1 | 8/2003 | Blomquist |
| 2003/0163088 A1 | 8/2003 | Blomquist |
| 2003/0163223 A1 | 8/2003 | Blomquist |
| 2003/0163789 A1 | 8/2003 | Blomquist |
| 2003/0167035 A1 | 9/2003 | Flaherty et al. |
| 2003/0176933 A1 | 9/2003 | Lebel et al. |
| 2003/0181851 A1 | 9/2003 | Mann et al. |
| 2003/0182164 A1 | 9/2003 | Shabot et al. |
| 2003/0195397 A1 | 10/2003 | Bardy |
| 2003/0201697 A1 | 10/2003 | Richardson |
| 2003/0204414 A1 | 10/2003 | Wilkes et al. |
| 2003/0204416 A1 | 10/2003 | Radpay et al. |
| 2003/0204419 A1 | 10/2003 | Wilkes et al. |
| 2003/0204420 A1 | 10/2003 | Wilkes et al. |
| 2003/0212379 A1 | 11/2003 | Bylund et al. |
| 2003/0220605 A1 | 11/2003 | Bowman et al. |
| 2003/0220609 A1 | 11/2003 | Childers et al. |
| 2003/0225596 A1 | 12/2003 | Richardson et al. |
| 2003/0225728 A1 | 12/2003 | Moura |
| 2004/0010425 A1 | 1/2004 | Wilkes et al. |
| 2004/0039260 A1 | 2/2004 | Bardy |
| 2004/0039264 A1 | 2/2004 | Bardy |
| 2004/0039456 A1 | 2/2004 | Davlin et al. |
| 2004/0051368 A1 | 3/2004 | Caputo et al. |
| 2004/0088374 A1 | 5/2004 | Webb et al. |
| 2004/0111293 A1 | 6/2004 | Firanek et al. |
| 2004/0116862 A1 | 6/2004 | Ray |
| 2004/0117215 A1 | 6/2004 | Marchosky |
| 2004/0121767 A1 | 6/2004 | Simpson et al. |
| 2004/0167465 A1 | 8/2004 | Mihai et al. |
| 2004/0172283 A1 | 9/2004 | Vanderveen et al. |
| 2004/0172300 A1 | 9/2004 | Mihai et al. |
| 2004/0172301 A1 | 9/2004 | Mihai et al. |
| 2004/0172302 A1 | 9/2004 | Martucci et al. |
| 2004/0176667 A1 | 9/2004 | Mihai et al. |
| 2004/0193328 A1 | 9/2004 | Zaitsu et al. |
| 2004/0204673 A1 | 10/2004 | Flaherty |
| 2004/0215490 A1 | 10/2004 | Duchon et al. |
| 2004/0220829 A1 | 11/2004 | Baharav et al. |
| 2004/0235446 A1 | 11/2004 | Flaherty et al. |
| 2004/0260233 A1 | 12/2004 | Garibotto et al. |
| 2005/0038680 A1 | 2/2005 | McMahon |
| 2005/0054923 A1 | 3/2005 | Pan |
| 2005/0065817 A1 | 3/2005 | Mihai et al. |
| 2005/0070767 A1 | 3/2005 | Maschke |
| 2005/0071194 A1 | 3/2005 | Bormann et al. |
| 2005/0080651 A1 | 4/2005 | Morrison et al. |
| 2005/0101901 A1 | 5/2005 | Gura |
| 2005/0102028 A1 | 5/2005 | Arnin et al. |
| 2005/0102167 A1 | 5/2005 | Kapoor |
| 2005/0131340 A1 | 6/2005 | Sorenson et al. |
| 2005/0131741 A1 | 6/2005 | Tang et al. |
| 2005/0133449 A1 | 6/2005 | Sternby |
| 2005/0135306 A1 | 6/2005 | McAllen et al. |
| 2005/0137573 A1 | 6/2005 | McLaughlin |
| 2005/0139651 A1 | 6/2005 | Lim et al. |
| 2005/0143671 A1 | 6/2005 | Hastings et al. |
| 2005/0148890 A1 | 7/2005 | Hastings |
| 2005/0171815 A1 | 8/2005 | Vanderveen |
| 2005/0177096 A1 | 8/2005 | Bollish et al. |
| 2005/0177395 A1 | 8/2005 | Blomquist |
| 2005/0201345 A1 | 9/2005 | Williamson |
| 2005/0228693 A1 | 10/2005 | Webb et al. |
| 2005/0231374 A1 | 10/2005 | Diem et al. |
| 2005/0234381 A1 | 10/2005 | Niemetz et al. |
| 2005/0246416 A1 | 11/2005 | Blomquist |
| 2005/0267780 A1 | 12/2005 | Ray et al. |
| 2005/0278194 A1 | 12/2005 | Holland et al. |
| 2005/0283385 A1 | 12/2005 | Hunkeler et al. |
| 2006/0015015 A1 | 1/2006 | Kawamoto et al. |
| 2006/0167722 A1 | 1/2006 | Struys et al. |
| 2006/0064020 A1 | 3/2006 | Burnes et al. |
| 2006/0064053 A1 | 3/2006 | Bollish et al. |
| 2006/0065713 A1 | 3/2006 | Kingery |
| 2006/0089539 A1 | 4/2006 | Miodownik et al. |
| 2006/0089854 A1 | 4/2006 | Holland et al. |
| 2006/0089855 A1 | 4/2006 | Holland et al. |
| 2006/0100907 A1 | 5/2006 | Holland et al. |
| 2006/0106647 A1 | 5/2006 | Brummel et al. |
| 2006/0106649 A1 | 5/2006 | Eggers et al. |
| 2006/0116639 A1 | 6/2006 | Russell |
| 2006/0129435 A1 | 6/2006 | Smitherman et al. |
| 2006/0143051 A1 | 6/2006 | Eggers et al. |
| 2006/0149591 A1 | 7/2006 | Hanf et al. |
| 2006/0173713 A1 | 8/2006 | Petro et al. |
| 2006/0190302 A1 | 8/2006 | Eggers et al. |
| 2006/0200369 A1 | 9/2006 | Batch et al. |
| 2006/0206356 A1 | 9/2006 | Vanderveen |
| 2006/0211994 A1 | 9/2006 | Roman et al. |
| 2006/0229551 A1 | 10/2006 | Martinez et al. |
| 2006/0247606 A1 | 11/2006 | Batch |
| 2006/0253301 A1 | 11/2006 | Simms et al. |
| 2006/0258985 A1 | 11/2006 | Russell |
| 2006/0259327 A1 | 11/2006 | Hoag |
| 2006/0277070 A1 | 12/2006 | Hungerford et al. |
| 2007/0033073 A1 | 2/2007 | Tajaliawal et al. |
| 2007/0073266 A1 | 3/2007 | Chmiel et al. |
| 2007/0073787 A1 | 3/2007 | Tysowski et al. |
| 2007/0083386 A1 | 4/2007 | Chuang et al. |
| 2007/0083390 A1 | 4/2007 | Gorup et al. |
| 2007/0088578 A1 | 4/2007 | Hoffman et al. |
| 2007/0112297 A1 | 5/2007 | Plahey et al. |
| 2007/0124002 A1 | 5/2007 | Estes et al. |
| 2007/0129983 A1 | 6/2007 | Scherpbier et al. |
| 2007/0135866 A1 | 6/2007 | Baker et al. |
| 2007/0156452 A1 | 7/2007 | Batch |
| 2007/0158268 A1 | 7/2007 | DeComo |
| 2007/0163965 A1 | 7/2007 | Wolfe |
| 2007/0179807 A1 | 8/2007 | Nessinger et al. |
| 2007/0185738 A1 | 8/2007 | Anuszewski et al. |
| 2007/0197878 A1 | 8/2007 | Shklarski |
| 2007/0198293 A1 | 8/2007 | Ash et al. |
| 2007/0203753 A1 | 8/2007 | Hasan et al. |
| 2007/0214003 A1 | 9/2007 | Holland et al. |
| 2007/0233035 A1 | 10/2007 | Wehba et al. |
| 2007/0233049 A1 | 10/2007 | Wehba et al. |
| 2007/0233050 A1 | 10/2007 | Wehba et al. |
| 2007/0233281 A1 | 10/2007 | Wehba et al. |
| 2007/0233520 A1 | 10/2007 | Wehba et al. |
| 2007/0233521 A1 | 10/2007 | Wehba et al. |
| 2007/0255126 A1 | 11/2007 | Moberg et al. |
| 2007/0265879 A1 | 11/2007 | Charlson et al. |
| 2007/0276328 A1 | 11/2007 | Childers et al. |
| 2007/0276869 A1 | 11/2007 | Charlson et al. |

(56) References Cited

U.S. PATENT DOCUMENTS

| | | |
|---|---|---|
| 2007/0278155 A1 | 12/2007 | Lo et al. |
| 2007/0293817 A1 | 12/2007 | Feng et al. |
| 2008/0015493 A1 | 1/2008 | Childers et al. |
| 2008/0015895 A1 | 1/2008 | Charlson et al. |
| 2008/0021741 A1 | 1/2008 | Holla et al. |
| 2008/0033360 A1 | 2/2008 | Evans et al. |
| 2008/0033749 A1 | 2/2008 | Blomquist |
| 2008/0034323 A1 | 2/2008 | Blomquist |
| 2008/0045877 A1 | 2/2008 | Levin et al. |
| 2008/0045932 A1 | 2/2008 | Beau et al. |
| 2008/0052317 A1 | 2/2008 | Francis et al. |
| 2008/0059239 A1 | 3/2008 | Gerst et al. |
| 2008/0076969 A1 | 3/2008 | Kraft et al. |
| 2008/0077436 A1 | 3/2008 | Muradia |
| 2008/0091466 A1 | 4/2008 | Butler et al. |
| 2008/0097912 A1 | 4/2008 | Dicks et al. |
| 2008/0097913 A1 | 4/2008 | Dicks et al. |
| 2008/0097914 A1 | 4/2008 | Dicks et al. |
| 2008/0103554 A1 | 5/2008 | Dicks et al. |
| 2008/0114292 A1 | 5/2008 | Rasch-Menges et al. |
| 2008/0126969 A1 | 5/2008 | Blomquist |
| 2008/0133265 A1 | 6/2008 | Silkaitis et al. |
| 2008/0143515 A1 | 6/2008 | Wood et al. |
| 2008/0161754 A1 | 7/2008 | Marano-Ford |
| 2008/0177222 A1 | 7/2008 | Roger |
| 2008/0203023 A1 | 8/2008 | Burbank et al. |
| 2008/0208111 A1 | 8/2008 | Kamen et al. |
| 2008/0210606 A1 | 9/2008 | Burbank |
| 2008/0230450 A1 | 9/2008 | Burbank et al. |
| 2008/0233925 A1* | 9/2008 | Sun .......... H04L 67/12 340/572.1 |
| 2008/0287919 A1 | 11/2008 | Kimball |
| 2008/0318678 A1* | 12/2008 | Stivoric .......... G16B 99/00 463/36 |
| 2009/0008318 A1 | 1/2009 | Anes et al. |
| 2009/0008331 A1 | 1/2009 | Wilt et al. |
| 2009/0012655 A1 | 1/2009 | Kienman et al. |
| 2009/0045121 A1 | 2/2009 | Kabayama et al. |
| 2009/0099552 A1 | 4/2009 | Levy et al. |
| 2009/0218285 A1 | 9/2009 | Hank |
| 2010/0010427 A1* | 1/2010 | Yu .......... B01D 61/32 604/29 |
| 2010/0018923 A1 | 1/2010 | Rohde et al. |
| 2010/0051546 A1 | 3/2010 | Vuong et al. |
| 2010/0078092 A1 | 4/2010 | Weilhoefer et al. |
| 2010/0137693 A1 | 6/2010 | Porras et al. |
| 2010/0326916 A1 | 12/2010 | Wrazel et al. |
| 2010/0332149 A1 | 12/2010 | Scholpp |
| 2011/0072422 A1 | 3/2011 | Brauer |
| 2011/0100913 A1 | 5/2011 | Minami et al. |
| 2011/0163034 A1* | 7/2011 | Castellarnau ....... A61M 1/1609 210/646 |
| 2011/0180480 A1 | 7/2011 | Kloeffel et al. |
| 2011/0186521 A1 | 8/2011 | Burbank et al. |
| 2011/0192796 A1 | 8/2011 | Smejtek et al. |
| 2011/0208160 A1 | 8/2011 | Wu et al. |
| 2011/0315611 A1 | 12/2011 | Fulkerson et al. |
| 2013/0006666 A1* | 1/2013 | Schneider .......... G16H 10/60 705/3 |
| 2013/0008854 A1 | 1/2013 | Wallace et al. |
| 2013/0053651 A1* | 2/2013 | Tarn .......... B01D 61/32 600/301 |
| 2013/0062265 A1 | 3/2013 | Balschat et al. |
| 2013/0066661 A1 | 3/2013 | Biebesheimer et al. |
| 2013/0197929 A1 | 8/2013 | Vanderveen et al. |
| 2013/0245611 A1 | 9/2013 | Bonnet et al. |
| 2013/0281965 A1 | 10/2013 | Kamen et al. |
| 2013/0317753 A1* | 11/2013 | Kamen .......... A61B 5/0022 600/595 |
| 2013/0336814 A1 | 12/2013 | Kamen et al. |
| 2014/0047263 A1 | 2/2014 | Coatney et al. |
| 2014/0195257 A1* | 7/2014 | Perkins .......... G16H 40/20 705/2 |
| 2014/0238912 A1 | 8/2014 | Vincent |
| 2014/0324464 A1* | 10/2014 | Carlsgaard .......... G16H 10/60 705/2 |
| 2015/0041531 A1* | 2/2015 | Vavala .......... A61M 5/142 235/375 |
| 2015/0067021 A1 | 3/2015 | Protas et al. |
| 2015/0127733 A1* | 5/2015 | Ding .......... H04W 4/70 709/204 |
| 2017/0203022 A1 | 7/2017 | Burbank et al. |

FOREIGN PATENT DOCUMENTS

| | | |
|---|---|---|
| DE | 20 02 033 | 8/1970 |
| DE | 29 01 628 | 7/1980 |
| DE | 31 22 756 | 6/1982 |
| DE | 33 07 830 | 6/1984 |
| DE | 34 42 744 | 6/1986 |
| DE | 40 03 452 | 8/1991 |
| DE | 42 08 054 | 10/1992 |
| DE | 41 22 754 | 1/1993 |
| DE | 198 14 695 | 10/1999 |
| DE | 19828923 | 1/2000 |
| DE | 19849787 | 2/2000 |
| DE | 198 54 338 | 6/2000 |
| DE | 19814695 | 9/2001 |
| EP | 0 058 325 | 8/1982 |
| EP | 0 064 393 | 10/1982 |
| EP | 64393 | 11/1982 |
| EP | 0 106 026 | 4/1984 |
| EP | 0 143 340 | 6/1985 |
| EP | 0 143 341 | 6/1985 |
| EP | 152717 | 8/1985 |
| EP | 0 171 550 | 2/1986 |
| EP | 0 233 848 | 8/1987 |
| EP | 0306211 | 3/1989 |
| EP | 0 318 993 | 6/1989 |
| EP | 0 350 675 | 1/1990 |
| EP | 0 373 455 | 6/1990 |
| EP | 0 222 709 | 5/1991 |
| EP | 0428505 | 5/1991 |
| EP | 0432138 | 6/1991 |
| EP | 0243547 | 7/1991 |
| EP | 0 490 212 | 6/1992 |
| EP | 0491183 | 6/1992 |
| EP | 0 501 144 | 9/1992 |
| EP | 0 560 368 | 9/1993 |
| EP | 0402505 | 12/1993 |
| EP | 0 587 251 | 3/1994 |
| EP | 0611228 | 8/1994 |
| EP | 0 720 856 | 7/1996 |
| EP | 0 722 744 | 7/1996 |
| EP | 0498382 | 11/1996 |
| EP | 0778033 | 11/1996 |
| EP | 0 749 328 | 12/1996 |
| EP | 0 776 222 | 6/1997 |
| EP | 0 826 3 84 | 3/1998 |
| EP | 0 826 383 | 3/1998 |
| EP | 0575512 | 5/1998 |
| EP | 0928615 | 7/1999 |
| EP | 0956876 | 11/1999 |
| EP | 980685 | 2/2000 |
| EP | 0659092 | 10/2000 |
| EP | 0 659 091 | 12/2000 |
| EP | 1 097 724 | 5/2001 |
| EP | 0847769 | 8/2001 |
| EP | 1 277 485 | 1/2003 |
| EP | 1614437 | 1/2006 |
| EP | 1894586 | 3/2008 |
| EP | 2180908 | 5/2010 |
| FR | 2 397 197 | 2/1979 |
| FR | 2 585 251 | 1/1987 |
| GB | 1 408 319 | 10/1975 |
| GB | 2 014 060 | 8/1979 |
| GB | 1 554 810 | 10/1979 |
| GB | 2 061 755 | 5/1981 |
| GB | 2122509 | 1/1984 |
| GB | 2124511 | 2/1984 |
| GB | 2 212 739 | 8/1989 |
| GB | 2282244 | 3/1995 |
| GR | 3 026 703 | 7/1998 |

(56) References Cited

FOREIGN PATENT DOCUMENTS

| | | |
|---|---|---|
| JP | 55-32384 | 3/1980 |
| JP | 55-45437 | 3/1980 |
| JP | 55-122559 | 9/1980 |
| JP | 57161511 | 10/1982 |
| JP | 61-25564 | 2/1986 |
| JP | 6-143074 | 6/1986 |
| JP | S61143074 | 6/1986 |
| JP | 4-2060 | 1/1992 |
| JP | 92002060 | 1/1992 |
| JP | 4348757 | 3/1992 |
| JP | 4-384757 | 12/1992 |
| JP | 59-029264 | 2/1994 |
| JP | 7-299455 | 11/1995 |
| JP | 07-299455 | 11/1995 |
| JP | 8-29224 | 2/1996 |
| JP | 8029224 | 2/1996 |
| JP | 96029224 | 2/1996 |
| JP | 9-327511 | 12/1997 |
| JP | 9327511 | 12/1997 |
| JP | 10085324 | 4/1998 |
| JP | H1085324 | 4/1998 |
| JP | 11-137672 | 5/1999 |
| JP | 11137672 | 5/1999 |
| JP | 2000-217908 | 8/2000 |
| JP | 2000-296318 | 10/2000 |
| JP | 200120483 | 12/2000 |
| JP | 2001-270856 | 10/2001 |
| JP | 2003047657 | 2/2003 |
| JP | 2003-513714 | 4/2003 |
| JP | 2008181358 | 8/2008 |
| JP | 2009510566 | 3/2009 |
| JP | 2011-172961 | 8/2011 |
| JP | 2012519547 | 8/2012 |
| JP | 2014520593 | 8/2014 |
| SE | 1012918 | 3/1981 |
| SE | 1344362 | 6/1984 |
| SU | 1001945 | 3/1983 |
| WO | 9014850 | 12/1990 |
| WO | 1992 018048 | 10/1992 |
| WO | 94/15099 | 7/1994 |
| WO | 9420158 | 9/1994 |
| WO | 95/02559 | 1/1995 |
| WO | 95/17597 | 6/1995 |
| WO | 95/35124 | 12/1995 |
| WO | 9625214 | 8/1996 |
| WO | 9640318 | 12/1996 |
| WO | 97/09074 | 3/1997 |
| WO | 97/47337 | 6/1997 |
| WO | 98/17333 | 4/1998 |
| WO | 98/22165 | 5/1998 |
| WO | 98/23353 | 6/1998 |
| WO | 98/32477 | 7/1998 |
| WO | 99/03519 | 1/1999 |
| WO | 99/06082 | 2/1999 |
| WO | 99/42150 | 8/1999 |
| WO | 9964103 | 12/1999 |
| WO | 9966407 | 12/1999 |
| WO | 00/09182 | 2/2000 |
| WO | 00/20050 | 4/2000 |
| WO | 00/20052 | 4/2000 |
| WO | 00/31967 | 6/2000 |
| WO | 00/50143 | 8/2000 |
| WO | 0055762 | 9/2000 |
| WO | 00/57925 | 10/2000 |
| WO | 00/57926 | 10/2000 |
| WO | 00/57927 | 10/2000 |
| WO | 00/57928 | 10/2000 |
| WO | 00/64510 | 11/2000 |
| WO | 01/37786 | 5/2001 |
| WO | 01/37894 | 5/2001 |
| WO | 01/37895 | 5/2001 |
| WO | 01/37900 | 5/2001 |
| WO | 01/41831 | 6/2001 |
| WO | 01/41832 | 6/2001 |
| WO | 01/41833 | 6/2001 |
| WO | 01/42758 | 6/2001 |
| WO | 01/45769 | 6/2001 |
| WO | 01/47576 | 7/2001 |
| WO | 02/43859 | 6/2002 |
| WO | 2004070562 | 8/2004 |
| WO | 2007118235 | 10/2007 |
| WO | 2008138311 | 11/2008 |
| WO | 2011069110 | 6/2011 |
| WO | 2012120078 | 9/2012 |
| WO | 2012129501 | 9/2012 |
| WO | 2012170961 | 12/2012 |
| WO | 2013068393 | 5/2013 |
| WO | 2014203023 | 12/2014 |

OTHER PUBLICATIONS

European Search Report—EP Application No. 16176496 dated Mar. 21, 2017—13 pages.
European Communication—EP Application No. 09710209.9 dated Mar. 20, 2015—6 pages.
Search and Examination Report dated Jul. 29, 2014 for related GB Appl. No. 1322331.8.
Office Action for Mexican Patent Application No. MX/a/2010/008961.
International Search Report for PCT/US2017/031405 dated Sep. 26, 2017—7 pages.
Written Opinion of the International Searching Authority for PCT/US2017/031405 dated Sep. 26, 2017—13 pages.
International Search Report for PCT/US2017/031400 dated Sep. 26, 2017—7 pages.
Written Opinion of the International Search Authority for PCT/US2017/031400 dated Sep. 26, 2017—14 pages.
International Search Report for PCT/US2017/031396 dated Jul. 27, 2017—6 pages.
Written Opinion of the International Search Authority for PCT/US2017/031396 dated Jul. 27, 2017—7 pages.
U.S. Appl. No. 15/195,801, filed Jun. 28, 2016.
International Search Report and Written Opinion for International Application No. PCT/US2009/046997 dated Feb. 16, 2010.
International Search Report for corresponding International Application PCT/US2009/031809 dated Oct. 19, 2009.
Written Opinion for corresponding International Application PCT/US2009/031809 dated Oct. 19, 2009.
Japanese Office Action dated Dec. 14, 2012 for related Application No. 2011-100145—corresponding communication indicates no references cited in JP Office Action (1 page).
Fresenius 90/2 Peritoneal Therapy Cycler, Articile, written by Fresenius SA, dated Jul. 1993—6 pages.
Japanese Office Action for Japanese Application No. 2011-100145.
Japanese Office Action dated Feb. 18, 2014 for related Japanese Appln. No. 2013-051434.
International Preliminary Report on Patentability for PCT/EP2016/064392 dated Dec. 26, 2017—1 page.
International-Type Search Report for ITS/SE15/00154 dated Jan. 5, 2016—5 pages.
International Search Report issued in International Patent Application No. PCT/EP2016/064392 dated Sep. 14, 2016.
Written Opinion issued in International Patent Application No. PCT/EP2016/064392 dated Sep. 14, 2016.
Martins et al., "Survey of data replication in P2P systems," Institut National de Recherche en Informatique et en Automatique INRIA, N 6083 Dec. 2006—version 2, Feb. 7, 2007—45 pages—XP002501325.
Chinese Office Action Appl. No. 2016800373131 dated Jun. 23, 2021.
Chinese Search Report Appl. No. 2016800373131 dated Jun. 23, 2021.
Japanese Office Action Application No. 2021-015123 dated May 6, 2022—8 pages.

* cited by examiner

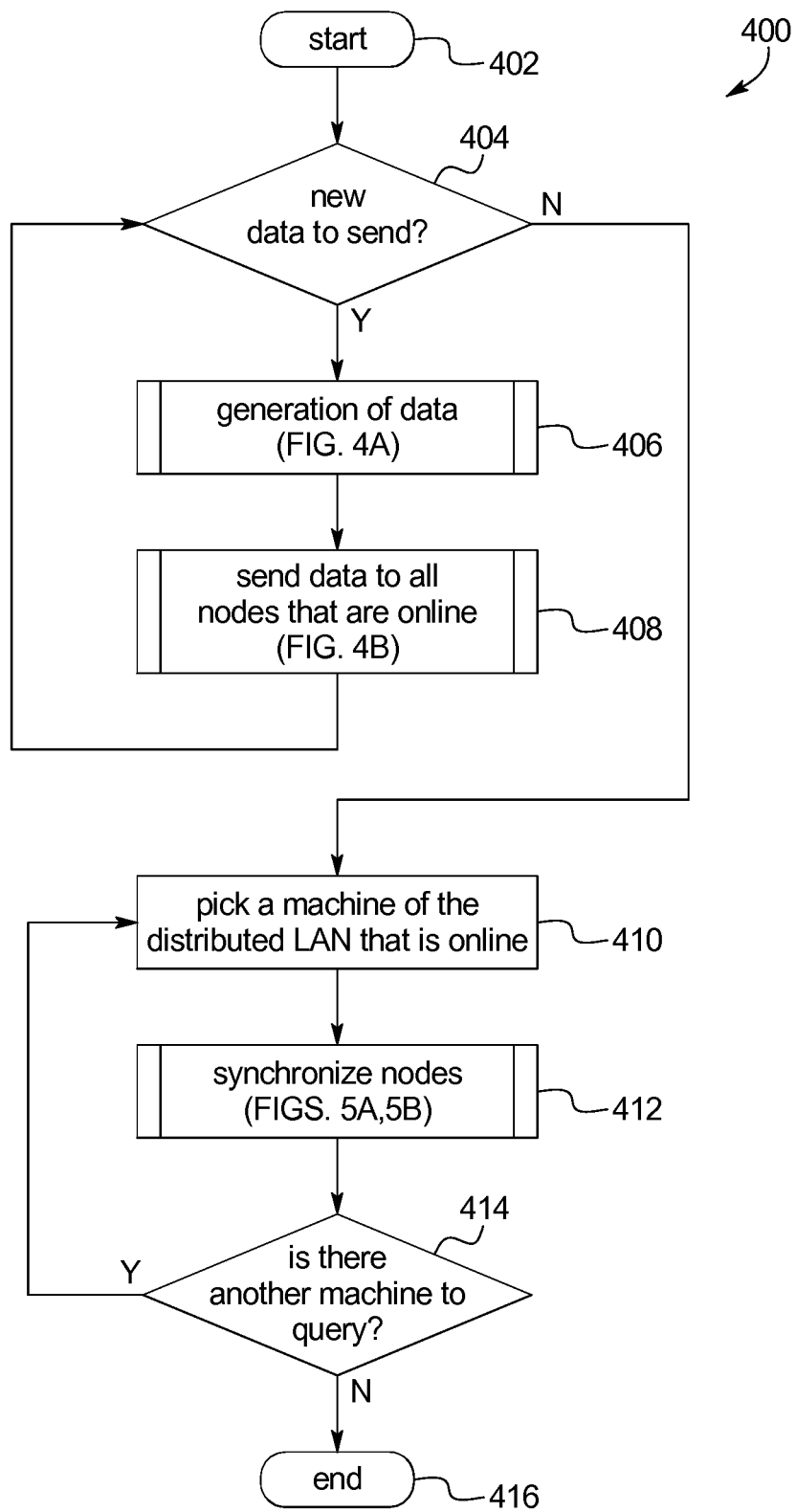

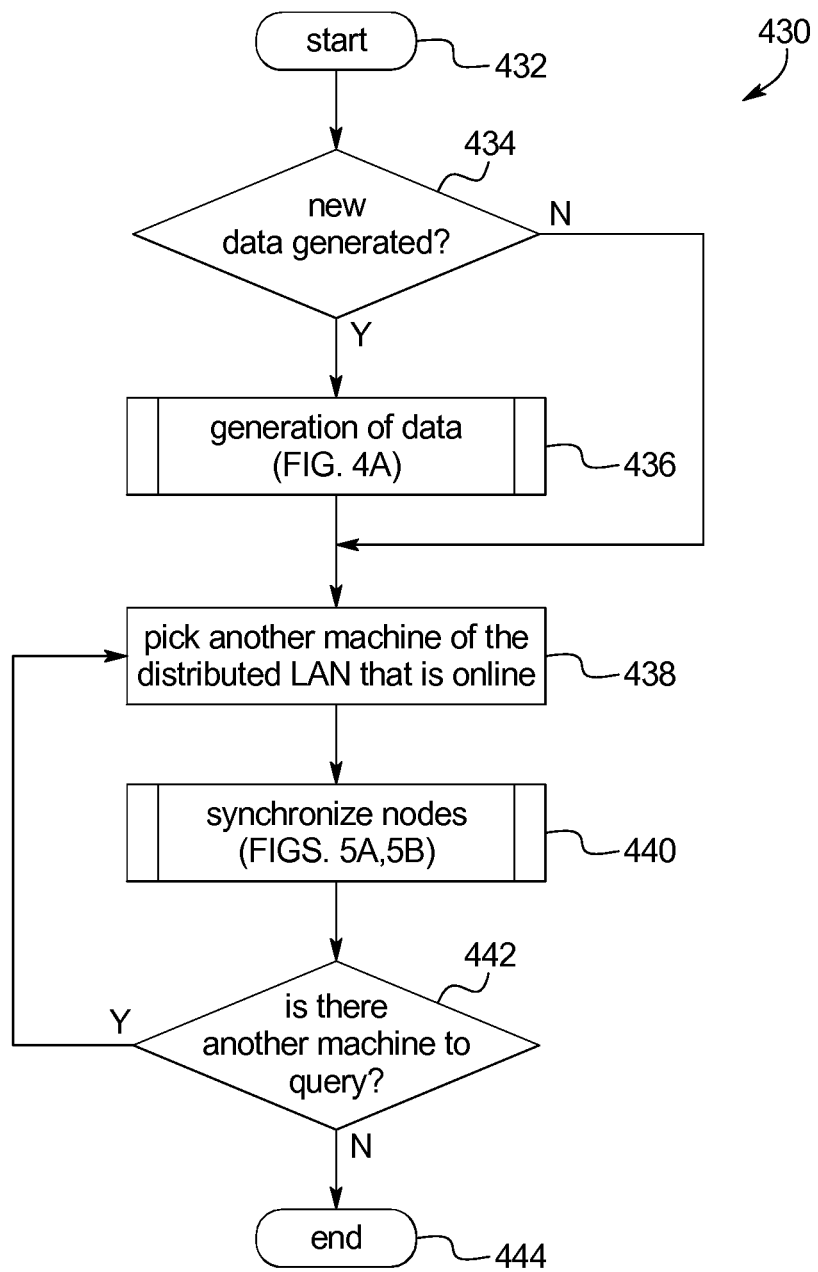

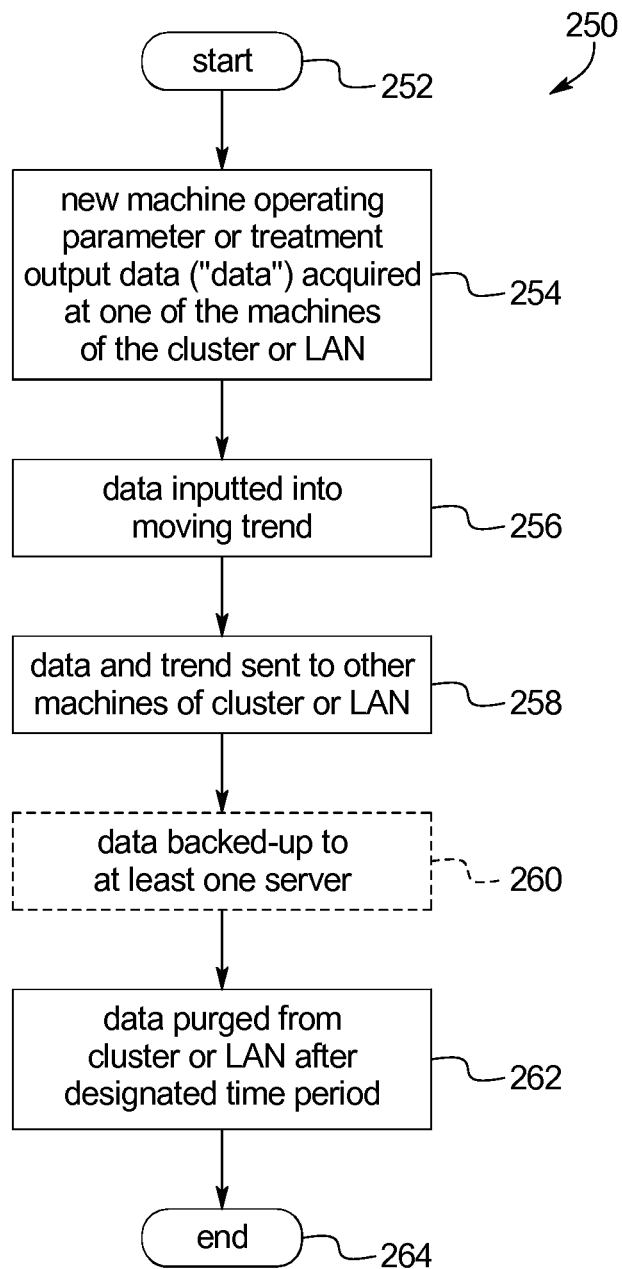

MEDICAL DEVICE SYSTEM AND METHOD HAVING A DISTRIBUTED DATABASE

PRIORITY CLAIM

The present application is a National Phase of International Application No. PCT/EP2016/064392, filed on Jun. 22, 2016, which claims priority to Swedish Patent Application No. 1550885-6, filed on Jun. 25, 2015, the entire contents of each of which are being incorporated herein by reference.

BACKGROUND

The present disclosure relates generally to computer networks. More specifically, the present disclosure relates to computer networks for medical devices that pump fluids.

Hemodialysis ("HD") in general uses diffusion to remove waste products from a patient's blood. A diffusive gradient that occurs across the semi-permeable dialyzer between the blood and an electrolyte solution called dialysate causes diffusion. Hemofiltration ("HF") is an alternative renal replacement therapy that relies on a convective transport of toxins from the patient's blood. This therapy is accomplished by adding substitution or replacement fluid to the extracorporeal circuit during treatment (typically ten to ninety liters of such fluid). The substitution fluid and the fluid accumulated by the patient in between treatments is ultrafiltered over the course of the HF treatment, providing a convective transport mechanism, which is particularly beneficial in removing middle and large molecules (in hemodialysis there is a small amount of waste removed along with the fluid gained between dialysis sessions, however, the solute drag from the removal of that ultrafiltrate is typically not enough to provide convective clearance).

Hemodiafiltration ("HDF") is a treatment modality that combines convective and diffusive clearances. HDF flows dialysate through a dialyzer, similar to standard hemodialysis, providing diffusive clearance. In addition, substitution solution is provided directly to the extracorporeal circuit, providing convective clearance.

The above modalities are provided by a dialysis machine. The machines can be provided in a center or in a patient's home. Dialysis machines provided in a center are used multiple times a day for multiple patients. Prescription input data is inputted into the dialysis machines before treatment, while treatment output data is collected from the dialysis machines during and after treatment. The data is useful to the clinic to track how the patient's treatment is proceeding over time, so that the treatment can be modified if needed. The data is also useful to see how a particular machine is performing. For example, if the data indicates that a particular machine is alarming for the same reason over multiple treatments with different patients, the clinic may determine that the problem is with the machine, not the patients. The data is also useful as a basis for billing and reimbursement purposes. The data can track how many different drugs or solutions (e.g., heparin or saline) and disposables are consumed over a treatment, so that the clinic can then bill and be reimbursed for the proper amount for the materials consumed.

It is known to install centralized servers that collect treatment data from multiple dialysis machines over multiple treatments. The drawbacks that the central servers present are many. First, the central servers result in significant hardware and installation costs. Second, the central servers require a good deal of computer experience to install and maintain. Many clinics simply do not have the information technology ("IT") support for the centralized data systems. These drawbacks in many cases result in the clinics not using automated data collection systems and instead collecting the data manually, which is time consuming and error prone. For example, many backend software systems handle dialysis related information, disconnected from the dialysis machines, manually and far from the point of care in both space and time, which is time consuming and prone to failure. It would be advantageous if this and other types of data collection could be performed closer to the machine and the treatment.

A need accordingly exists for an improved data network system for medical devices.

SUMMARY

The present disclosure provides a distributed database system and method for medical devices, such as a renal failure therapy system and method that performs hemodialysis ("HD"), hemofiltration ("HF"), hemodiafiltration ("HDF"), peritoneal dialysis ("PD"), isolated UF ("UF") and continuous renal replacement therapy ("CRRT"), slow continuous ultrafiltration ("SCUF"), continuous veno-venous hemodialysis ("CVVHD"), continuous veno-venous hemofiltration ("CVVH"), and continuous veno-venous hemodiafiltration ("CVVHDF"). Accordingly, "renal failure therapy" as used herein is meant to include any one, or more, or all of HD, HF, HDF, PD, UF, and CRRT (including SCUF, CVVHD, CVVH, and CVVHDF versions of CRRT). The present disclosure focuses primarily on renal failure therapy systems but is not limited to them. The network system and method described herein applies to other medical devices, such as, drug delivery pumps (including intravenous ("IV") pumps, syringe pumps, large volume pumps ("LVP's"), shuttle pumps, peristaltic IV pumps, and any combination thereof, for example), and apheresis machines.

In one primary embodiment, the distributed database system of the present disclosure includes a local area network ("LAN") formed between multiple renal failure therapy machines located in a clinic or other group setting or cluster, wherein the distributed database system does not need to interface with a centralized server, database, backbone network, or wide area network ("WAN") of the clinic. Indeed, the network of the distributed database system can be the backbone network of the clinic. The distributed database system is stand-alone and all of the functionality to host the system can be provided within each dialysis machine. Each renal failure therapy machine has a control processor that operates with a memory device, which in turn communicates with the distributed database system via cable or wirelessly.

It should be appreciated that while one primary embodiment of the distributed database system uses a LAN having a network router, it is not necessary for the LAN to use such a router. Instead, the LAN could alternatively be a different type of network, such as an ad-hoc network or a power line network. As used herein, LAN includes network router types, Ethernet types, wireless types, ad-hoc types, power line types, others known to those of skill, others developed in the future, and combinations thereof.

The machines of the distributed database system can each access the same medically related data in one embodiment, where medically related data includes but is not limited to (i) prescription input parameters or data (e.g., machine operating parameters), (ii) treatment output data (e.g., UF removed, total blood volume moved, total dialysis fluid volume consumed, heparin volume consumed, alarms, and treatment effectiveness measurements Kt/V, etc.), (iii) technical input data (e.g., calibrations, alarm limits, etc.), (iv) technical output data (e.g., actual component usage, sensor measurements, etc.), and (v) administrative data (e.g., inventory data and staffing data). In general, data (i) and (ii) are helpful to evaluate a patient's treatment over time, while data (iii) and (iv) are helpful to evaluate how a particular machine is performing. Data (v) helps the clinic to run smoothly and efficiently.

Prescription input parameters can also include any and all fluid flowrate, pressure alarm limits, volume, temperature, conductivity, dose, treatment time, etc., settings used during the one or more treatments performed on any machine of the distributed database system. Prescription input parameters can further include any drugs that the patient is supposed to take and any supplies that the patient is supposed to use in connection with treatment, e.g., any medical delivery drug, anticoagulant such as heparin, saline, Erythropoietin stimulating agent ("ESA") such as Epogen™, iron supplements, potassium supplements, bicarbonate used, acid concentrate used, dialyzer used, etc.

Treatment output data can also be any and all sensed or recorded data, e.g., actual fluid flowrate, pressure, treatment fluid volume, temperature conductivity, dialysis or drug delivery dose, treatment time, UF volume, etc., actually achieved during a treatment performed on a machine of the distributed database system. Treatment output data can further include any alarms or alerts generated during the treatment. Still further, treatment output data can include any physiological data, such as blood pressure, patient temperature, patient weight, patient glucose level, as well as subjective feelings such as nauseousness, light-headedness, sleepiness, etc., recorded during the treatment (including any physiological data sensed by the machine (e.g., a dialysis or drug delivery machine) or at one or more remote sensing equipment).

Each machine can broadcast medically related data to the other machines on the distributed database system. And as discussed below, an operator can use any machine of the distributed database system to obtain information regarding any patient of the clinic and the status of any other machine. It should be appreciated however that each machine of distributed database system does not have to have access to all the data of the system, or to the same data as each other machine, allowing for the machines or groups of the machines to instead have access to less than all the medically related data of the system.

The the distributed database system uses the fact that even very large amounts of memory storage are relatively inexpensive. The the distributed database system accordingly copies at least part of data of the machines on some periodic basis, or in real time, such that each machine has the same, or virtually the same, data stored in its memory device. If in real time, the distributed database system may be limited to distributing only certain types of data so that ongoing treatments are not interrupted. For example, the machines may be limited to only distributing alarm information so that a nurse attending to a patient at a first machine can see at the first machine that an alarm is occurring at a second machine. In the example, the machines can later, after the treatments are completed, exchange their bulk treatment output data.

Real time data sharing is alternatively more extensive, such that a nurse or clinician at a first machine can obtain treatment data concerning other machines of the distributed database system. For example, it is contemplated to provide a clinician's summary screen that allows a clinician to quickly view the status of all ongoing treatments. For example, a main treatment screen of the medical device can provide a "clinic summary" button that when pressed takes the clinician to the clinician's summary screen. Once at that screen, the clinician can quickly see real time or the current day's information about each other machine of the distributed database system, such as, current state of the machine (e.g., running, paused, under alarm condition, or not in use), elapsed treatment time, time of treatment remaining, amount of UF collected, and alarm history, and the like.

The system can provide multiple summary screens. For example, a main treatment screen of the medical device can provide a "summary" button, which when pressed leads the user to a screen having multiple summary buttons, such as the "clinic summary" button, a "patient summary" button, a "stock keeping summary" button, a "staffing summary" button, for example. The "patient summary" button when pressed could lead to a list of patients (for all of the clinic or only those currently undergoing treatment), wherein pressing any patient name on the list leads to a screen dedicated to that patient. Thus the nurse or clinician can reach a dedicated patient screen from any machine in the distributed database system. The "stock keeping summary" button when pressed could lead to a stock summary screen listing supply names, how many of each is supply in stock and how many of each supply is on back order. The "staffing summary" button when pressed could lead to a "staffing summary" screen listing all clinicians, nurses and doctors associated with the clinic, and which ones are currently at the clinic, their shift times, their technical specialties, and the like.

The "stock summary" and "staffing summary" screens are good examples of how different machines or other equipment connected to the distributed database system do not all have to share the same data. Here, one or more backend computer may be used to update the stock summary and/or the staffing summary information, e.g., at the end of each day. The one or more backend computer can share its updated stock summary and/or staffing summary information with each machine of the distributed database system, however, the one or more backend computer does not need to have access to the other types of medically related data listed above, which is provided to and received from the machines.

The summary information may or may not be real time information. For example, the clinician summary screen may involve real time data transfer, e.g., of treatment output data for different patients being treated on the machines employing the distributed database system. Stock summary information on the other hand can be current but not necessarily up to the minute information. For example, the information is in one embodiment not updated immediately as a dialyzer is pulled from inventory, but updated instead at the end of the day, where the total number of dialyzers used during that day are subtracted from inventory.

In one embodiment, a user such as a nurse or clinician must enter identification to be authenticated and receive authorization to review any information of the distributed databases of the present disclosure, including the summary information just described. For example, the summary screens discussed above when selected first present user identification and password entry boxes. Only after entry of an authorized username and password can the requesting nurse or clinician see patient identifiable data.

In one embodiment, the renal failure therapy machines are of a plug-and-play type, so that the machines can connect to the distributed database system automatically and share data on the system without any (or very little) user setup or configuration. Besides sharing treatment data, the distributed database system of the present disclosure also shares or makes sure that each machine has and operates with the latest software. If a software update is provided on one of the machines, the machine if allowed by the clinic will be able to propagate the software update to all machines of the distributed database system. In an embodiment, software updates are performed at the end of the day while the machines are not performing treatment. In many cases, the machines at the end of the day go into a dormant, sleep, hibernation or offline mode or state ("hibernation state"). The machine with the software update will awaken any machines in the hibernation state, so that all machines of the distributed database system or cluster can receive the software updates.

In certain instances, a renal failure therapy machine of the distributed database system may be disconnected from the system, e.g., for mechanical service or updating, cleaning, etc. In such a case, when the disconnected machine is placed back online with the distributed database system, the machine is updated to store any missing operating software and treatment data, so that the machine is fully up to date with the other machines of the distributed database system or cluster.

The distributed database system may include machines of only a single type or manufacturer. Alternatively, the distributed database system or cluster can include medical devices of different types and/or manufacturers. For example, the distributed database system or cluster can include renal failure therapy machines provided by manufacturer X, Y, and Z. It is contemplated that adapters, intermediate computers or interfaces be provided so that machines provided by manufacturers Y and Z can (i) communicate with each other, and (ii) communicate with the machine of manufacturer X. The adapters, intermediate computers or interfaces also ensure that the machines of each of manufacturers X, Y, and Z have adequate processing and memory to receive the data updating discussed herein.

There are various fundamental modes contemplated for the machines of the distributed database system to share data. In a first fundamental mode, the machines "push" their newly acquired data out to the other machines. Here, the machines can take turns sending their data to the other machines of the distributed database system. In particular, the machines in one "push" embodiment take turns sending their patient or treatment data at the end of a designated time period, such as at the end of every second, minute, hour, shift or treatment day. For example, each machine of the distributed database system may be given a queue number, e.g., 1/10, 2/10, 3/10 . . . 10/10, assuming that there are ten machines in the distributed database system. When it comes time for the machines to share data, machine 1/10 sends its data to machines 2/10 to 10/10. When machine 1/10 is complete, machine 2/10 sends its data to machines 1/10, and 3/10 to 10/10, and so on until machine 10/10 sends its data to machines 1/10 to 9/10. In the end, all ten machines have the data from every other machine of the cluster.

In another "push" embodiment, one of the machines acts as a hub machine, while other machines of the distributed database system act as spokes. Here, one or more machine of the cluster, e.g., machine 1/10 receives the data from all other machines 2/10 to 10/10. Machines 2/10 to 10/10 can each send their respective data according to a sequence requested by hub machine 1/10. Hub machine 1/10 will then store the data from machines 2/10 to 10/10 in the order in which the data is sent to hub machine 1/10. Once hub machine 1/10 is fully updated with the data from all the other machines of the distributed database system or cluster, machine 1/10 sends out the totalled data, including machine 1/10's data to all other machines 2/10 to 10/10 in the distributed database system or cluster, which can again be according to a sequence requested by hub machine 1/10. Again, in the end, all ten machines should have the data from every other machine of the distributed database system.

Another fundamental mode in which the machines of the distributed database system share data is for each machine to "pull" any new data from all other machines of the system. Here, as opposed to pushing data, each machine of the distributed database system asks each other machine of the system whether it has any new data to deliver. To do so, the requesting machine can keep a record of which data each other machine has sent. The requesting machine tells the delivering machine which of the delivering machine's data has already been delivered. The delivering machine then looks to see if there is any additional data, and if so, the delivering machine delivers the new data to the requesting machine. Each machine of the distributed database system takes turns being the requesting machine, so that at the end of an exchange session, each machine is fully updated.

In a further fundamental mode, the machines can perform a "push-pull" routine to ensure that they share the same data. For example, a "push" routine can be performed to push new data out from each of the machines to each of the other machines of the distributed database system. The push can be performed for example when the new data is created or at a designated interval, e.g., once a day or shift. A "pull" routine can be used to compare the stored data of any two machines to make sure that they match. For example, when a machine comes back online to the distributed database system, it can perform a "pull" routine to capture any new data generated while offline by the other machines of the systems. "Pull" routines can also be performed periodically, e.g., daily or per shift. In a "pull" routine, two machines compare and pull data from each other and select the most recent data to make sure that the two machines in the end have the same most recent data. This "pull" routine takes place on some periodic basis between all pairs of the machines of the distributed database system. The premise here is that if all pairs of machines of a distributed database have the same data, then all machines of distributed database have the same data.

The "push" and the "push-pull" routines can be implemented in many different ways. For example, the "push" can be an accumulated push. Say, for example, that the distributed database system includes twelve machines, 1/12 to 12/12. If each machine does its own individual new data push, then there will be 11 pushes per machine multiplied by 12 machines, totalling 132 pushes. In another embodiment, each machine has a partner, say machines 1/12+2/12, 3/12+4/12, 5/12+6/12, 7/12+8/12, 9/12+10/12, and 11/12+12/12, creating six machine couples. Each couple requires twelve new data pushes, two individual pushes to each other, plus 10 more collective data pushes to each of the other machines outside the couple. Here, twelve data pushes per couple multiplied by six couples equals only 72 total data pushes. In a further embodiment, each machine works in a trio, say machines 1/12+2/12+3/12, 4/12+512/12+6/12, 7/12+8/12+9/12, and 10/12+11/12+12/12, creating four total trios. Each trio requires fifteen new data pushes, six individual pushes to each other, plus 9 more collective data pushes to each machine outside the trio. Here, fifteen data pushes per trio multiplied by four trios equals only 60 total data pushes. In this same manner, grouping the same twelve machines into three quartets again yields 60 total new data pushes (twenty new data pushes per quartet multiplied by three quartets). Interestingly, grouping the same twelve machines into two halves results in 72 total new data pushes (36 new data pushes per half multiplied by two halves). Thus, there may be an optimum one or more grouping (in terms of lesser data pushes being better) for any total number of machines in the distributed database.

To keep track of which data has been delivered, it is contemplated to assign the data, or a packet of data, with tag data or metadata. In an embodiment, the tag data or metadata includes a unique identifier ("id"), a hash sum, and a time stamp. The unique id identifies the particular machine and the sequence in the machine that a particular piece of new data (usually an array of data) is generated. The hash sum identifies or represents the actual content of the new data (e.g., array). The time stamp marks the time at which the new data was generated. When two machines are synchronized, the machines first look to see if they have each of each other's unique id's. If a unique identifier of machine X is missing in machine Y, the corresponding new data and all metadata are copied to machine Y, and vice versa. If any two unique id's match but the corresponding hash sums are different, then the hash sum with the most recent time stamp is selected for storage in each machine X and Y. In this manner if machine Y is taken offline or has been permanently hibernating for a number of days, machine Y upon returning can go through a synchronization procedure with each other machine of the distributed database system to retrieve any missing new data generated during the time that machine Y has been offline.

Discussed herein are methods for the machines of the distributed database system to periodically check the integrity of their shared data and to correct the data if it becomes corrupted. Similarly, methods are discussed herein for checking whether data has been transferred correctly from one machine to another. In both cases, the checking can be done via the comparison of hash sums calculated for one or more pieces of data.

In any of the embodiments discussed herein, the renal therapy machines or other types of medical machines of the distributed database system can send data and status information within or outside of the LAN for storage at a remote computer or network of the clinic, machine manufacturer or other desired entity. For example, the data can be remotely stored for the purposes of backup in case the LAN or other portion of the distributed database is damaged. The data can be archived remotely for analysis, e.g., for averaging, trending, supply chain analysis, or supply ordering analysis. The data can also be archived remotely to lessen or alleviate the data storage burden to the distributed database system. That is, it is contemplated for data that is over a certain age to be incorporated into ongoing trends kept for each patient on the distributed database system, archived remotely on a computer or network within or outside the LAN, and purged eventually from the machines of the distributed database system to free storage space for new patient data.

The distributed database system also supports connectivity to sensing equipment, such as sensors, monitors, analysers, other medical instruments, and lab equipment. For example, a weight scale provided in the clinic can be used to weigh each patient prior to and after treatment. Patient weight can be sent to each machine of the distributed database system, e.g., wired or wirelessly, because each machine keeps a record of the patient being weighed. Alternatively, patient weight can be sent, e.g., wirelessly, to the machine on which the patient is being treated that day, and then sent later after treatment from the specific machine to each machine of the distributed database system. Or, the patient weight can be stored on a data storage device, e.g., a flash drive, taken to the machine on which the patient is being treated that day, and then sent later after treatment from the specific machine to each machine of the distributed database system. Data from other sensors, such as, blood pressure measurement devices and glucose sensors can be recorded and distributed in the same way.

The distributed database system can also monitor the performance of the sensors, monitors, analysers, other medical instruments, and lab equipment and report if it appears that any of these appear to be giving false readings. For example, the system can have a backend computer that runs an algorithm analysing the data from each sensor, monitor, analyser, or other medical instrument. The algorithm can look for trends in the readings from the sensor, monitor, etc., for example, to look for sensing equipment that is tending to read patients higher or lower than normal. If such a piece of sensing equipment is identified, the backend computer sends a flag to each machine of the distributed database system, notifying the machines to either not accept readings from such sensing equipment and/or to flag a clinician to have the equipment recalibrated or replaced. It should therefore be appreciated that if a particular clinic uses two or more scales (or other sensors), the data sent from each scale or sensor can have an identifier identifying that piece of sensing equipment. Moreover, it is contemplated that if the system finds an improperly working piece of sensing equipment, e.g., weight scale or blood pressure module, the system can be programmed to look back to see if there has been similar corrupt data in the past from the particular piece of equipment. In any case, it is contemplated to connect any sensing equipment to the distributed database system of the present disclosure, so as to share data along with the medical fluid pumping deliveries.

A backend computer has been mentioned multiple times thus far. It is contemplated in an alternative embodiment for any one or more backend computer to be eliminated and its function to be performed instead in one or more of the medical machines of the distributed database system. For example, the functionality performed by the one or more backend computer used to update the stock summary and/or the staffing summary information discussed above, or the backend computer for the sensing equipment, may be provided instead by the processing and memory of one or more (or all) medical machines of the distributed database system. In this way, clinics with limited or no backend computing can enjoy the benefits described in connection with these backend computers. But, clinics that do have such backend computing can leverage such computing into the distributed database of the present disclosure. It is contemplated that the distributed database system of the present disclosure can operate (i) without any backend computing capability, (ii) with and compliment existing backend computing capability, or (iii) independently from existing backend computing capability.

The distributed database system also supports data transmission from its renal failure therapy or other medical machines to a mobile device or personal computer of a clinician, doctor, nurse or other authorized person. In an embodiment, a record of any transmission to an external mobile device or personal computer is maintained. In one embodiment, data stored in the distributed database system can be accessed (read) on a mobile device or remote personal computer, but not stored on the mobile device or remote personal computer, or transferred from those devices.

In light of the technical features set forth herein, and without limitation, in a first aspect, a medical device system includes: a distributed database; a plurality of medical devices operating with the distributed database; and a logic implementer associated with each medical device, wherein each logic implementer is programmed to access the distributed database, so that each medical device of system periodically (i) delivers at least one of prescription input parameters or treatment output data to and (ii) retrieves at least one of prescription input parameters or treatment output data from each of the other medical devices.

In a second aspect, which may be used with any other aspect described herein unless specified otherwise, the medical devices are in data communication with each other via a local area network ("LAN") used in connection with the distributed database.

In a third aspect, which may be used with any other aspect described herein unless specified otherwise, each of the medical devices is updated to store the same at least one of the prescription input parameters or treatment output data for each of a plurality of patients.

In a fourth aspect, which may be used with any other aspect described herein unless specified otherwise, the medical devices and the distributed database do not interact with a centralized server.

In a fifth aspect, which may be used with any other aspect described herein unless specified otherwise, the medical devices are provided by first and second manufacturers, and which includes an interface enabling the medical devices of the first and second manufacturers to communicate with one another.

In a sixth aspect, which may be used with any other aspect described herein unless specified otherwise, at least one of the (i) prescription input parameters or (ii) treatment output data is shared via the distributed database along with at least one other of (iii) technical input data, (iv) technical output data, or (v) administrative data.

In a seventh aspect, which may be used with any other aspect described herein unless specified otherwise, the distributed database also shares information from at least one medical equipment selected from the group consisting of: a weight scale, a blood pressure measurement device, a glucose sensor, a physiological sensor, an electrocardiogram device, water treatment equipment, a bed scale, an access disconnection device, a bioimpedance measurement device, a pH sensor, lab testing equipment, a blood sample analyzer, or an access flow measurement device.

In an eighth aspect, which may be used with any other aspect described herein unless specified otherwise, the distributed database is a first distributed database, and which includes a second distributed database that shares information from at least one medical equipment selected from the group consisting of: a weight scale, a blood pressure cuff, a glucose sensor, a physiological sensor, an electrocardiogram device, water treatment equipment, a bed scale, an access disconnection device, a bioimpedance measurement device, a pH sensor, lab testing equipment, a blood sample analyzer, or an access flow measurement device.

In a ninth aspect, which may be used with any other aspect described herein unless specified otherwise, periodically delivering and retrieving prescription input parameters or treatment output data includes doing so in at least one of: real time, a matter of seconds, a matter of minutes, hourly, daily, weekly, monthly, at an end of a treatment, at an end of a treatment day, or at an end of a treatment shift.

In a tenth aspect, which may be used with any other aspect described herein unless specified otherwise, at least one of the logic implementers is configured to periodically push at least one of the prescription input parameters or the treatment output data to each of the other medical devices of system.

In an eleventh aspect, which may be used with any other aspect described herein unless specified otherwise, at least one of the logic implementers is configured to periodically pull at least one of the prescription input parameters or the treatment output data from each of the other medical devices of system.

In a twelfth aspect, which may be used with any other aspect described herein unless specified otherwise, the system is further configured to share operating software between the medical devices via the distributed database.

In a thirteenth aspect, which may be used with any other aspect described herein unless specified otherwise, the distributed database is a first distributed database, and which includes a second distributed database, wherein at the logic implementer of at least one of the plurality of machines is programmed to access the second distributed database.

In a fourteenth aspect, which may be used with the thirteenth aspect in combination with any other aspect described herein unless specified otherwise, wherein one of the distributed databases is a real time data database.

In a fifteenth aspect, which may be used with the thirteenth aspect in combination with any other aspect described herein unless specified otherwise, one of the distributed databases is an administrative data database.

In a sixteenth aspect, which may be used with any other aspect described herein unless specified otherwise, each medical device of system is programmed to periodically verify its at least one prescription input parameters or treatment output data.

In a seventeenth aspect, which may be used with the sixteenth aspect in combination with any other aspect described herein unless specified otherwise, wherein verification is performed via a comparison of hash sums.

In an eighteenth aspect, which may be used with any other aspect described herein unless specified otherwise, the plurality of medical devices of system are programmed to periodically synchronize their at least one prescription input parameters or treatment output data.

In a nineteenth aspect, which may be used with the eighteenth aspect in combination with any other aspect described herein unless specified otherwise, synchronization is performed via a comparison of at least one of record identifications, hash sums, or time stamps.

In a twentieth aspect, which may be used with any other aspect described herein unless specified otherwise, at least one of the medical devices of system is programmed to display at least one summary screen showing at least one of the prescription input parameters or treatment output data for different medical devices of system.

In a twenty-first aspect, which may be used with any other aspect described herein unless specified otherwise, a medical device system includes: a plurality of medical devices; a first distributed database sharing first data generated or used by the plurality of medical devices amongst the plurality of medical devices; and a second distributed database sharing second data generated or used by the plurality of medical devices amongst the plurality of medical devices, (ii) second data generated or used by a second plurality of medical devices amongst the second plurality of medical devices, or (iii) second data generated or used by medical equipment.

In a twenty-second aspect, which may be used with the twenty-first aspect in combination with any other aspect described herein unless specified otherwise, one of the first medical devices and one of the second medical devices are configured to provide treatment to a same patient.

In a twenty-third aspect, which may be used with the twenty-first aspect in combination with any other aspect described herein unless specified otherwise, one of the first medical devices and one of the medical equipment are configured to provide treatment to a same patient.

In a twenty-fourth aspect, which may be used with the twenty-first aspect in combination with any other aspect described herein unless specified otherwise, the first medical devices are for providing treatment to a first group of patients and the second medical devices are for providing treatment to a second group of patients.

In a twenty-fifth aspect, which may be used with any other aspect described herein unless specified otherwise, a medical device includes: at least one medical fluid pump; and a logic implementer operating the at least one medical fluid pump so as to accept a pump input parameter and generate pump output data, the logic implementer programmed to (i) periodically share at least one of the pump input parameter or the pump output data with a plurality of other medical devices via a distributed database, and (ii) periodically receive at least one of a pump input parameter or pump output data from the plurality of other medical devices via the distributed database.

In a twenty-sixth aspect, which may be used with the twenty-fifth aspect in combination with any other aspect described herein unless specified otherwise, the logic implementer is programmed to synchronize at least one of the pump input parameter or the pump output data with the other medical devices via the distributed database.

In a twenty-seventh aspect, which may be used with the twenty-sixth aspect in combination with any other aspect described herein unless specified otherwise, the logic implementer is programmed to compare its own hash sum with a corresponding hash sum of one of the other medical devices to synchronize at least one of the pump input parameter or the pump output data with that other medical device.

In a twenty-eighth aspect, which may be used with the twenty-fifth aspect in combination with any other aspect described herein unless specified otherwise, the logic implementer is programmed to send a hash sum for at least one of the pump input parameter or the pump output data to one of the other medical devices for comparison at the other medical device with a corresponding hash sum of the other medical device.

In a twenty-ninth aspect, which may be used with the twenty-fifth aspect in combination with any other aspect described herein unless specified otherwise, the logic implementer is programmed to verify at least one of its pump input parameter or pump output data.

In a thirtieth aspect, which may be used with the twenty-ninth aspect in combination with any other aspect described herein unless specified otherwise, verification includes comparing a newly calculated hash sum with a previously established hash sum for at least one of the pump input parameter or the pump output data.

In a thirty-first aspect, which may be used with the second aspect in combination with any other aspect described herein unless specified otherwise, the LAN includes a network router.

In a thirty-second aspect, which may be used with the second aspect in combination with any other aspect described herein unless specified otherwise, the LAN is wired or wireless.

In a thirty-third aspect, which may be used with any other aspect described herein unless specified otherwise, the system of device is configured to create at least one treatment record trend from the medically related data.

In a thirty-fourth aspect, which may be used with any other aspect described herein unless specified otherwise, the system or device is configured to remove data at or after a certain age or for a regulatory reason.

In a thirty-fifth aspect, which may be used with any other aspect described herein unless specified otherwise, the system or device is which is configured to deliver the medically related data after each of the medical devices has completed treatment.

In a thirty-sixth aspect, which may be used with any other aspect described herein unless specified otherwise, the system or device is configured to deliver medically related data during treatment.

In a thirty-seventh aspect, which may be used with any other aspect described herein unless specified otherwise, the system or device is configured to awaken at least one of the medical devices from a hibernation mode for medically related data delivery.

In a thirty-eighth aspect, which may be used with any other aspect described herein unless specified otherwise, the system or device is configured to deliver multiple days of medically related data to one of the medical devices upon its returning to data communication with the other medical devices.

In a thirty-ninth aspect, which may be used with any other aspect described herein unless specified otherwise, the system or device is configured to update each medical device automatically with new software.

In a fortieth aspect, which may be used with any other aspect described herein unless specified otherwise, the system a medical device system includes: a plurality of medical devices in data communication with each other; and a logic implementer associated with each medical device, wherein each logic implementer is programmed to periodically store medically related data for each of a plurality of patients treated via the plurality of medical devices.

In a forty-first aspect, which may be used with any other aspect described herein unless specified otherwise, a medical device distributed database system includes: a local area network ("LAN"); and a plurality of medical devices in data communication with the LAN, wherein each of the plurality of medical devices periodically takes turns transferring medically related data via the LAN to each of the other medical devices.

In a forty-second aspect, which may be used with the forty-first aspect in combination with any other aspect described herein, each of the plurality of medical devices includes a place in a queue dictating an order in which the plurality of medical devices takes turns transferring medically related data.

In a forty-third aspect, which may be used with the forty-second aspect in combination with any other aspect described herein, the first medical device in the queue initiates the periodic transferring of data.

In a forty-fourth aspect, which may be used with the forty-first aspect in combination with any other aspect described herein, the transferring of data occurs after each day of treatment with the medical devices.

In a forty-fifth aspect, which may be used with the forty-first aspect in combination with any other aspect described herein, the transferring of data occurs during treatment with the medical devices.

In a forty-sixth aspect, which may be used with any other aspect described herein unless specified otherwise, a medical device distributed database system includes: a local area network ("LAN"); and a plurality of medical devices in data communication with the LAN, wherein a first one of the plurality of medical devices is programmed to periodically receive medically related data via the LAN from each of the other of the medical devices, and send the collective medically related data via the LAN to each of the other medical devices.

In a forty-seventh aspect, which may be used with the forty-sixth aspect in combination with any other aspect described herein, each of the other medical devices sends its data upon receiving a notice from the first medical device.

In a forty-eighth aspect, which may be used with the twenty-fifth aspect in combination with any other aspect described herein unless specified otherwise, the logic implementer is further programmed to share at least one of the pump input parameter or the pump output data with at least one of a personal communication device ("POD", 175), a personal computer (170), a server computer (180), or medical equipment (185) via the distributed database (10a to 10f).

In a forty-ninth aspect, which may be used with the twenty-fifth aspect in combination with any other aspect described herein unless specified otherwise, the logic implementer is further programmed to receive data from at least one of a personal communication device ("PCD", 175), a personal computer (170), a server computer (180), or medical equipment (185) via the distributed database (10a to 10f).

In a fiftieth aspect, any of the features, functionality and alternatives described in connection with any one or more of FIGS. 1A to 11 may be combined with any of the features, functionality and alternatives described in connection with any of the other one or more of FIGS. 1A to 11.

It is therefore an advantage of the present disclosure to provide a distributed database system and method for medical devices, which does not require a centralized server.

It is another advantage of the present disclosure to provide a distributed database system and method for medical devices, which enables any patient to use any machine of the system, wherein each machine will have a record of the patient.

It is a further advantage of the present disclosure to provide a distributed database system and method for medical devices, in which a clinician may approach any machine and obtain data about any patient within the distributed database system.

Moreover, it is an advantage of the present disclosure to provide a distributed database system and method for medical devices, which can handle different types and manufacturers of medical devices.

Additional features and advantages of the present invention are described in, and will be apparent from, the following Detailed Description of the Invention and the figures.

BRIEF DESCRIPTION OF THE FIGURES

FIG. 6A is a logic flow diagram illustrating one embodiment of a "push-pull" method employing the subroutines of FIGS. 4A, 4B and 5A (including FIG. 5B) to enable each machine of a distributed database system and method of the present disclosure to share data.

FIG. 6B is a logic flow diagram illustrating one embodiment of a "pull" method employing the subroutines of FIGS. 4A and 5A (including FIG. 5B) to enable each machine of a distributed database system and method of the present disclosure to share data.

FIG. 9 is a schematic representation of one embodiment for a life cycle for data stored on the distributed database system of the present disclosure.

DETAILED DESCRIPTION

Figure 10:
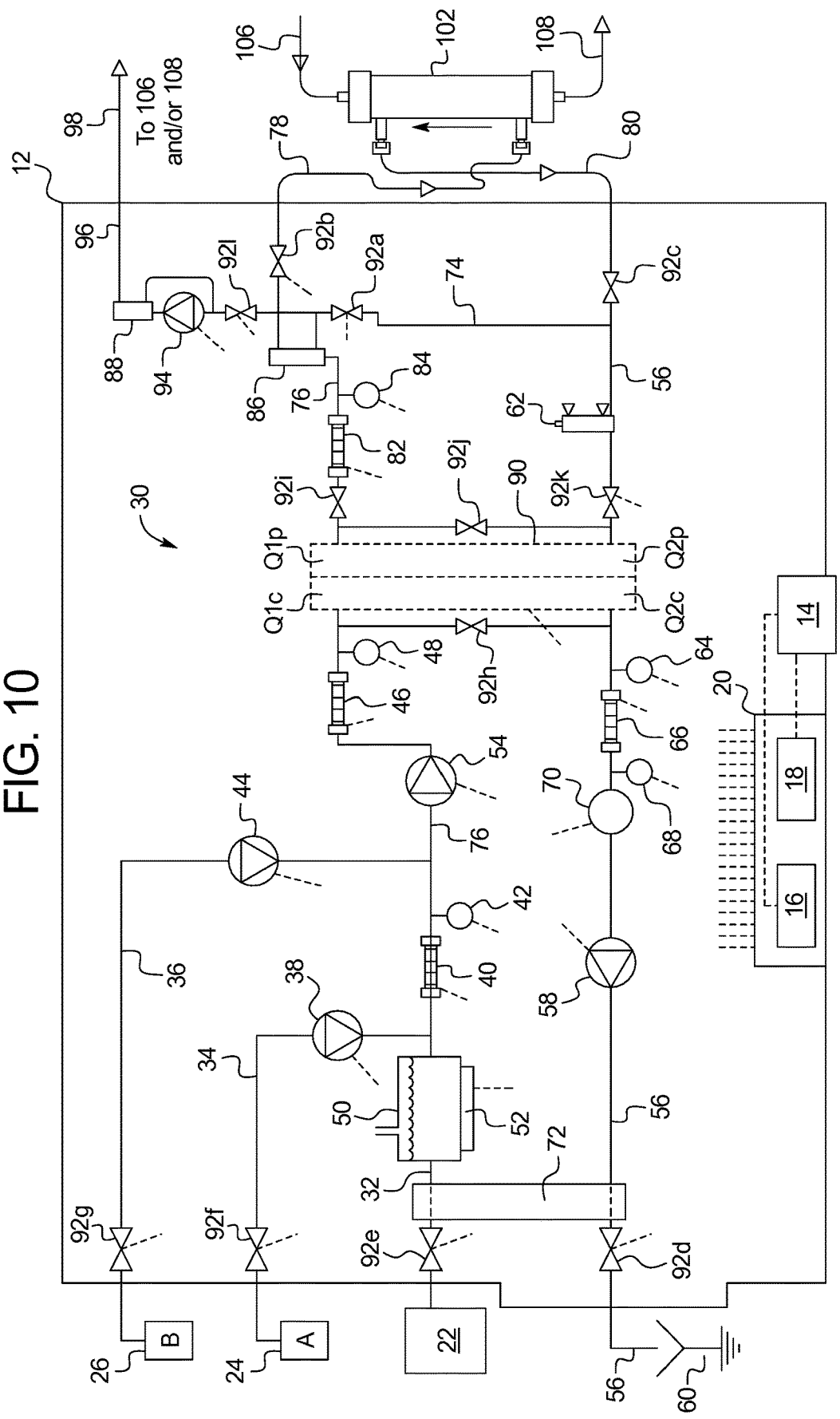
FIG. 10 is a flow schematic of one embodiment of a dialysate circuit of a renal failure therapy machine operable with the distributed database system and method of the present disclosure.
Figure 11:
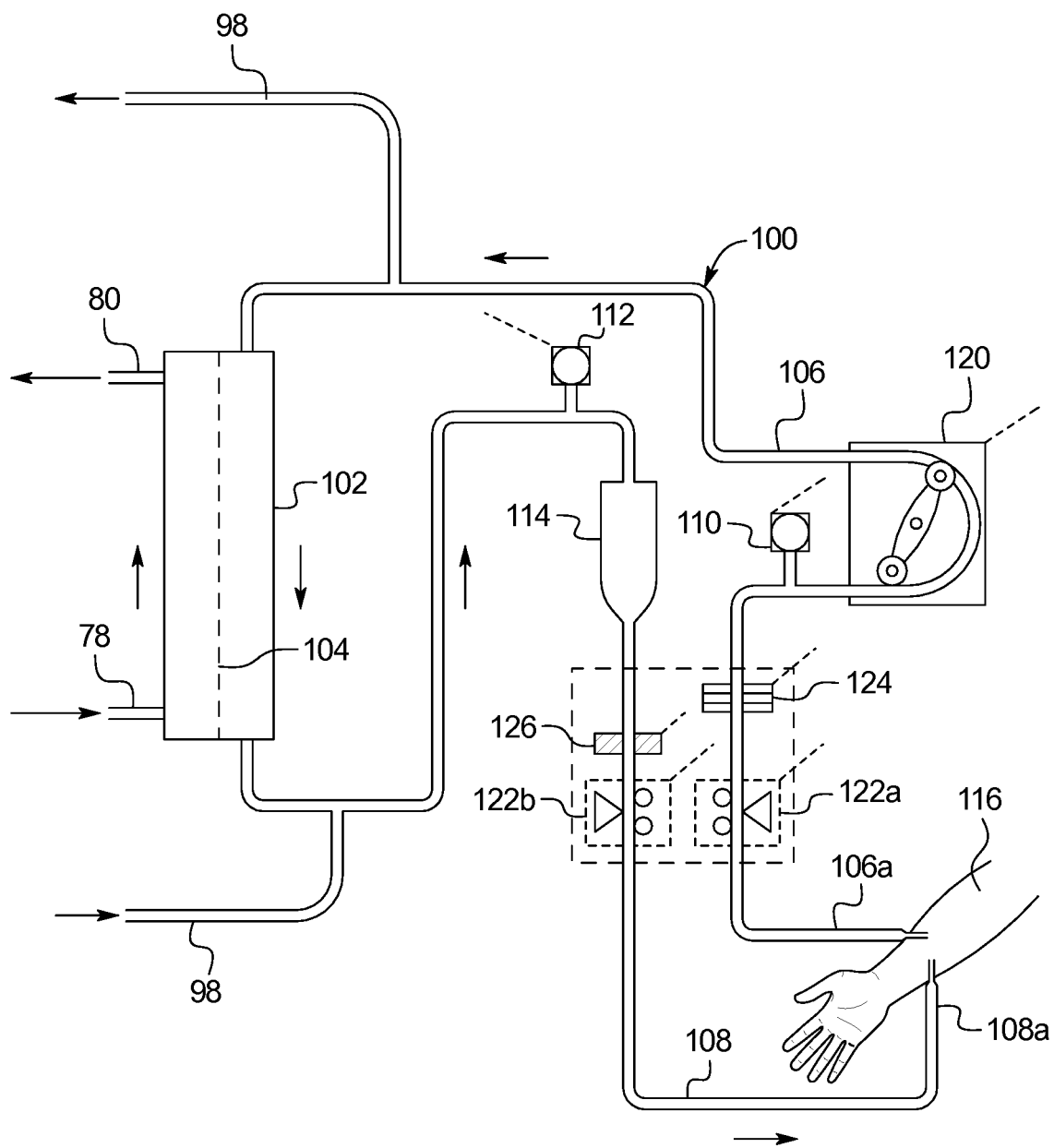
FIG. 11 is a flow schematic of one embodiment of a blood circuit of a renal failure therapy machine operable with the distributed database system and method of the present disclosure.

Referring now to the drawings and in particular to FIG. 1, an embodiment of a distributed database system 10 is illustrated. Distributed database system 10 includes plural medical devices 12*a* to 12*j* (referred to herein collectively as medical devices 12 or generally individually as medical device 12). Medical devices 12 can be any type of medical devices that can be grouped into a cluster, e.g., at a clinic, hospital, or other medical device setting. Medical devices 12 can for example be drug delivery or infusion pumps. Suitable infusion pumps for distributed database system 10 are described for example in copending U.S. Patent Publications 2013/0336814 (large volume peristaltic pump) and 2013/0281965 (syringe pump). In another embodiment, medical devices 12 are any type of renal failure therapy machine, such as a hemodialysis ("HD"), hemofiltration ("HF"), hemodiafiltration ("HDF"), continuous renal replacement therapy ("CRRT"), slow continuous ultrafiltration ("SCUF"), continuous veno-venous hemodialysis ("CVVHD"), continuous veno-venous hemofiltration ("CVVH"), continuous veno-venous hemodiafiltration ("CVVHDF") machine, and/or peritoneal dialysis ("PD"). FIGS. 10 and 11 below provide some context for how a renal failure therapy machine works, and in particular what type of data is needed to program the machine (machine prescription parameters), and what type of data the machine generates (treatment output data).

While distributed database system 10 is shown in FIG. 1 with medical devices 12*a* to 12*j*, it should be appreciated that any one or more of machines 12*a* to 12*j* or positions 12*a* to 12*j* can instead be a personal computer (such as computer 170 illustrated below), a server computer (such as server computer 180 illustrated below), or any type of sensing or other medical equipment (such as sensing equipment 185 illustrated below). Thus while medical fluid machines 12 are the predominant type of device sharing data on distributed database system 10, wherever medical fluid machines 12*a* to 12*j* or simply medical fluid machines 12 are referenced herein, those references are also meant to apply to personal computers 170, server computers 180 and sensing or other medical equipment 185.

Distributed database system 10 in one embodiment operates using a local area network ("LAN") 150. LAN 150 of system 10 ties together the cluster of machines 12*a* to 12*j*. Distributed database system 10 can include more or less than the illustrated ten machines. Distributed database system 10 does not require a server computer, an outside network, an intranet or an internet. Distributed database system 10 can be completely self-standing and located in areas with little or no internet capability and in facilities with little or no computer infrastructure. LAN 150 of distributed database system 10 connects to machines in a wired or wireless manner. FIG. 1 illustrates both scenarios. In a wired scenario, LAN 150 connects to machines 12*a* to 12*j* via a wired connection 152 at each machine. The wired connection can be of a Universal Serial Bus ("USB") variety or of another type, such as that of an Ethernet network, e.g., a standard IEEE 802.3 network.

In an alternative embodiment, LAN 150 is wireless. Here, each machine 12*a* to 12*j* is provided with a wireless transceiver 154, which (i) broadcasts information wirelessly to other machines of distributed database system 10 along LAN 150 and (ii) receives information wirelessly from other machines of the distributed database system 10 along LAN 150. The wireless network can be implemented as a Wi-Fi network, e.g., as set forth in standard IEEE 802.11. Any one of a variety of different Wi-Fi protocols can be used, e.g., type "a", "b", "g", "n", "ac" and other coming protocols, such as "af". Alternatively, protocols different from Wi-Fi may be used, such as Bluetooth or ZigBee.

In the example of FIG. 1, machines 12*a* to 12*d* and 12*f* to 12*j* of distributed database system 10 are all of the same type and manufacturer or are otherwise able to communicate directly with one another. Machines 12*a* to 12*d* and 12*f* to 12*j* are accordingly illustrated as communicating wired or wirelessly directly with one another. Machine 12*e* of distributed database system 10 on the other hand is not of the same manufacturer, the same model, or for whatever reason is not able to communicate directly with machines 12*a* to 12*d* and 12*f* to 12*j*. For example, different dialysis machine manufacturers, while generally requiring the same data input to run a treatment and generally generating the same treatment output data, will likely vary in terms of how the data is specifically inputted and generated. For example, while each dialysis machine will need to know treatment time, ultrafiltration ("UF") volume to be removed or UF goal, and UF flowrate, the three parameters are related and only two of the three need to be specified. One manufacturer may decide to input treatment time and UF goal and calculate UF flowrate, while another manufacturer may set UF goal and UF flowrate and calculate treatment time. In other examples, different manufacturers may input parameters and generate treatment data in different units, e.g., English standard versus metric units. Still further, different manufacturers may take into account different or additional parameters, e.g., fluid and food intake and volume of infused fluids during treatment for UF.

Different machine 12*e* illustrates one solution to the above-described manufacturer or machine type mismatch. An adapter, intermediate computer, or interface 160 is provided with different machine 12*e*. Here, LAN 150 is connected to intermediate interface 160 via wired connection 152 or wireless transceiver 154. A separate data line 156 and wired connection 158 can be made between intermediate interface 160 and machine 12*e*. Or, a separate wireless connection between transceivers 154 of machine 12*e* and intermediate interface 160 can be made to enable machine 12*e* to be in data communication with the other machines via LAN 150 indirectly.

Intermediate interface 160 may be provided with its own video screen 162, e.g., touch screen or onscreen touch keypad, and/or have its own electromechanical keyboard (not illustrated). Alternatively, intermediate interface 160 may simply be a data converter, wherein the user interacts with intermediate interface 160 via the user controls and video screen of different machine 12*e* (e.g., different manufacturer. While intermediate interface 160 is illustrated as a separate unit located in conjunction with the machine for which it operates, intermediate interface 160 is alternatively (i) one or more printed circuit board located within different machine 12*e*, (ii) one or more printed circuit board located within any of machines 12*a* to 12*d*, or 12*f* to 12*j*, or (iii) software loaded on a separate server 180 or computer 170 illustrated below in connection with FIG. 2.

In any of the configurations for intermediate interface 160, it is contemplated that the interface have its own data storage capabilities, so that the interface can store some or all of the information distributed amongst the machines of distributed database system 10. In an embodiment, a backend computer 170 (FIG. 2) hosting backend software can operate as intermediate interface 160. Computer 170/interface 160 can scrub data coming from different machine 12*e* and act as a link to the other machines 12 of distributed database system 10. Computer 170/interface 160 can in addition scrub other data, such as sensor outputs and lab results or other third party medical information, for each of machines 12, including different machine 12*e*.

Intermediate interface 160 enables different machine 12e to operate normally but in the eyes of system 10 as it were of the same type (e.g., same manufacturer or same model) as machines 12a to 12d and 12f to 12j. Intermediate interface 160 enables the data sent from distributed database system 10 for different machine 12e to be the same as the data sent from system 10 to machines 12a to 12d and 12f to 12j, and the data sent from different machine 12e to be provided in the same format within LAN 150 as the data sent from machines 12a to 12d and 12f to 12j.

As discussed above, LAN 150 of system 10 ties together the cluster of machines 12a to 12j. FIGS. 1B to 1D illustrate different example types for LAN 150. LAN 150 (including LAN's 150a to 150d discussed below) of FIGS. 1A, 2 and 3 can be of any type illustrated in FIGS. 1B to 1D and of any other type known to those of skill in the art today or developed in the future.

FIG. 1B illustrates that LAN 150 may be provided in the form a type using a network manager router 140 and/or a wireless access point 142 operating with a dynamic host configuration protocol ("DHCP") server (not illustrated). LAN 150 of FIG. 1B can be configured alternatively to use fixed addressing in addition to dynamic addressing. The DHCP functionality can be provided by router 140. FIG. 1B illustrates that LAN 150 may be wired (machines 12a and 12b), wireless (machines 12c to 12e) or wired and wireless (network manager router 140 connected to wireless access point 142 via a data communication link 144). This mode of network operation for LAN 150 of FIG. 1B can be called an "infrastructure mode".

FIG. 1C illustrates an alternative ad-hoc network LAN 150. Ad-hoc LAN 150 is a decentralized network that does not rely on network infrastructure, such as network manager router 140 or wireless access point 142 discussed above with FIG. 1B. Each machine 12a to 12e of ad-hoc LAN 150 sends and receives information to and from each other machine 12a to 12e directly, without a middleman or central hub. As illustrated in FIG. 1C, machines 12a to 12e of ad-hoc LAN 150 are typically (but do not have to be) connected wirelessly.

FIG. 1D illustrates an alternative power line LAN 150. Power line network uses the AC power line 146 bringing power to machines 12a to 12d to additionally carry network traffic (dotted line) to the machines. Due to the branched relationship of machines 12a to 12d to power line 146, power line LAN 150 normally (but does not have to) employs a network manager 148 to direct network traffic (dotted line) in and out of machines 12a to 12d.

Figure 2:
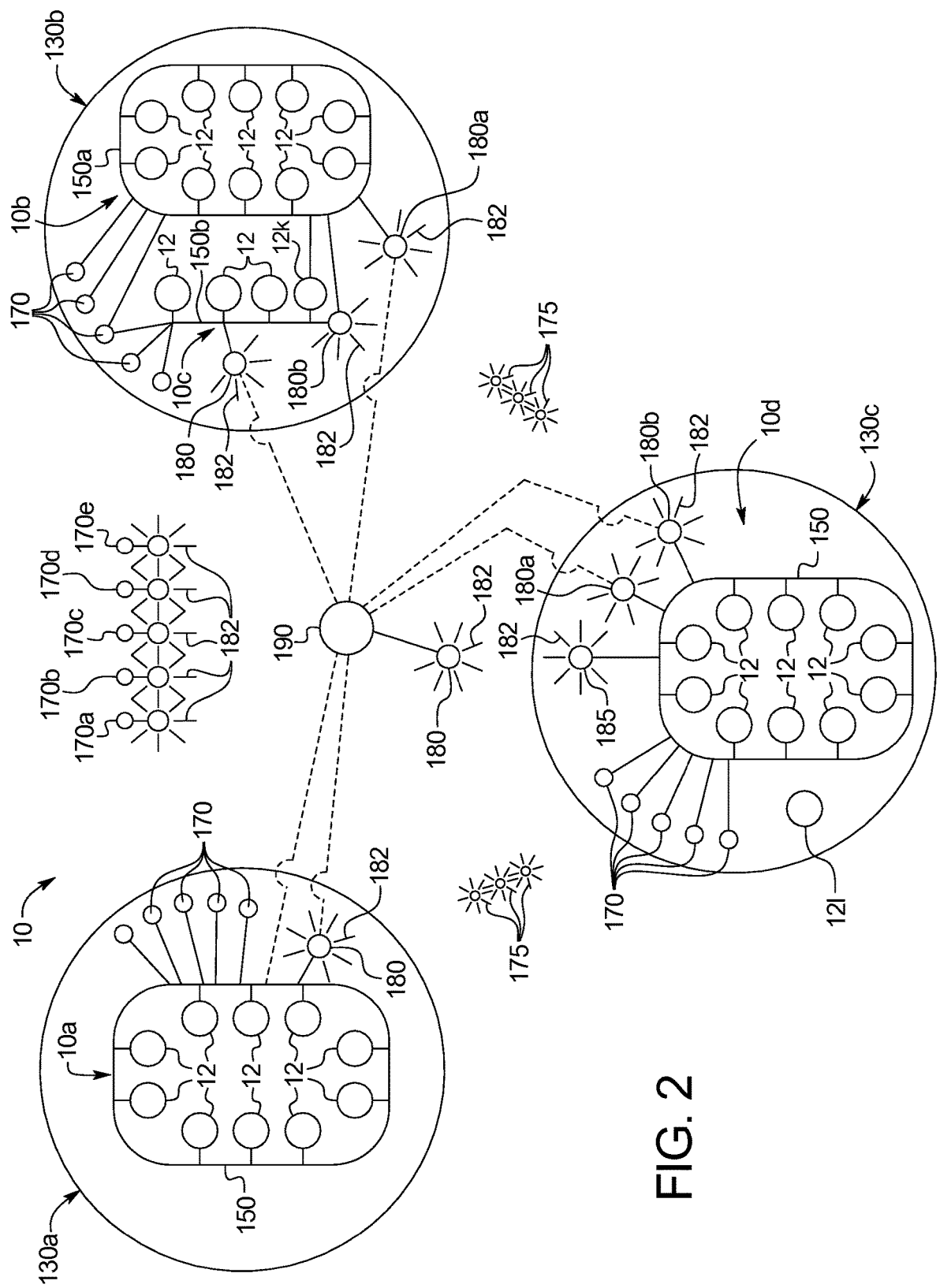
FIG. 2 is a schematic view of another embodiment of a distributed database system and method of the present disclosure.

Referring now to FIG. 2, another embodiment of distributed database system 10 includes multiple distributed databases 10a, 10b, 10c . . . 10n located in multiple clinics or dialysis centers 130a, 130b, 130c . . . 130n, respectively (the large circles in general represent the physical structure of the clinic or dialysis center). Clinics 130a to 130c (referred to collectively as clinics 130 or generally individually as clinic 130) can be part of a common medical group or network, or can be separate and individual. Machines 12 (referring to machines 12a to 12j . . . 12n above) can be different for different clinics or dialysis centers.

For example, machines 12 for clinic 130a can be infusion pumps. Machines 12 for clinic 130b can be hemodialysis machines that communicate via LAN 150a and peritoneal dialysis machines that communicate via LAN 150b. Machines 12 for clinic 130c can be hemodialysis machines. Three clinics 130a to 130c are merely an example; there can be more or less than three clinics operating with distributed database system 10.

Clinic 130a is outfitted with a distributed database 10a operating with a single LAN 150 to coordinate multiple machines 12 in a manner and including any of the alternatives discussed herein. LAN 150 of distributed database 10a is also connected to multiple personal computers 170 located within the LAN. Personal computers 170 enable doctors, clinicians, nurses, service people, etc., to (i) view information on distributed database 10a, (ii) input, and/or (iii) store information to the database, before, during and after treatment.

LAN 150 of distributed database 10a of clinic 130a is also connected to one or more server computer 180. Server computer 180 in an embodiment serves as a backup to the information stored on machines 12. As discussed in more detail below, machines 12 of distributed database 10a are periodically updated so that they have one mind, or the same mind, meaning each machine 12 is updated so that all machines 12 store the same data. Thus, each machine 12a to 12j serves as a backup to each of the other machines 12. Nevertheless, server 180 can be provided as additional protection in case each machine 12a to 12j of distributed database 10a is somehow damaged. Server 180 can also store older data that may be removed from machines 12 communicating via LAN 150 of distributed database 10a. For instance, distributed database 10a may be programmed such that each machine 12a to 12j stores six months or one year's worth of data for the patients associated with clinic 130a. Data older than the time limit are purged from the memories of machines 12a to 12j. Server 180 however can retain the older data in case it is needed for some reason. Server 180 of system 10 can alternatively or additionally manage information that is not part of the data shared between machines 12a to 12j. Server 180 can also be responsible for interfaces external to clinic 130c.

As discussed below in connection with FIG. 9, it is contemplated to add data to ongoing or moving trends. Each machine 12a to 12j stores each of the ongoing or moving trends. Thus even though the actual values of the older data may be removed from machines 12, the removed data can still maintained within the machines as part of the trends.

Server 180 can be connected to a wide area network ("WAN") or an internet via a wired connection 182, e.g., Ethernet connection or via a wireless connection 182, e.g., a mobile internet connection, such as UTMS, CDMA, HSPA or LTE. In either case, data stored at server 180 can be shared with (i) servers 180 of other dialysis centers 130b, 130c, e.g., dialysis centers of a same network or group, (ii) outside personal computers 170, e.g., computers 170a to 170e, (iii) personal communication devices ("PCD's") 175, such as smartphones, tablet computers, pagers and the like, and (iv) a central hub 190, e.g., a central control center for a group or network of dialysis centers 130a to 130c. Each of outside servers 180, personal computers 170a to 170e, PCD's 175, and central hub 190 of system 10 connects to the WAN or internet via a wireless or wired internet connection 182 in the illustrated embodiment. It is also contemplated to bypass or not provide server 180, and allow machines 12 of system 10 to communicate directly with personal communication devices ("PCD's") 175, such as smartphones and tablets, as well as other data sharing equipment, such as personal computers, pagers, printers, facsimile machines, scanners, combinations thereof, and the like.

Personal computers 170 inside clinics 130a to 130c are limited to accessing information specific to their respective clinic in one embodiment. Outside computers 170a to 170e may be able to access data from multiple clinics 130a to 130c, or may be dedicated to a single clinic or group of clinics. Outside computers 170a to 170e may be read only and not be able to store and/or modify data associated with clinics 130a to 130c.

Central hub 190 can communicate wired or wirelessly with any one or more server computer 180 (180a, 180b) within a clinic, as illustrated in each of clinics 130a to 130c. Alternatively or additionally, central hub 190 can communicate wired or wirelessly directly with any one or more LAN 150 within a clinic, as illustrated in clinic 130a. Central hub 190 in the illustrated embodiment has its own server computer 180, which connects to the WAN or internet via a wireless or wired internet connection 182. Central hub 190 can be an additional data backup to the servers 180 of dialysis centers 130a to 130c. Central hub 190 can alternatively or additionally track data trends and averages across multiple dialysis centers or medical clinics 130a to 130c. Central hub 190 can also perform other duties, such as inventory tracking and fulfillment. It is accordingly contemplated that central hub 190 can be part of or work in cooperation with a factory associated with the manufacturer of machines 12 and its related supplies. It is further contemplated to bypass server 180 and allow machines 12 of system 10 to communicate directly with hub 190 for stock balance information (e.g., dialyzers, ultrafilters, concentrates, disinfection fluids, blood sets, etc.), billing or economic transaction information, and/or lab data regarding different patients (e.g., bicarbonate, potassium levels, etc.).

Clinic or dialysis center 130b is outfitted with two or more distributed databases 10b and 10c that operate respectively with two or more LANs 150a and 150b, located within the same clinic or dialysis center. In the example given above, machines 12 located within clinic 130b can be hemodialysis machines communicating via LAN 150a of distributed database 10b and peritoneal dialysis machines communicating via LAN 150b of distributed database 10c. In another example, machines 12 located within clinic 130b can be hemodialysis machines of a first manufacturer communicating via LAN 150a of distributed database 10b and hemodialysis machines of a second manufacturer communicating via LAN 150b of distributed database 10c. In a further example, machines 12 located within clinic 130b can be first medical delivery pumps communicating via LAN 150a of distributed database 10b and second medical delivery pumps communicating via LAN 150b of distributed database 10c. The separate LAN's 150a and 150b of distributed databases 10b and 10c, in general, group machines having common input parameters and output data. LAN's 150a and 150b of distributed databases 10b and 10c may also be separated based upon geographical location, for example, LAN's 150a and 150b may each operate with the same types of machines 12 but be separated because they are located at different rooms or areas of clinic 130b.

PCD's 175 communicate with servers 180 (180a, 180b), central hub 190, personal computers 170, other PCD's, and possibly directly with machines 12 over the WAN or internet using mobile internet connections (such as UTMS, CDMA, HSPA or LTE) or satellite protocols as is known to those of skill in the art. PCD's 175 can be carried by doctors, clinicians, nurses (e.g., for inside or outside of clinics or dialysis centers 130a to 130c. Patients may also use PCD's 175, e.g., during treatment to (i) provide feedback concerning their current treatment or history, (ii) self-assessment, and/or (iii) ask a question to the nurse or clinician to answer either during a current treatment or for a subsequent treatment.

Access to data stored at machines 12 of distributed databases 10b and 10c via PCD's 175 and personal computers 170 can be password protected. It is also contemplated to separate data stored at machines 12 of distributed databases 10b and 10c into patient-identified data and patent de-identified data and to restrict access to any patient-identified data. For example, patient-identified data may be restricted to doctors, nurses or clinicians located within a clinic 130a to 130c and who are associated with a particular LAN 150 of a distributed database 10a to 10d. De-identified data on the other hand may be available to people located outside of clinics 130a to 130c, e.g., marketing people associated with the clinics or with the manufacturing of machines 12 and their supplies, staff responsible for technical services, and manufacturers of machines 12 for monitoring how the machines are performing and/or implementing preventive updates. The above-mentioned staff and employees associated with the manufacturer may be located at central hub 190 for example.

Even amongst the categories of patient-identified data and patient de-identified data, it is contemplated for distributed database system 10 to restrict data access levels within the categories. For example, under the category of patient-identified data, there may be high, medium and low access levels, where a doctor has high access, clinicians and nurses have medium access, while patient's have low access (e.g., limited to their own data). An administrator can be assigned to maintain and modify the access levels as needed. The access levels are tied to the doctor's, clinician's, nurse's and patient's passwords in one embodiment, so that the appropriate access level is established automatically upon login. The access levels can also be applied to machines 12, such that a doctor, clinician, nurse and/or patient can log into any of the machines and be restricted to the appropriate level of access.

Each LAN 150a and 150b of distributed database 10b and 10c of clinic or dialysis center 130b in the illustrated embodiment connects to its own server computer 180 (180a, 180b) having a WAN or internet connection 182. Each LAN 150a and 150b of distributed database 10b and 10c also enables communication with personal computers 170. At least one personal computer 170 illustrated for clinic 130b can communicate with distributed databases 10b and 10c via both LAN's 150a and 150b. Clinic or dialysis center 130b also includes a server computer 180a that communicates only with distributed database 10b and a second server computer 180b that communicates with both distributed databases 10b and 10c via both LAN's 150a and 150b. Server computers 180a and 180b may or may not have a WAN or internet connection 182.

Clinic or dialysis center 130b also illustrates that one or more machine, such as machine 12k, can operate with multiple distributed databases 10b and 10c. The data synchronized in different distributed databases 10b and 10c can be different, and it may also be data of a different type. For example, distributed database 10b can be used for sharing medical treatment information, while distributed database 10c is used to share backend information, such as machine setting information, e.g., language of the machine, or user interface appearance of the machine. As discussed in detail with FIG. 3, each machine of a primary treatment information distributed database (such as database 10b) can also be a member of another distributed database (such as database 10c).

Clinic or dialysis center 130c is outfitted with a distributed database 10d having single LAN 150 supporting multiple medical machines 12. Personal computers 170 located within clinic 130c are placed in data communication with each other via LAN 150. Server computers 180a and 180b having any of the functionality described above are likewise placed in data communication with distributed database 10d via LAN 150. Thus, any distributed database or LAN discussed herein can be connected to two or more server computers 180.

Clinic 130c also illustrates that a sensing device or other medical equipment 185 may also communicate with distributed database 10d via LAN 150 via wired or wireless connection 182, such as an Ethernet, Wi-Fi or Bluetooth connection. Sensing device or medical equipment 185 can for example be a weight scale used by patients of machines 12 of LAN 150 of clinic 130c. Each patient weighs himself or herself before and/or after treatment. Those weights are then transmitted wired or wirelessly via LAN 150 to the machine 12 that the patient uses that day for treatment, for example, to the machine 12 that the patient decides or requests to use that day for treatment. The patient can, for example, scan his or her identification card or enter an ID number at both the weight scale and machine 12 so that the weight measurement taken and the particular machine 12 can be matched. Alternatively, the sensor reading is stored at the sensing equipment 185 (e.g., scale or blood pressure measurement device), after which the machine 12 that the patient uses that day asks for the reading from the one or more sensor.

Further alternatively, sensing equipment 185 sends the reading to all machines 12 of distributed database 10d. Here, a weight value, for example, is stored in the machines in a record or file for the particular patient in one embodiment.

Any of the above-described methodologies can be used to match a reading from a blood pressure measurement device 185 to the particular machine 12. Any of the above-described methodologies can also be used to match a glucose measurement from a glucose monitor to a particular machine 12. Any of clinics 130a to 130c can use or employ such equipment 185. Equipment 185 can also include any physiological sensing equipment associated with an emergency room or dialysis center, for example, electrocardiogram ("ECG"), water treatment equipment, bed scales, access disconnection devices, bioimpedance measurement devices, pH sensors, lab testing equipment, blood sample analyzers, and/or a psychological status application stored on a PCD 175.

It should be appreciated that sensing equipment 185 does not have to be undedicated sensing equipment, but can instead be one or more pieces of sensing equipment dedicated to a machine 12, e.g., via a USB connection, electrical connection, pneumatic connection (e.g., pneumatic pressure measurement device), cable or wirelessly (e.g., using Bluetooth, Wi-Fi or ZigBee). Sensing equipment data 185 here is associated with the patient being treated on the machine 12 and is made accessible to other machines via distributed database system 10 as described herein.

While distributed database system 10 of FIG. 2 illustrates multiple server computers 180, personal computers 170, PCD's 175, and central hub 190, it should be appreciated that none of those devices is needed to maintain system 10. Each of machines 12 of distributed databases 10a to 10d of distributed database system 10 is updated periodically to store the same data as each of the other machines 12 of the LAN. Server computers 180, personal computers 170, PCD's 175 and central hub 190 are not required to perform the updating. Instead, for example, personal computers and PCD's 175 can be used to view the data stored on machines 12 distributed database system 10, while personal computers 170, server computers 180 and central hub 190 can be used for data backup, trending and/or analysis.

Clinic 130c also illustrates a machine 12l, which is not present along LAN 150 and thus is not part of distributed database 10d. Machine 12l is still part of the overall distributed database system 10 of the present disclosure, however, because machine 12l may at anytime become part of distributed database 10d, at which time the collective data of all machines 12 of distributed database 10d is updated. In the meantime, treatment is performed at disconnected machine 12l using locally stored prescription parameters, etc., and operating software that may not be current. System 10 can make the user of machine 12l aware of its status.

Figure 3:
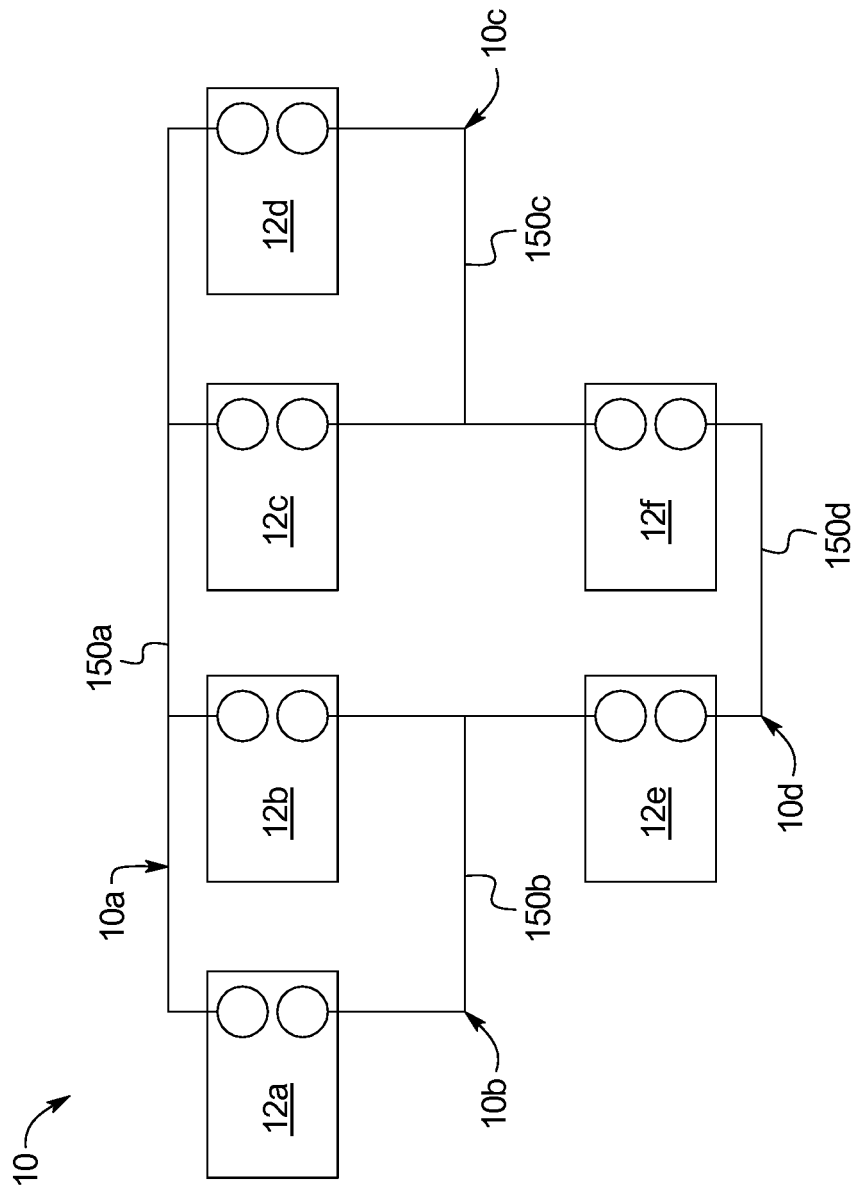
FIG. 3 is a schematic view of a further embodiment of a distributed database system and method of the present disclosure.

Referring now to FIG. 3, distribute database system 10 is further illustrated. As discussed above in connection with machine 12k of clinic 130b in FIG. 2, each machine 12 can be part of multiple distributed databases. In FIG. 3, machines 12a and 12b belong to distributed databases 10a and 10b operating with LAN's 150a and 150b, respectively. Machines 12c and 12d belong to distributed databases 10a and 10c operating with LAN's 150a and 150c, respectively. Machine 12e belongs to distributed databases 10b and 10d operating with LAN's 150b and 150d, respectively. Machine 12f belongs to distributed databases 10c and 10d operating with LAN's 150c and 150d, respectively. In alternative embodiments, any one or more of machines 12 may belong to three or more distributed databases.

Distributed databases 10a to 10d can be grouped by machine or device type as well. For example, machines 12a to 12d may be drug delivery pumps or IV pumps, while machines 12e and 12f are other types of devices, such as, oxygenators or sensing equipment, such as, glucose monitoring. Distributed database 10b can be dedicated to a first patient connected to two IV pumps 12a and 12b and an oxygenator 12e. Distributed database 10c can be dedicated to a second patient connected to two IV pumps 12c and 12d and a glucose monitor 12f. Patient databases 10b and 10c can each have a common prescription, e.g., for operating pumps 12a, 12b and for incorporating oxygenator 12e for the first patient, and for operating pumps 12c, 12d and for incorporating glucose monitor 12f for the second patient. Distributed database 10a shares IV pump data across multiple patients, while distributed database 10d shares oxygenator 12e and glucose monitor 12f data across multiple patients. Distributed databases, such as databases 10a and 10d may therefore be dedicated to a patient, a group of like machines, or a group of like functionality, e.g., physiological sensing.

Machines 12 belonging to multiple distributed databases 10a to 10d allow overall system 10 to, for example, share medically related data, e.g. software updates and software configurations, in one distributed database 10a to 10d, while sharing medical data, e.g. prescription input data and treatment output data in another distributed database 10a to 10d. Doing so allows different distributed databases to be managed differently, for example, one distributed database may be a real time database, while another distributed database may be updated at set intervals, e.g., at the end of a shift or workday.

The different distributed databases 10a to 10d can perform different tasks, resulting in a very flexible overall system 10. In FIG. 3, assume for example that machines 12a to 12d are performing hemodialfiltration ("HDF"), while machines 12e and 12f are performing hemodialysis ("HD").

Distributed database 10a accordingly provides prescription parameters and collects treatment output data for HDF, while distributed database 10d does the same for HD. Distributed databases 10b and 10c are then used to share data based on some commonality between machine group 12a, 12b, 12e and group 12c, 12d, 12f, respectively. For example, machine group 12a, 12b, 12e could have a different language or user interface appearance than machine group 12c, 12d, 12f. Distributed databases 10b and 10c provide and track such different languages or user interface appearances.

Or, machine group 12a, 12b, 12e and group 12c, 12d, 12f may require different real time data to be monitored. For example, machine group 12a, 12b, 12e can be dedicated to a certain category of patient, e.g., infants, where operating pressure limits must be monitored very closely.

System 10 of FIG. 3 allows databases 10b and 10c to be real time alarm distributed databases that are separate from and thus incapable of interrupting, main treatment distributed databases 10a and 10d. Distributed database 10b is also able to separate, e.g., infant, machine group 12a, 12b, 12e for specialized shared real time alarm purposes from the shared real time alarms of distributed database 10c for machine group 12c, 12d, 12f (e.g., a normal adult machine group).

Real time alarm data (which is not limited to multiple distributed database scenarios and is described elsewhere in this application) allows nurses and clinicians to see an alarm occurring in a different room, on the other side of a wall, or at the other end of a clinic. The indication of an alarm could be as simple as a small pulsating icon in a corner of the user interface 14 (see FIGS. 8A, 8B, 10) with an indication of which machine 12 is alarming. The nurse or clinician can press the icon to learn more information about which type of alarm is occurring. The icon can be of two or more types (i) for more demanding alarms versus (ii) for more attention alerting alarms. Alternatively, a plurality of icons are provided, for example, with a number, to indicate the type of alarm, e.g., icon with number 1=blood leak alarm, icon with number 2=UF rate alarm, icon with number 3=venous pressure alarm, etc.

Each of the circles illustrated inside machines 12a to 12f of FIG. 3 may represent a different memory 18 (see FIG. 10) within the machines or separate areas of the same memory 18 within the machines. Distributed databases 10a and 10d may be updated and synchronized according to any of the same or different methods discussed below in connection with FIGS. 4A to 7C, at the same or different times. Real time data can also be shared according to the methods discussed below in connection with FIGS. 4A to 6B, with a primary difference being that instead of running only a single time through the flow diagrams from "start" to "end", which is performed for normal treatment (e.g., at the end of the day), a loop for real time data is cycled from "end" to "start" in at least one of the methods of FIGS. 4A to 6B at a desired frequency to look for new pertinent real time, e.g., alarm, data.

While it is contemplated for system 10 to allow real time data sharing, it is also contemplated for the system to implement safeguards regarding such sharing. For example, in an embodiment, certain functions, such as downloading new software and servicing machines 12 can only take place after treatment when machines 12 are not performing treatment, e.g., are in a service mode, are in a hibernation mode or are otherwise disabled. It may be possible to transfer certain additional data during a disinfection mode when the machine is running but a patient is not connected. When a patient is connected, however, system 10 can be operated so as to take care not to transfer any data that may interrupt treatment or bother the patient.

In an embodiment, real time treatment data is not permanently stored in any machine 12. For example, real time data can be stored for as long as the treatment is ongoing, so that it can be viewed in a summary screen as described in detail herein, or for longer periods, such as a week, multiple weeks, or months. When treatment of any machine 12a to 12j is completed, or the real time data storage period expires, its real time data can be purged. Storing all real time treatment data permanently may fill memory too quickly. Generally, the values that will be stored permanently will be total values, average values, mean values, or other combined or statistically relevant values.

The different distributed databases 10a to 10d can have different updating speeds based, for example, upon which type of medically related data they convey and allow for access. Real time databases 10 may have high frequency update speed (e.g., microseconds, seconds, minutes), while administrative type of databases such as inventory and/or staffing databases 10 can be updated at a slower speed, such as once every hour, day or shift.

Figure 4A:
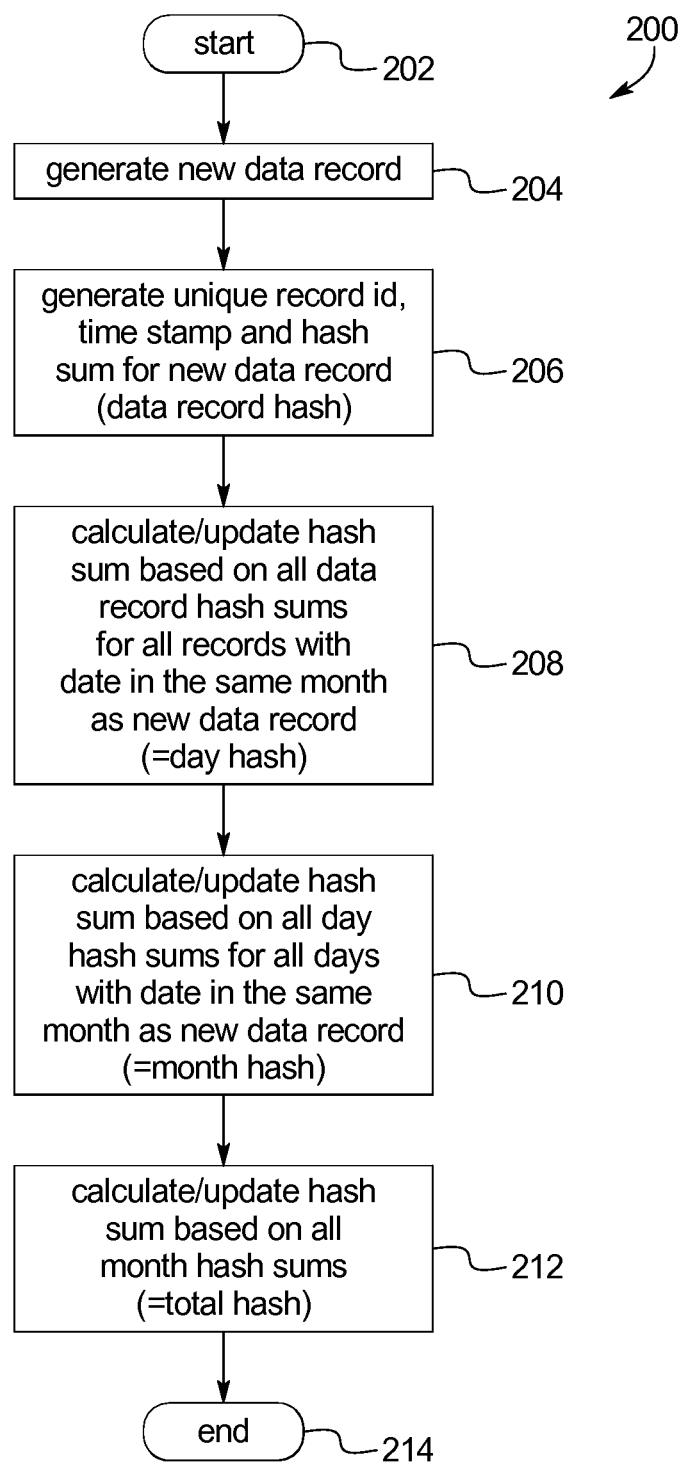
FIG. 4A is a logic flow diagram illustrating one embodiment of a subroutine for generating metadata for data transferred via the distributed database system and method of the present disclosure.

Referring now to FIG. 4A, method 200 illustrates one embodiment for assigning tag data or metadata to new data shared by the distributed database system 10 of the present disclosure. Method 200 can be used as a subroutine and at oval 202, method 200 begins. At block 204, a new piece of data or data record is generated. The new data can be any of (i) prescription input parameters or data (e.g., machine operating parameters), (ii) treatment output data (e.g., UF removed, total blood volume moved, total dialysis fluid volume consumed, heparin volume consumed, alarms, and treatment effectiveness measurements Kt/V, etc.), (iii) technical input data (e.g., calibrations, alarm limits, etc.), (iv) technical output data (e.g., actual component usage, sensor measurements, etc.), and (v) administrative data (e.g., inventory data and staffing data) generated by or inputted into any machine 12 of distributed database 10. The new data can be an array of data, for example, a snapshot of treatment output data generated at a particular time, e.g., pressure readings from all pressure sensors of a machine 12 operating at a given time. In this manner, the tag data or metadata can represent a larger collection of data, so that there does not have to be tag data or metadata for each new individual piece of data. New data therefor represents either a single piece of new data or an array of new data.

At block 206, the machine 12 at which the new data (e.g., array of data) is generated generates (i) a unique record identification ("id"), (ii) a time stamp, and (iii) a hash sum or checksum for the new data. The unique record id identifies both the machine 12 and the sequence number for that machine, which created the new data. So in FIG. 1A, if machine 12c at sequence number 0000000444 creates new data, the unique id could be 12c: 0000000444. In essence, the unique id gives the new data a home (the particular machine or computer sharing distributed database system 10) and a location within the home, that is, the sequence number.

The hash sum identifies the actual content of the new data (e.g., array of data). For example, suppose a new array of data includes six pressure readings [a, b, c, x, y, z]. A hash sum, hs002500 could be generated for those readings, so that hs002500=[a, b, c, x, y, z]. hs002500 now represents the six pressure readings. The machines 12 of system 10 therefore do not have to look for the specific pressure readings; rather, the machines look to see if hs002500 exists. As explained in more detail below, the hash sum can be recalculated by a transferee machine of the distributed database after transfer from a transferor machine. The transferee machine can then compare the transferred and calculated hash sums to confirm that data has not been corrupted during transfer or to raise a system error if data corruption is detected. The transferee machine can ask the transferor machine to retransmit the data a predefined number of times, check for data corruption after each transfer, and raise a system error only after the data is found to be corrupted after each of the predefined number of data transfers.

The time stamp identifies the time at which the new data (e.g., array of data) is generated. The time stamp could, for example, be 30 May 2015/8:15 a for data created at 8:15 am on May 30, 2015. The time stamp serves to determine which data to move forward with when two hash sums for the same unique id do not match. In an embodiment, the hash sum corresponding to the later time stamp is chosen, as illustrated below in connection with FIG. 5B. A complete record set of tag data or metadata for data array [a, b, c, x, y, z] could therefor be (i) unique id 12c: 0000000444, (ii) time stamp 30 May 2015/8:15 a, and (iii) hash sum hs002500, or 12c: 0000000444; 30 May 2015/8:15 a; hs002500.

Blocks 208, 210 and 212 of method 200 each involve calculating and updating hash sums for multiple, increasing time periods. In the illustrated embodiment, the time periods include day, month, and multi-month. Alternatively, the time periods could be shift, day, week, and month. There can be as many different time periods as desired, e.g., three to six time periods. The time periods can be any desired duration, e.g., minutes, hours, shifts, days, weeks, months, years, etc. For ease of description, the remainder of the example of FIG. 4A uses day, month, and multi-month time periods.

At block 208, the machine 12 at which the new data (e.g., array of data) is generated calculates or updates a "day hash" for all has sums generated at that machine over the same day or twenty-four hour period during the same month. "day hash 30 May 2015" for example could equal or include hs002500 through hs010000 for a particular machine 12. The "day hash" calculation could be performed at the end of each day for example.

At block 210, the machine 12 at which the new data (e.g., array of data) is generated calculates or updates a "month hash" for all hash sums generated at that machine over the current month. "month hash may" for example could equal or include day hash 1 May 2015 to day hash 31 May 2015. The "month hash" calculation could also be performed at the end of each day, or set of days such as a week, for example.

At block 212, the machine 12 at which the new data (e.g., array of data) is generated calculates or updates a "total hash" for all hash sums generated at that machine over the current year, for example, "total hash 2015" for example could equal or include "month hash january" to "month hash may". The "total hash" calculation could be performed at machine 12 at the end of each week or month, for example.

At oval 214, method 200 ends.

Figure 4B:
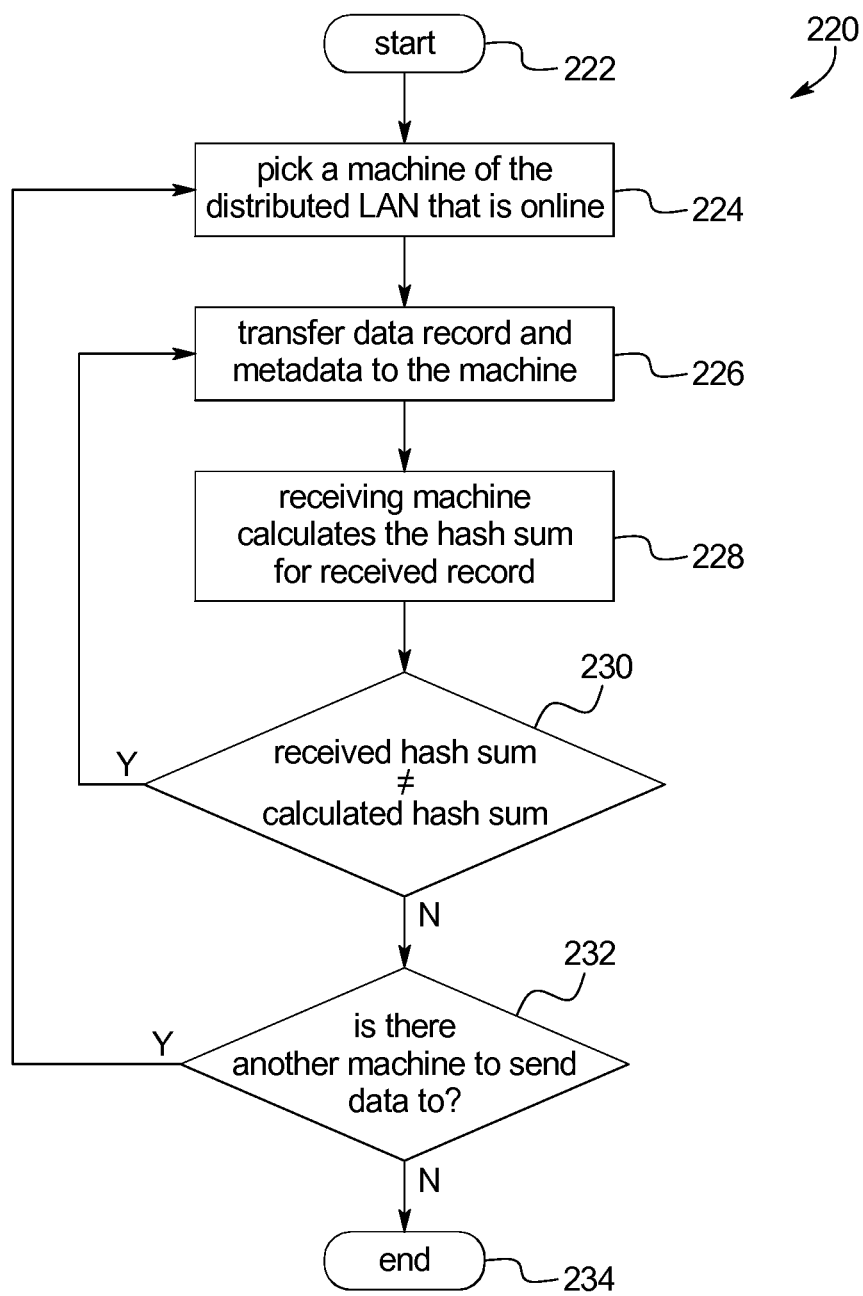
FIG. 4B is a logic flow diagram illustrating one embodiment of a subroutine for sending data to other machines or sensing equipment of the distributed database system of the present disclosure.

Referring now to FIG. 4B, method 220 illustrates one embodiment for sending data from one machine 12 to all other machines 12 of distributed database system 10. Method 220 can be used as a subroutine, and at oval 222, method 220 begins. As discussed above, either a single machine 12 or an aggregate of machines 12 can send to all other machines 12b to 12j of system 10. For example, in FIG. 1, a single machine 12a can send its new data to all other (online) machines 12b to 12j of system 10. Or, aggregated new data from machines 12a, 12b and 12c can be sent to all other (online) machines 12d to 12j of system 10. Aggregating the data can optimize (minimize) the number of new data pushes and thereby reduce the potential for error. It should be appreciated therefore that method 220 can be viewed from the standpoint of a single machine 12 sending its new data or as an aggregate of machines (e.g., 12a, 12b, 12c) sending their collective new data.

At block 224, the machine 12 (or aggregate of machines 12) picks a new machine 12 (outside aggregate if aggregate used) of system 10, which is currently online. At block 226, new data along with data tagging or metadata described in FIG. 4A are sent to the recently selected machine. At block 228, the receiving machine 12 calculates its own hash sum for the received new data entry. At diamond 230, the receiving machine 12 determines whether the received hash sum is different than the recently calculated hash sum. If at diamond 230, the received hash sum is different than the recently calculated hash sum, then the newly selected machine 12 notifies the sending machine 12 (single machine 12 or representative machine 12 of an aggregate that sent the new data to the selected machine 12) of the hash sum mismatch. Upon receiving the hash sum mismatch, the sending machine 12 repeats the sending step of block 226, and the loop between block 226 and diamond 228 is repeated until at diamond 230, the received hash sum is the same as the recently calculated hash sum, which ensures eventually that data transfer between the sending and receiving machines 12 is not corrupted.

When it is determined at diamond 230 that the received hash sum is the same as the recently calculated hash sum, the sending machine 12 (single machine 12 or representative machine 12 of an aggregate) determines whether there is another machine 12 (outside aggregate if aggregate used) to which to send the new data. If so, method 220 steps 224 to 232 are repeated until there are no new machines, as determined at diamond 232, at which time method 220 ends, as illustrated at oval 234.

Figure 1A:
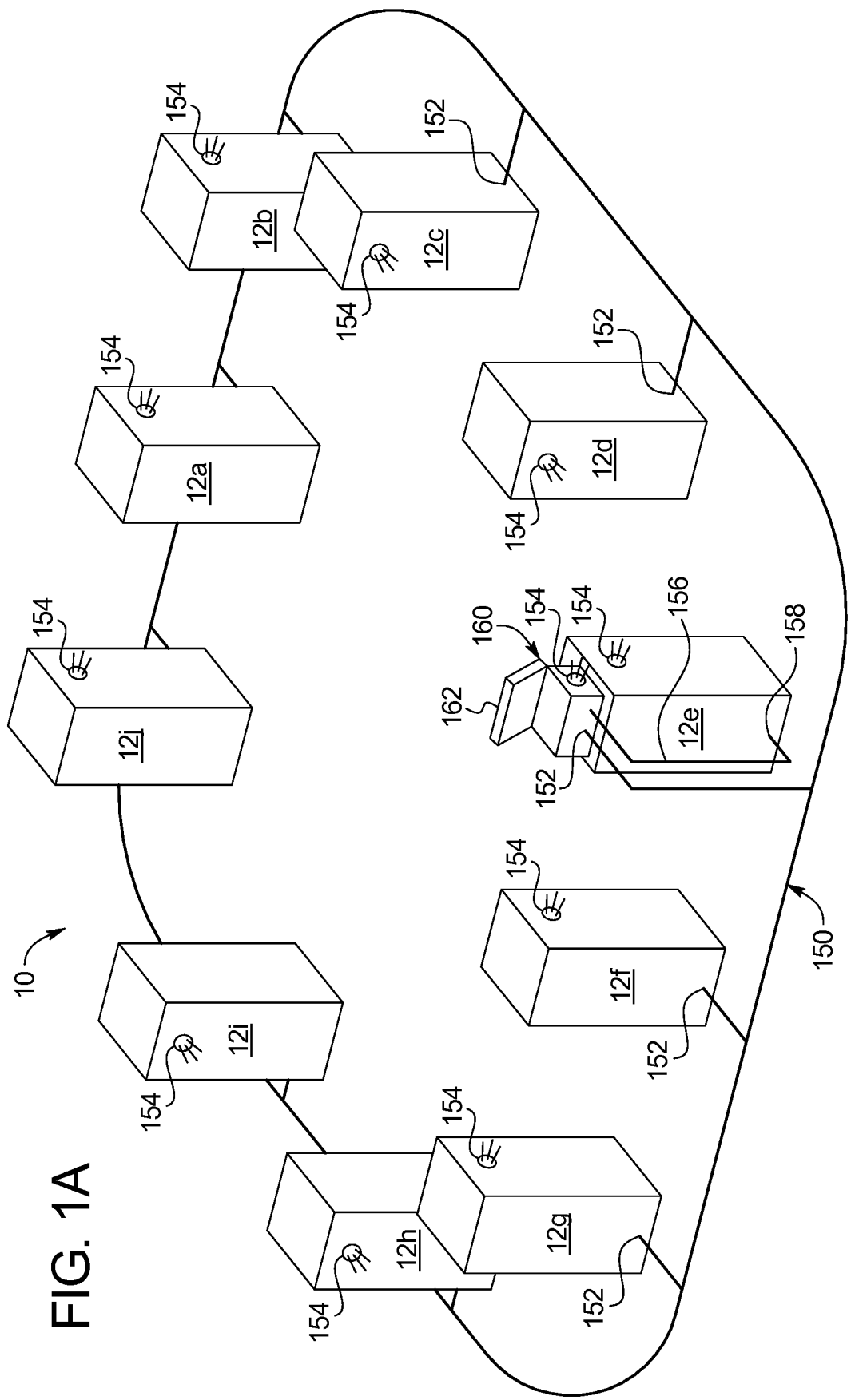
FIG. 1A is a schematic view of one embodiment of a distributed database system and method of the present disclosure.
Figure 1B:
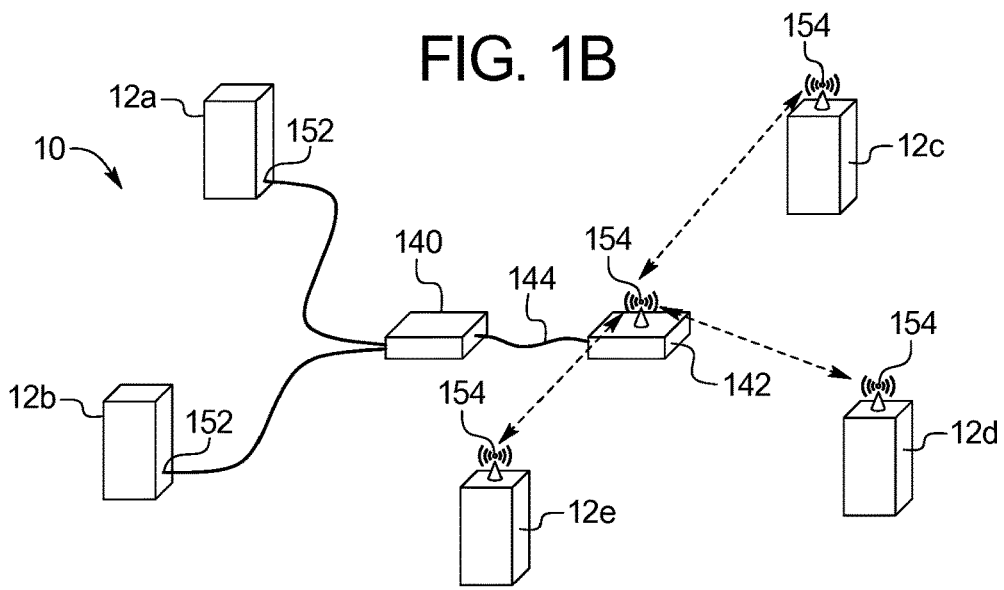
FIGS. 1B to 1D illustrate different example types of local area networks suitable for use with the distributed database systems and methods of the present disclosure.
Figure 1C:
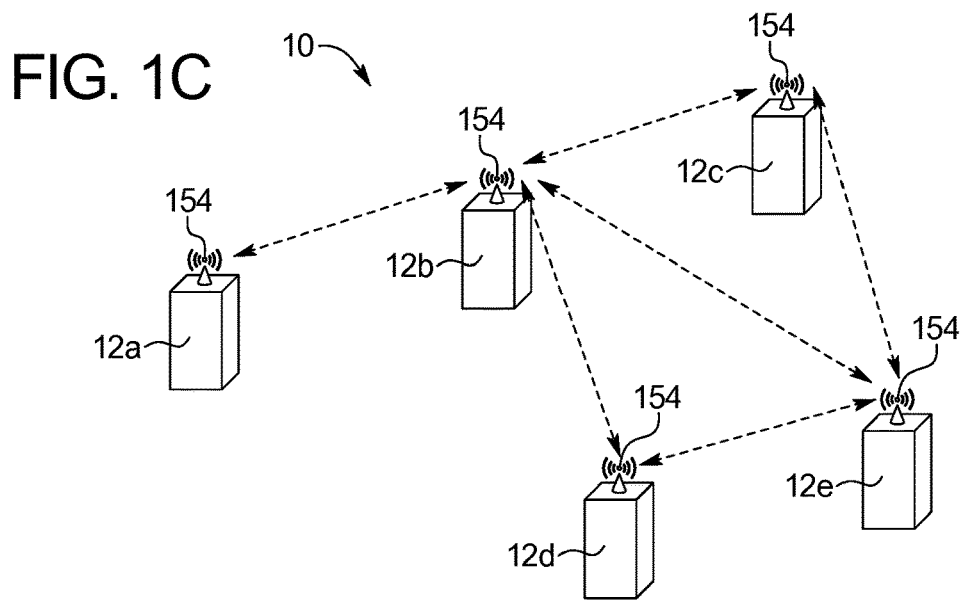
Figure 1D:
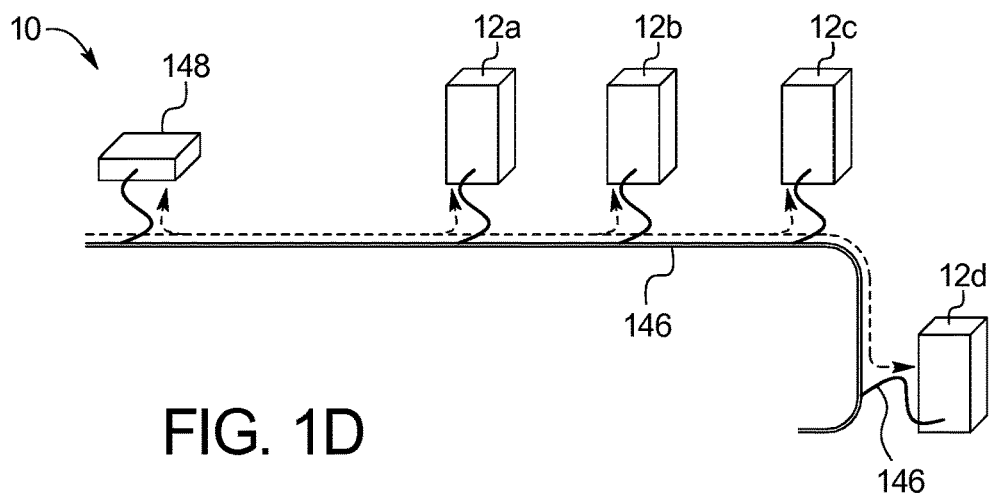
Figure 5A:
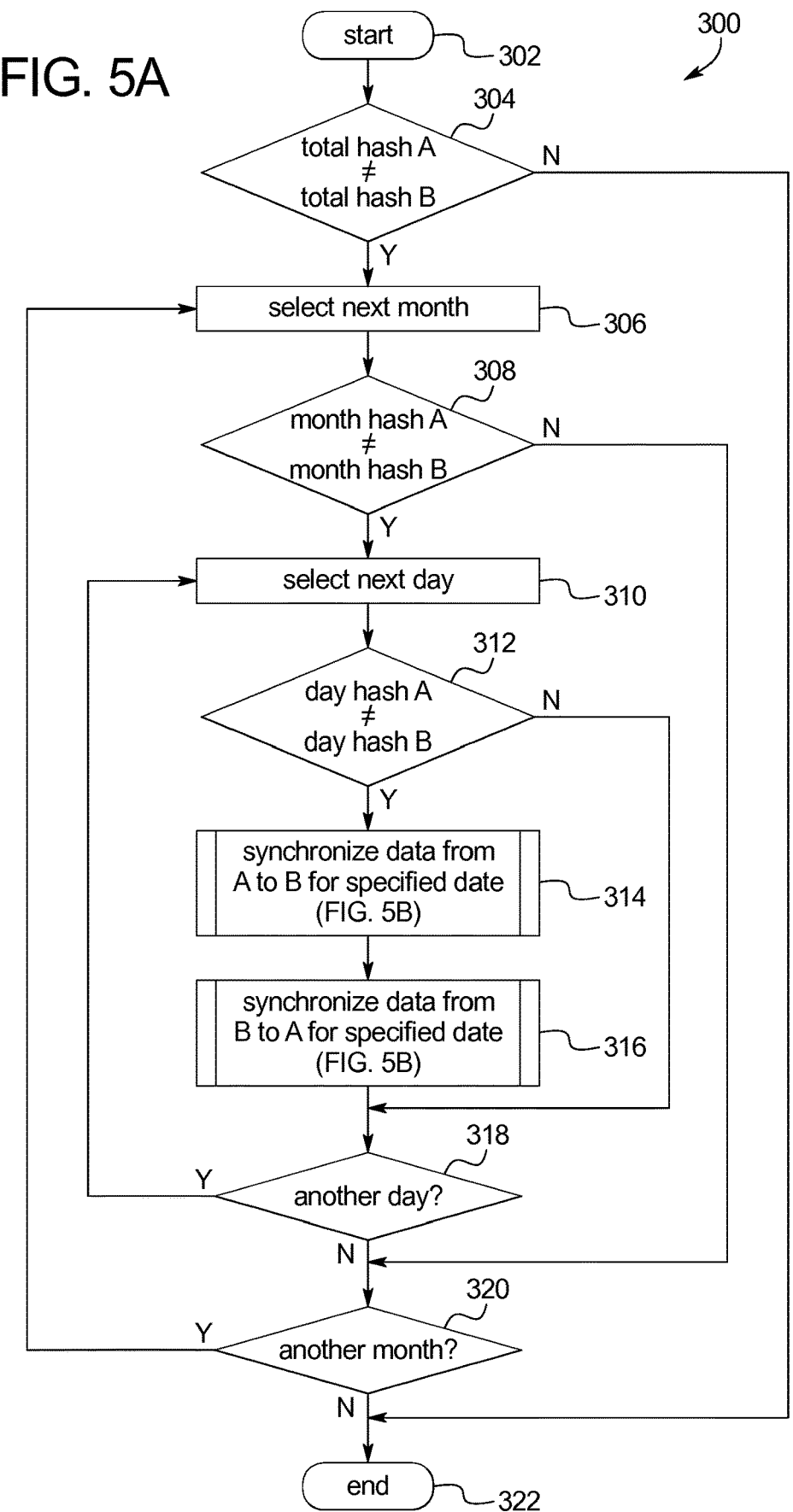
FIG. 5A is a logic flow diagram illustrating one embodiment of a subroutine for synchronizing different machines using the distributed database system and method of the present disclosure.
Figure 5B:
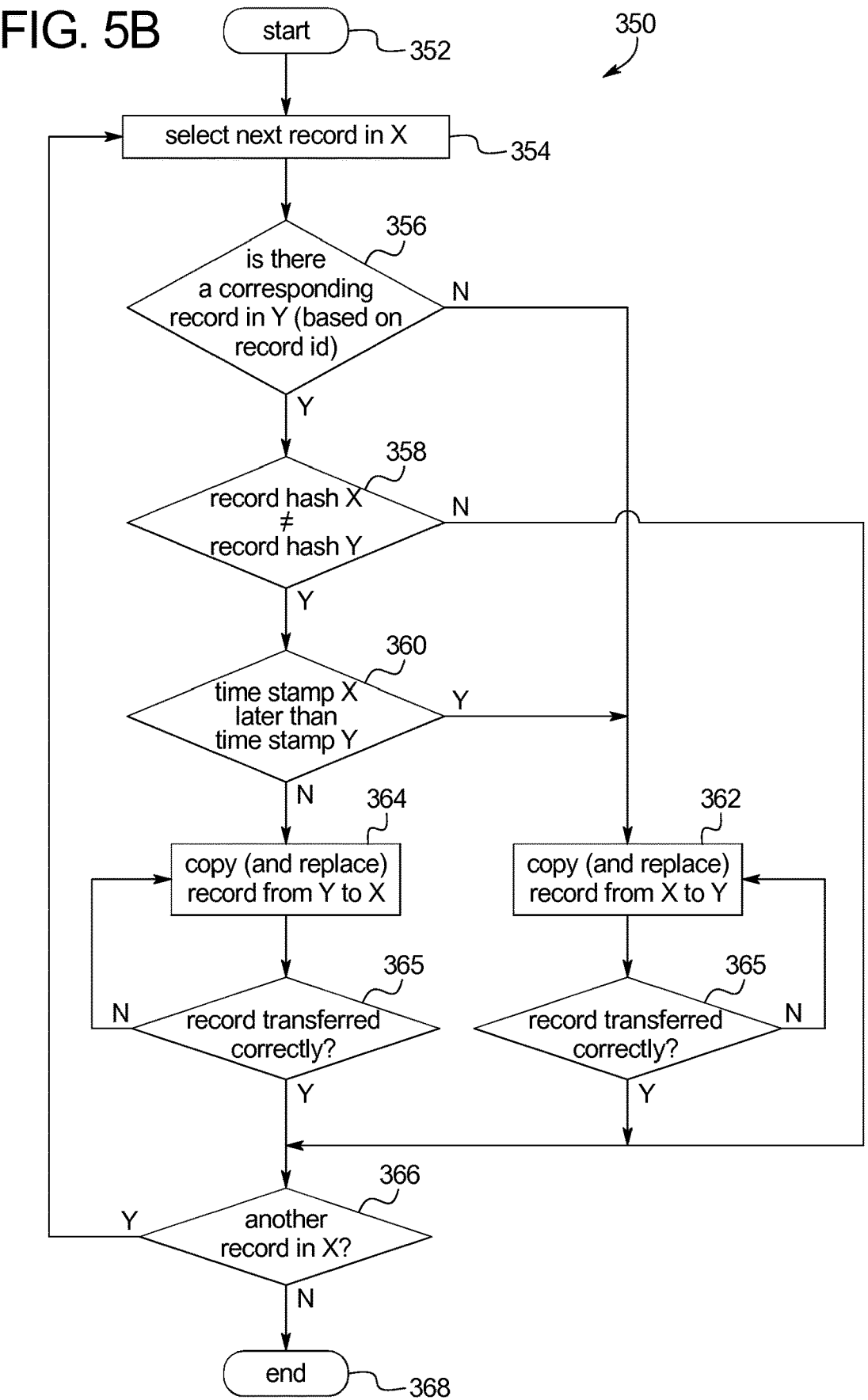
FIG. 5B is a logic flow diagram illustrating one embodiment of a subroutine for comparing data between two machines, the subroutine used with the logic flow diagram of FIG. 5A.

Referring now to FIGS. 5A and 5B, method 300 illustrates one example of how two machines 12 of distributed database system 10, e.g., any two of machines 12a to 12j of FIG. 1A, can synchronize with one another, that is, check to see if they share the same data, and if they do not share the same data, then to update one another as needed so that the two machines do share the same data. At oval 302, method 300 begins. As will be seen from below, method 300 incorporates the data tagging or metadata illustrated in connection with FIG. 4A.

At diamond 304, method 300 determines whether the total hash calculation performed in connection with FIG. 4A for a first machine 12 of the distributed database system 10, e.g., machine 12a, is not equal to the total hash calculation performed in connection with FIG. 4A for a second machine 12 of the distributed database system 10, e.g., machine 12b. Comparing total hash for machine 12a (total hash A) to that of machine 12b (total hash B) is performed at one of the machines in one embodiment. A protocol can be set so that the machine with the lower or earlier identification number performs the comparison, e.g., machine 12a performs the comparison when compared to remaining machines 12b to 12j. Machine 12b performs the comparison when compared to remaining machines 12c to 12j, and so on. In an alternative protocol, both machines perform the comparison to create a check on the result. Here, the machine with the lower or earlier number can be set to perform the comparison first. If the result is not the same for machine 12a performing the total hash comparison versus machine 12b performing the total hash comparison, then method 300 ends in a system error, causing system 10 to prompt an administrator for assistance. The above two protocols, and/or alternatives thereof, can be used for each of the queries performed at diamonds 304, 308, 312, 318 and 320 of FIG. 5A.

If the answer to the query at diamond 304 answer is no, meaning total hash for machine 12a does equal total hash for machine 12b, then the two machines 12a and 12b are synchronized completely. Method 300 proceeds to the end at oval 322.

If the answer to the query at diamond 304 is yes, meaning total hash for machine 12a does not equal total hash for machine 12b, then method 300 looks to drill down into the hash sums to see where the problem lies. At block 306, the comparing machine 12a or 12b (or if both machines compare then the machine performing the comparison first) selects a next month. In an embodiment, the first month selected is the current month because the preceding months may have already been synchronized, leading to the likelihood that the mismatch probably resides in the current month.

At diamond 308, the comparing machine 12a or 12b (or alternatively both machines 12a or 12b as discussed above) determines for the month selected at block 306 whether the month hash for machine A (month hash A) does not equal the month hash for machine B (month hash B). If the answer to the query of diamond 306 is no, meaning that month hash A does equal month hash B, then method 300 proceeds to diamond 320, which queries whether there is another month to analyze. If the answer to the query 320 is no, and there is no other month to analyze, method 300 ends, as illustrated at oval 322. If the answer to the query 320 is yes, and there is another month to analyze, then method 300 returns to select another month at block 306 (e.g., the first preceding month, followed by the second preceding month, and so on), after which the loop just described between block 306, diamond 308 and diamond 320 is repeated until a month hash A mismatch with month hash B occurs at diamond 308, or no more months remain, as determined at diamond 320.

If the total hash query at diamond 304 concludes that a mismatch does exist, but the monthly loop between block 306, diamond 308 and diamond 320 shows no mismatch, then method 300 ends in a system error, causing system 10 to prompt an administrator for assistance.

When method 300 finds a month in which a mismatch has occurred at diamond 308, method 300 next looks for the one or more day of the month in which the mismatch occurred. At block 310, the comparing machine 12a or 12b (or if both machines compare then the machine performing the comparison first) selects a next day. In an embodiment, the first day selected is the current day because the preceding days may have already been synchronized, leading to the likelihood that the mismatch probably resides with the current day.

At diamond 312, comparing machine 12a or 12b (or alternatively both machines 12a or 12b as discussed above) determines for the day selected at block 310 whether the day hash for machine A (day hash A) does not equal the day hash for machine B (day hash B). If the answer to the query of block 306 is no, meaning that day hash A does equal day hash B, then method 300 proceeds to diamond 318, which queries whether there is another day to analyze. If the answer to the query 318 is no, and there is no other day of the current month to analyze, method 300 inquires whether there is another month (e.g., another preceding month) to analyze as discussed above in connection with the loop including diamond 320.

If the answer to query 318 is yes, and there is another day to analyze, then method 300 returns to select another day at block 310 (e.g., the first preceding day, followed by the second preceding day, and so on), after which the loop just described between block 310, diamond 312 and diamond 318 is repeated until a day hash A mismatch with day hash B occurs at diamond 308, or no more days remain, as determined at diamond 318.

If the monthly query at diamond 308 concludes that a mismatch within a month does exist, but the loop between block 310, diamond 312 and diamond 318 shows no day hash mismatch for the month, then method 300 ends in a system error, causing system 10 to prompt an administrator for assistance.

When method 300 finds a day in which a mismatch has occurred at diamond 308, method 300 proceeds to the hash A and hash B synchronization steps illustrated at blocks 314 and 316. At block 314, day hash A is synchronized to machine 12b for the data mismatch date. At block 316, day hash B is synchronized to machine 12a for the data mismatch date. A subroutine for blocks 314 and 316 is discussed next in connection with FIG. 5B. It should be appreciated first, however, that once total hash A is determined to be different than total hash B at diamond 304, there may be multiple days and multiple months within the hash totals that are mismatched. Thus even after performing the synchronizing at blocks 314 and 316 for a given day within a month, there may be one or more other day within the same month needing the synchronization of blocks 314 and 316. Likewise, even after synchronizing one or more days of a first month via the synchronization of blocks 314 and 316, there may be one or more days of one or more additional month of total hash A and total hash B, as determined within the loop defined by block 306 to diamond 320, needing the synchronization of blocks 314 and 316.

Once no more months for machines 12a and 12b need synchronization, as determined by the loop defined by block 306 to diamond 320, method 300 ends, as illustrated at oval 322.

Referring now to FIG. 5B, method 350 illustrates one embodiment for a subroutine used at both blocks 314 and 316 of method 300 of FIG. 5A. In FIG. 5B, X is the initiating or "from" machine in blocks 314 and 316. Thus X is machine 12a in block 314 and machine 12b in block 316. Likewise, Y is machine 12b in block 314 and machine 12a in block 316. At oval 352, method 350 begins.

At block 354, machine X selects a newly created piece or array of data to be analyzed. In one embodiment, machine X knows the last unique id to be analyzed and selects the next unique id in the sequence to be analyzed at block 354.

At diamond 356, method 350 queries whether the Y machine currently stores the corresponding unique id. If the answer is no, and machine Y does not already contain the unique id record being analyzed, then machine X copies and replaces the unique id record (along with its time stamp, hash sum, and corresponding actual data) to machine Y.

If the answer at diamond 356 is yes, and machine Y does already contain the unique id record being analyzed, then method 350 determines whether the current record hash for machine X does not equal the current record hash for machine Y, as determined at diamond 358. If the answer is no, and record hash X does equal record hash Y, then no further action is needed for this unique id, and method 350 proceeds to diamond 366 to look to see if a next unique id exists.

If the answer at diamond 358 is yes, and record hash X does not equal record hash Y, then method 350 at diamond 360 determines which machine's time stamp is later. If the time stamp for machine X is later than the time stamp for machine Y, then machine X at block 362 copies and replaces the unique id record (along with its time stamp, hash sum, and corresponding actual data) to machine Y. Next, at diamond 363, machine Y checks to see whether the unique id record (along with its time stamp, hash sum, and corresponding actual data) transferred correctly to machine Y. In one embodiment, machine Y calculates its own hash sum and compares it to the hash sum received from machine X (as discussed in connection with method 220 of FIG. 4B) to determine if the record transferred correctly. If not, e.g., the calculated hash sum does not equal the received hash sum, machine Y sends a corresponding message to machine X, and machine X repeats the step at block 362. The loop at block 362 and diamond 363 is repeated until the record is transferred correctly, e.g., the calculated hash sum does equal the received hash sum.

If instead the time stamp for machine Y is later than the time stamp for machine X, machine Y at block 364 copies and replaces the unique id record (along with its time stamp, hash sum, and corresponding actual data) to machine X. Next, at diamond 365, machine X checks to see whether the record (along with its time stamp, hash sum, and corresponding actual data) transferred correctly to machine X. In one embodiment, machine X calculates its own hash sum and compares it to the hash sum received from machine Y (as discussed in connection with method 220 of FIG. 4B) to determine if the record transferred correctly. If not, e.g., the calculated hash sum does not equal the received hash sum, machine X sends a corresponding message to machine Y, and machine Y repeats the step at block 364. The loop at block 364 and diamond 365 is repeated until the record is transferred correctly, e.g., the calculated hash sum does equal the received hash sum.

After the verifying step at diamonds 363 or 365, method 350 causes machine X at diamond 366 to look for the next unique id in the sequence. If a next unique id in the sequence exists, method 350 repeats the sequence from block 354 to diamond 366. Eventually, machine X runs out of new data to check for synchronization with machine Y as indicated by negative response to diamond 366, at which time method 350 ends at oval 368. Again, in FIG. 5A, any two machines 12a and 12b for example both get the opportunity to the be the X machine and the Y machine of FIG. 5B.

Figure 5C:
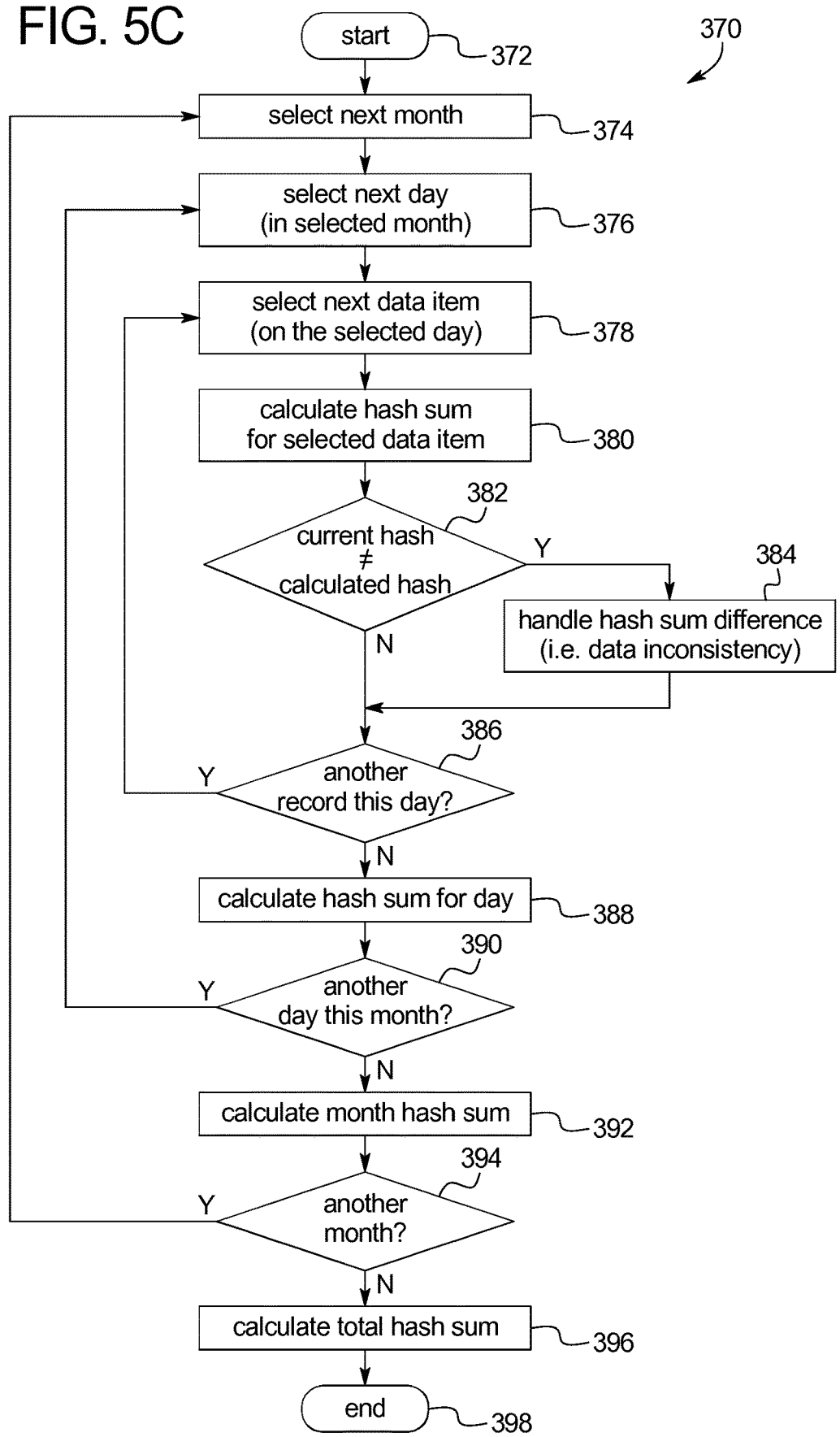
FIG. 5C is a logic flow diagram illustrating one embodiment for a machine or sensing equipment of the distributed database system of the present disclosure to verify its data.

Referring now to FIG. 5C, method 370 illustrates one embodiment for verifying that data stored in any of machines 12 is correct and not corrupt. In an embodiment, each machine 12 of distributed database system 10 is programmed to perform method 370 routinely on some periodic basis, e.g., upon each power up, upon being awakened from a sleep mode, hourly, daily, at the beginning or end of each shift, at the beginning or end of each treatment, weekly, monthly, or at some other desired period.

At oval 372, method 370 begins. At block 374, the particular machine 12a to 12j selects a next month's worth of data to verify. At block 376, the particular machine 12a to 12j selects a next day's worth of data within the selected month to verify. At block 378, the particular machine 12a to 12j selects the next data (or array of data) to verify for the selected day of the selected month. At block 380, the particular machine 12a to 12j calculates a new hash sum for the selected data (or array of data). At diamond 382, the particular machine 12a to 12j compares the current (previously calculated) hash sum for the data (or array of data) with the newly calculated hash sum for the data (or array of data).

If the answer to diamond 382 is yes, and the current (previously calculated) hash sum for the data (or array of data) does not equal the newly calculated hash sum for the data (or array of data), then the particular machine 12a to 12j takes corrective action, as indicated at block 384, in response to determining that the particular data (or array of data) has become corrupted. In an embodiment, corrective action at block 384 includes deleting the corrupted data (or data array) associated with the current (previously calculated) hash sum. The deleted data will be replaced automatically via the synchronization procedures discussed next in connection with FIGS. 6A and 6B (which use the subroutines of FIGS. 4A, 5A and 5B). In an alternative embodiment, corrective action at block 384 includes automatically invoking a synchronization procedure discussed next in connection with FIGS. 6A and 6B upon learning of corrupt data at diamond 386. The machine 12 can for example be programmed to synchronize with the next downstream machine 12 of the distributed database system 10, e.g., machine 12a having corrupted data synchronizes with machine 12b, machine 12b with machine 12c, machine 12j with machine 12a, and so on.

After corrective action block 384, or if the answer to diamond 382 is no, and the current (previously calculated) hash sum for the data (or array of data) does equal the newly calculated hash sum for the data (or array of data), then the particular machine 12a to 12j at diamond 386 queries whether there is another data record for the particular day to verify. If so, the loop between block 378 and diamond 386 is repeated until there is no new data record for the particular day to verify, upon which the particular machine 12a to 12j at block 388 calculates a new hash sum for the selected day (which corresponds to block 208 of FIG. 4A).

After block 388, the particular machine 12a to 12j at diamond 390 queries whether there is another day in the selected month having data to verify. If so, the loop between block 376 and diamond 390 is repeated until there is no new day within the selected month having a data record to verify, at which time the particular machine 12a to 12j at block 392 calculates a new month hash sum for the selected month (which corresponds to block 210 of FIG. 4A).

After block 392, the particular machine 12a to 12j at diamond 394 queries whether there is another month in the total hash sum having data to verify. If so, the loop between block 374 and diamond 394 is repeated until there is no new month within the total hash sum calculation having a data record to verify, at which time the particular machine 12a to 12j at block 396 calculates a new total hash sum (which corresponds to block 212 of FIG. 4A).

After block 396, method 370 ends as at oval 398. Method 370 of FIG. 5C as illustrated verifies data, on a machine by machine basis, for all months, days and records of the total hash sum for that machine. Not only is all data for the machine 12 verified, new total hash sums, e.g., total day hash sum, total month hash sum, and total hash sum are also verified. In this manner, if the corrupted data has been sent to any other machine 12 of distributed database system 10, it will be corrected in the other machine 12 of system 10 via the synchronization procedures discussed next.

The methods of FIGS. 4A, 5A and 5B are building blocks used for the "push-pull" method 400 of FIG. 6A and the "pull" method of FIG. 6B. Referring now to FIG. 6A, method 400 illustrates one methodology that can be implemented on distributed database system 10 for updating machines 12, so that each machine 12 includes all data for each patient within a clinic 130 receiving a particular type of treatment. Method 400 is an example of a data synchronization mode in which machines 12 "push" new data to other machines 12 of distributed database system 10 between diamond 404 and block 408, and "pull" data from each other between block 410 and diamond 414. Method 400 can allow each machine 12 to take turns pushing data to the other machines 12 of system 10 or to an aggregate of machines 12. Method 400 is for one machine of distributed database system 10. Method 400 would therefore be repeated for each machine 12, or aggregate of machines 12, of system 10.

At oval 402, method 400 begins. It is possible to begin data updating at a time when machines 12 have finished delivering treatments. For instance, if clinic or dialysis center 130 provides treatment between 8:00 AM and 7:00 PM, method 400 can begin automatically later in the evening, e.g., 11:00 PM during or after machines 12 have all been cleaned and prepared for the next treatment shift or next day. Machines 12 of distributed database system 10 may all be hibernating or in a sleep mode at 11:00 PM. If needed, method 400 wakes each machine 12 of distributed database system 10 from a sleep mode to perform method 400.

Diamond 404 and blocks 406 and 408 for a given machine 12 (or aggregate of machines 12) generate and send any new data for that machine to all other machines of distributed database system 10. At diamond 404, machine 12 determines whether it has any new data to send. If the answer is yes, there is new data to send, machine 12 at block 406 performs the tag data or metadata of method 200 of FIG. 4A. Machine 12 at block 408 then pushes the tagged new data (including unique id record, time stamp, hash sum, and corresponding actual data) to each other machine 12 of distributed database system 10 that is currently online and capable of receiving the tagged new data according to method 220 of FIG. 4B in one embodiment.

It should be appreciated that steps 404 to 408 can be performed (i) so as to push to the other machines each tagged new data individually as it is created, or alternatively (ii) to collect all new data for that day or time period and send the collected data as one packet to all other online machines 12 of distributed database system 10. When there is no other new data for machine 12, as determined at diamond 404, method 400 moves to a synchronization ("pull") portion to synchronize with any other machine 12 that may have been offline.

The synchronization portion of method 400 is performed at blocks 410, 412 and diamond 414. The same machine 12 (or aggregate of machines 12) at steps 404 to 408 now at block 410 picks another machine 12 of distributed database system 10 to see if any data needs to be synchronized. In an embodiment, machine 12 picks the next addressed machine, and then the following machine and so on. For example, machine 12a first picks machine 12b, then machine 12c, and so on. The last addressed machine picks the first addressed machine, and then proceeds in order, e.g., machine 12j picks machine 12a, then machine 12b, and so on.

At block 412, the given machine 12 and its chosen machine 12 perform the synchronization sequence illustrated in FIGS. 5A and 5B. The synchronization sequence supplies any missing data between the given machine 12 and its chosen machine 12 due, for example, to one or both of the machines having been offline from system 10 at a time in which the other machine generated new data. At diamond 414, the chosen machine 12 checks to see if there is another machine 12 of distributed database system 10 with which to synchronize. If so, steps 410 to 414 are performed again, and so on until chosen machine 12 has synchronized with each other online machine of distributed database system 10, after which method 400 ends as illustrated at oval 416.

Method 400 is then performed for each machine 12 (or aggregate of machines 12) of distributed database system 10. In this manner, each machine 12 (i) sends its new data to each of the other machines 12 of system 10 and (ii) is synched with each other machine of system 10. Thus when a patient arrives at clinic or dialysis center 130, e.g., the next day, the patient can be brought to any machine 12a to 12j of distributed database system 10. That machine will have that patient's full treatment history. The machine will also have the patient's preferred treatment settings, or perhaps multiple sets or ranges of preferred settings for the patient, streamlining treatment setup for the nurse or clinician, and optimizing treatment results for the patient.

An alternative "push" embodiment (not illustrated) is a hub and spoke type of push. One of the machines acts as a hub machine, while other machines of distributed database system 10 act as spokes. Here, one or more machine of the cluster, e.g., machine 12a receives the data from all other machines 12b to 12j. Machines 12b to 12j can each send their respective data according to a sequence requested by hub machine 12a. Hub machine 12a will then store the data from machines 12b to 12j in the order in which the data is sent to hub machine 12a. Once hub machine 12a is fully updated with data from all the other machines of distributed database system 10, hub machine 12a sends out the totalled data, including machine 12a's data, to all other machines 12b to 12j in the distributed database system 10, which can again be according to a sequence requested by hub machine 12a. Again, in the end, each of the, e.g., ten machines, should have the same data from every other machine of the distributed database system.

Referring now to FIG. 6B, method 430 illustrates another methodology that can be implemented on distributed database system 10 for updating machines 12, so that each machine 12 includes all data for each patient within a clinic 130, or for each patient receiving a particular type of treatment within clinic 130. Method 430 is an example of a data synchronization mode in which machines 12 "pull" new data from other machines 12 of distributed database system 10 or an aggregate of machines as has been described herein. Method 430 is for one machine of distributed database system 10 or an aggregate of machines 12 as has been described herein. Method 400 would therefore be repeated for each machine 12, or aggregate of machines 12, of the system.

At oval 432, method 430 begins. Steps 434 and 436 are very similar to steps 404 and steps 406 of method 400 of FIG. 6A. Step 436 is performed in accordance with method 200 of FIG. 4A. Here, however, machine 12 data tags all of its new data at steps 434 and 436 at once but does not send it to the other machines 12 of distributed database system 10. Step 408 of method 400 is missing in method 430. The new data is instead pulled from machine 12 via the synchronization process of steps 438 to 442, which are performed the same as steps 410 to 414 described above for method 400 of FIG. 6A.

The same machine 12 or aggregate of machines 12 at steps 434 and 436 now at block 438 picks another machine 12 of distributed database system 10 to see if any data needs to be synchronized. In an embodiment, machine 12 picks the next addressed machine, and then the following machine and so on, as described above. At block 440, the given machine 12 and its chosen machine 12 perform the synchronization sequence illustrated in FIGS. 5A and 5B. The synchronization sequence supplies any missing data between the given machine 12 and its chosen machine 12 due, for example, to one or both of the machines having been offline from system 10 at a time in which the other machine generated new data. At diamond 442, the given machine 12 checks to see if there is another machine 12 of distributed database system 10 with which to synchronize. If so, steps 438 to 442 are performed again, and so on until the given machine 12 has synchronized with each other online machine of distributed database system 10, after which method 430 ends as illustrated at oval 444.

Method 430 is then performed for each machine 12, or aggregate of machines 12, of distributed database system 10. Thus each machine 12 (i) pulls data from and (ii) is synchronized with each other machine 12 of distributed database system 10. Afterwards, when a patient arrives at clinic or dialysis center 130, e.g., the next day, the patient can be brought to any machine 12a to 12j of distributed database system 10. That machine will have that patient's full treatment history and preferred settings.

Figure 7A:
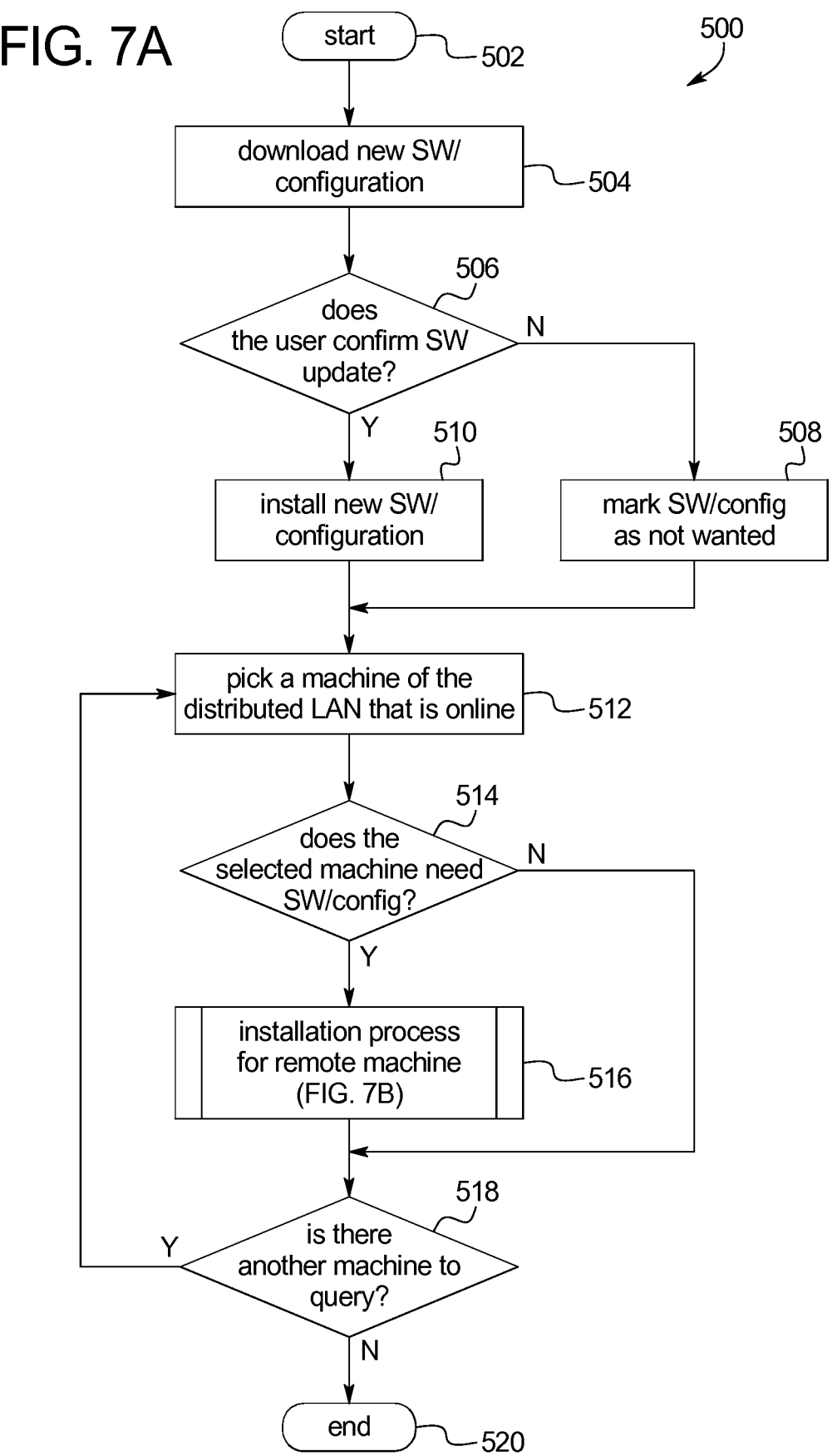
FIG. 7A is a logic flow diagram illustrating one embodiment of a "push" mode for updating operating software on different machines of a distributed database system and method of the present disclosure.

Referring now to FIG. 7A, method 500 illustrates one embodiment for providing software updates to the machines of distributed database system 10. Software updates in an embodiment are operating software updates, which can be main control software, user interface software, safety software, software for peripheral items (such as a water system or remote sensors), software configurations (user/clinic preferences for how machines 12 should work in their particular settings), and any combination thereof. At oval 502, method 500 begins. At block 504, new software is downloaded to one of machines 12 of distributed database system 10. The software can be downloaded via a USB drive at the machine or over LAN 150 via any of the LAN embodiments described above. The software can be provided from server computer 180 in one embodiment.

In an embodiment, new software is downloaded automatically to the lowest numbered or earliest lettered addressed machine 12 of distributed database system 10 that is online. For example, server computer 180 via LAN 150 would download the software to machine 12a if it is online, or to machine 12b if it is online and machine 12a is offline. Alternatively, an installer can bring a USB drive manually to any machine 12a to 12j of distributed database system 10 for initial installation. That machine would then select the next addressed online machine, e.g., if the installer brings the USB drive to machine 12g, machine 12g would thereafter deliver the new software to machine 12h, and so on.

At diamond 506, the user (nurse or clinician) at the initial machine 12 decides whether or not to confirm the installation of the new operating software. The user does not have to accept the new software for whatever reason, for example, the user likes the current software. If the user decides not to accept the new software at block 508, the new software is not installed at the initial machine 12. The new software nevertheless resides in the memory of the initial machine 12, with a flag that it has been rejected and the date rejected. A system administrator can be notified that the initial machine 12 rejected the software. The rejected software can be accepted at a later date, and may be configured to periodically prompt the user to see if they are ready for the software update.

If the user decides to accept the new software at diamond 506, the new software or configuration of software at block 510 is installed at the initial machine 12. In either case, after block 508 (download but no install) or block 510 (download and install), the initial machine picks a new machine 12 of distributed database system 10 and asks the new machine using LAN 150 whether the new machine needs the new software, as indicated at diamond 514. Again, the new machine can be the next addressed machine, e.g., machine 12a selects machine 12b, which selects machine 12c, and so on. Machine 12j (of FIG. 1A) would select first machine 12a.

If the answer is to the question of diamond 514 is no, e.g., the new machine 12 already has the new operating software, then initial machine 12 at diamond 518 looks to see if another machine of distributed database system 10. If the answer to the question of diamond 514 is yes, e.g., the new machine 12 needs the new operating software, then the installation subroutine at block 516 is performed. The installation subroutine is discussed in detail below in connection with FIG. 7B.

When the installation subroutine at block 516 is completed, or if the new machine does not need the new operating software as determined at diamond 514, method 500 at diamond 518 determines whether there is another machine of distributed database system 10 to query. If so, then the loop created between block 512 to diamond 518 is repeated until there is no other machine of distributed database system 10 to query. Method 500 then ends at oval 520.

Figure 7B:
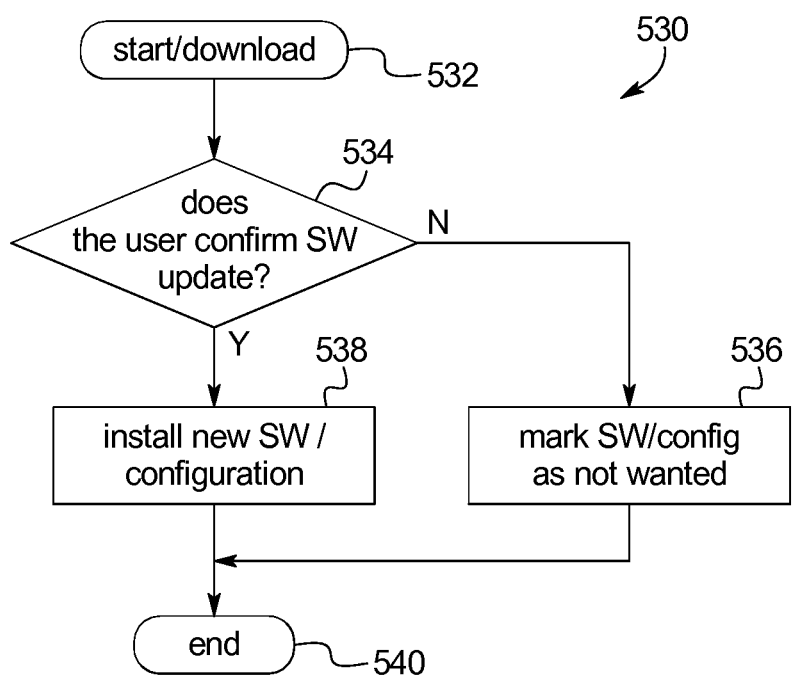
FIG. 7B is a logic flow diagram illustrating one embodiment of a subroutine for a user to confirm installation of a new software update, the subroutine used with the logic flow diagram of FIG. 7A.

Referring now to FIG. 7B, method 530 illustrates one embodiment for the installation subroutine 516 of method 500 of FIG. 7A. At oval 532, method 530 begins by downloading the new operating software to the new machine (e.g., from the initial machine to the first new machine, from the first new machine to the second new machine, from the second new machine to the third new machine, and so on). At diamond 534, the user (nurse or clinician) at the new machine 12 decides whether or not to confirm the installation of the new operating software. The user again does not have to accept the new software for whatever reason, for example, the user likes the current software. If the user decides not to accept the new software at block 536, the new software is not installed at the new machine 12. The new software nevertheless resides in the memory of new machine 12, with a flag that it has been rejected and the date rejected. A system administrator can be notified that the new machine 12 has rejected the new operating software. The rejected software can be accepted at the new machine at a later date, and may be configured to periodically prompt the user to see if they are ready for the software update.

If the user at the new machine decides to accept the new software at diamond 534, the new software or configuration of software at block 538 is installed at the new machine 12. In either case, after block 536 (download but no install) or block 538 (download and install), the initialization subroutine of method 530 ends, as indicated at oval 540. Upon returning to the loop created between block 512 and diamond 518, the new machine becomes the first new machine, which at block 512 picks a second new machine. If the second new machine needs the new operating software, as determined at diamond 514, then in subroutine 516, the first new machine downloads the new software to the second new machine. If the second new machine does not need the new operating software, as determined at diamond 514, then a third new machine can be picked at block 512. If the third new machine needs the new operating software, as determined at diamond 514, then in one embodiment of subroutine 516, the first new machine downloads the new software to the third new machine. In an alternative embodiment, because the second new machine already had the new operating software, as determined at diamond 514, the second new machine can download the new software to the third new machine.

FIGS. 7A and 7B illustrate an example of where new operating software is pushed out to each online machine 12 of distributed database system 10 sequentially, machine to machine. In an alternative embodiment, system 10 instead pushes the new operating software out to each online machine 12 at once, in parallel. A user (nurse or clinician) at each machine then proceeds through steps 506 and 508 or 510 (or steps 534 and 536 or 538) in the manner described above.

Figure 7C:
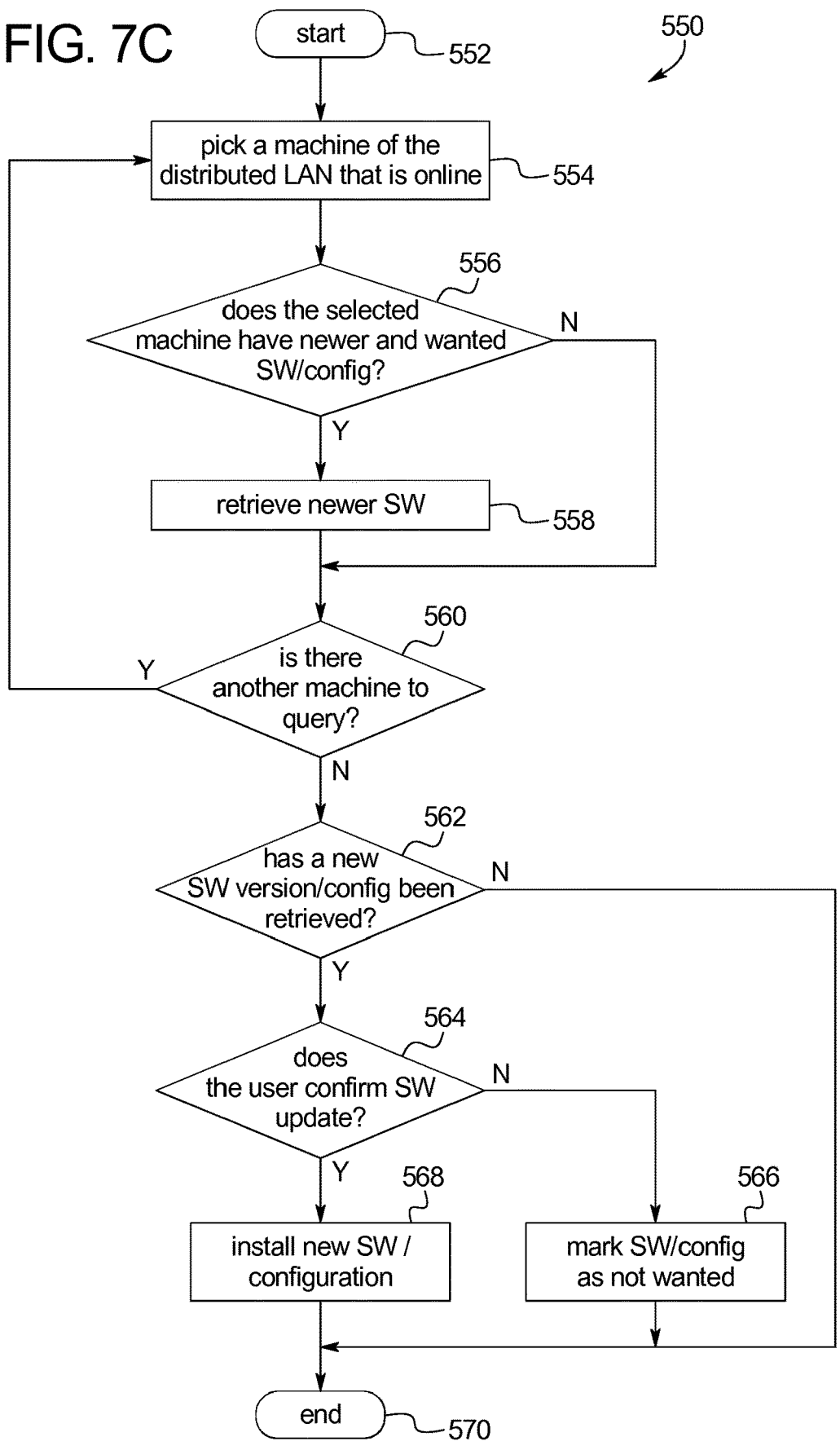
FIG. 7C is a logic flow diagram illustrating another embodiment of a "pull" mode for updating operating software on different machines of a distributed database system and method of the present disclosure.

Method 550 of FIG. 7C, on the other hand, is performed in one embodiment when a machine 12 that has been offline comes back online. Here, the newly online machine 12 looks to the other machines 12 of distributed database system 10 to see if there is any new operating software to "pull". If so, the newly online machine is given the option of choosing to install such software. Method 550 begins at oval 552. At block 554, the newly online machine 12 picks a machine of distributed database system 10 to query. As before, machine 12 can pick the next addressed machine, e.g., machine 12d first picks machine 12e, then machine 12f, then machine 12g, and so on.

At diamond 556, the newly online machine 12 compares its operating software version(s) with that of the selected machine to see if the selected machine has a higher version (s). If no, the newly online machine 12 checks if there is another machine to query at diamond 560. If yes, the newly online machine 12 retrieves (but does not install) the newer software from the selected machine, as indicated at block 558. After block 558, or if the answer to diamond 556 is no, the newly online machine checks to see if there is another machine to query at diamond 560. If there is another machine 12 to query, newly online machine 12 at diamond 556 compares its latest software version (its original software version or a newer version retrieved at block 558) to that of the second selected machine to see if the second selected machine 12 has an even later version. If so, the newly online machine retrieves the even later version and purges the earlier version. The loop at block 554 to diamond 560 is repeated until the newly online machine 12 queries all other online machines 12 of distributed database system 10, as determined at diamond 560.

At diamond 562, if the newly online machine 12 has retrieved no new software, then method 550 ends at oval 570. At diamond 562, if the newly online machine 12 has retrieved new software, then the user (e.g., nurse of clinician) at diamond 564 is prompted to either confirm or deny the installation of the newly retrieved software. The user again does not have to accept the new software for whatever reason, for example, the user likes the current software. If the user decides not to accept the new software at block 566, the new software is not installed at the new machine 12. The new software nevertheless resides in the memory of new machine 12, with a flag that it has been rejected and the date rejected. A system administrator can be notified that the new machine 12 has rejected the software. The rejected software can be accepted at the newly online machine 12 at a later date, and may be configured to periodically prompt the user if they are ready for the software update.

If the user at the newly online machine decides to accept the new software at diamond 564, the new software or configuration of software at block 568 is installed at new machine 12. Method 550 then ends at oval 570. It should be appreciated that the software receiving machine 12 of method 550 does not have to be a newly online machine and can instead be each machine 12 of distributed database system 10, which prompts itself periodically to see if there is any newer operating software to download for approval.

Also, in any software update scenario discussed herein, while it may be advantageous or needed under a regulatory control to require user acceptance or confirmation, e.g., at diamond 564 above, such acceptance or confirmation in an alternative embodiment is not required.

Figure 8A:
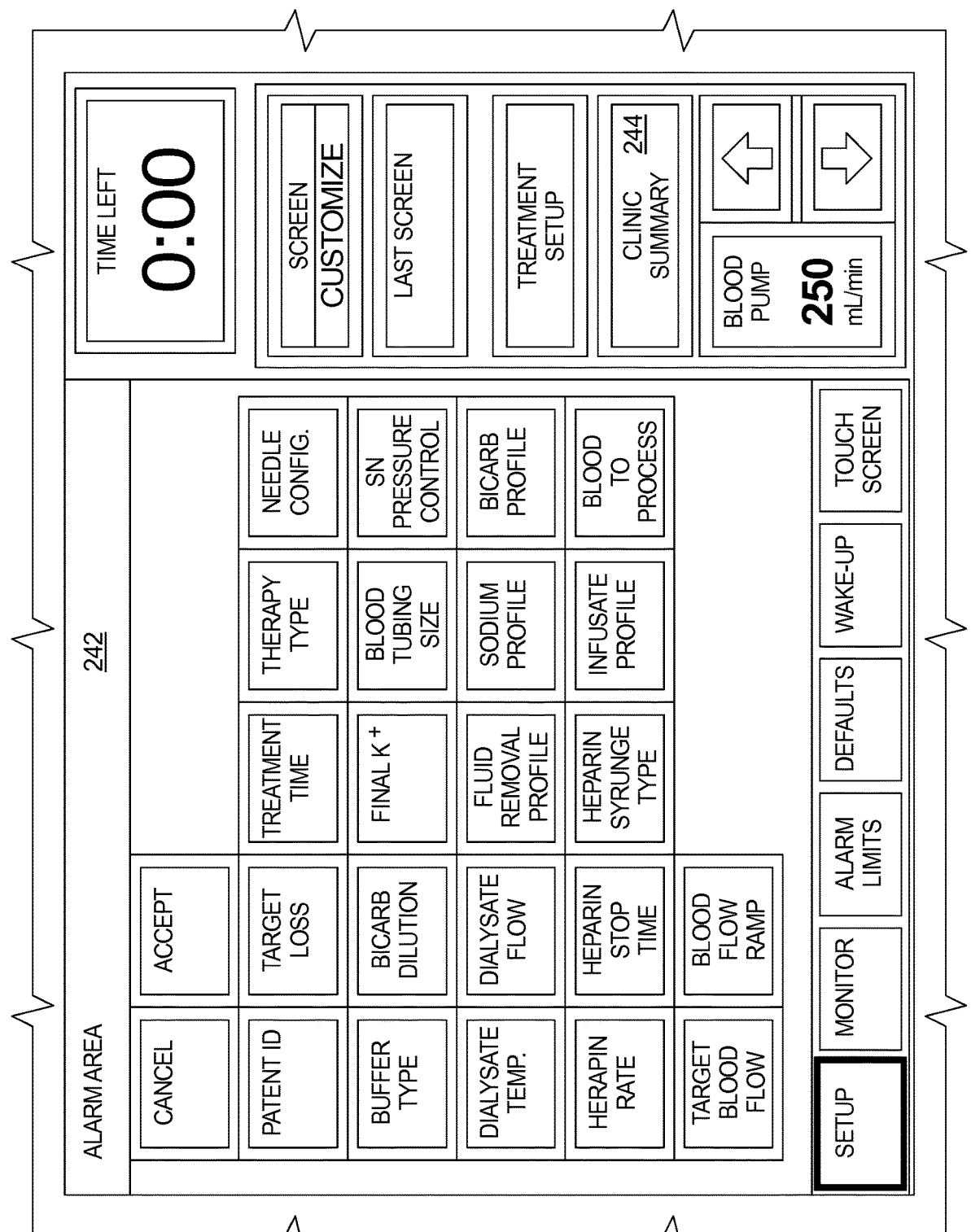
FIG. 8A is a screenshot from a machine of a distributed database system of the present disclosure, illustrating one embodiment of a "clinic summary" button that when pressed takes the user to a clinic summary screen.
Figure 8B:
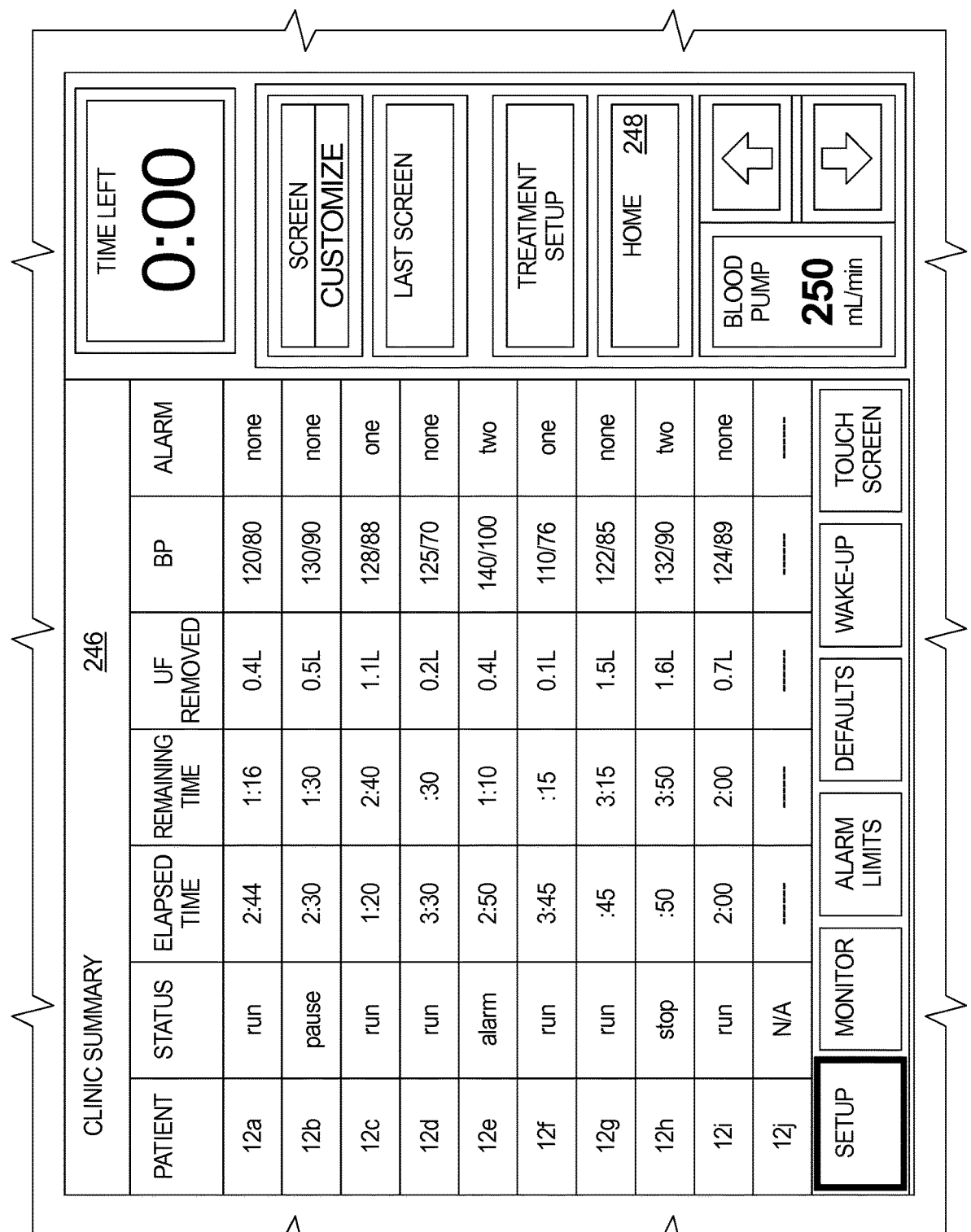
FIG. 8B is a screenshot from a machine of a distributed database system of the present disclosure, illustrating one embodiment of a clinic summary screen.

Referring now to FIGS. 8A and 8B, real time data is not limited to alarms and can include other information pertinent to a nurse or clinician. FIG. 8A illustrates an example home screen 242 of user interface 14 (see additionally FIG. 10), which can be displayed on user interface 14 (see FIG. 10 below) of machine 12. In the illustrated embodiment, home screen 242 is for a hemodialysis ("HD") machine or hemodiafiltration ("HDF") machine and displays prescription parameters and treatment output data pertinent to HD or HDF. Home screen 242 also displays a "clinic summary" button 244 that when pressed takes the nurse or clinician to a clinic summary screen 246 of user interface 14 illustrated in FIG. 8B. Clinic summary screen 246 includes a "home" button 248, which when pressed takes the nurse or clinician back to home screen 242. The nurse or clinician can therefore very quickly via two presses of a button, from any machine 12 of a distributed database system 10, see a summary of real time progress of all machines 12 of the distributed database, and then return to the user interface display of the machine 12 at which the nurse or clinician is attending.

Clinician's summary screen 246 of FIG. 8B can display any desired information. In the illustrated embodiment, clinician's summary screen 246 displays for each machine 12a to 12j information regarding current state of the machine (e.g., running, paused, under alarm condition, or not in use), elapsed treatment time, time of treatment remaining, amount of UF collected, patient blood pressure, and alarm history. Other treatment output data could also be displayed. Moreover, one or more of the displayed data can also be a button that the nurse or clinician can press to gather more information regarding the selected data.

As discussed above with FIG. 3, it is contemplated that the real time data of clinician's summary screen 246 be shared on a different distributed database than the prescription parameters and treatment output data shared for normal treatment. To do so, timer and sensor outputs can be sent to different memories 18 (see FIG. 10 below) or areas of the same memory 18. For example, the patient's blood pressure reading could be sent to a first memory 18 or area of memory 18 for normal treatment sharing on a first distributed database, and to a second memory 18 or area of memory 18 for real time streaming on a second distributed database. In this way, a malfunction or corruption of data of the second, real time streaming distributed database does not affect normal operation of machines 12 or the sharing of normal prescription parameters or treatment output data.

Besides the clinician's summary screen, it is contemplated to provide one or more additional summary screens, such as a treatment summary screen, patient summary screen, planning summary screen, inventory or stock keeping summary screen, and staffing summary screen. Each of the screens can be called up via a home screen button as illustrated above in FIG. 8A. Where multiple summary screens are contemplated, home screen 242 can provide a "summary" button, which when pressed calls up a series of summary buttons, one each for "clinic summary", "treatment summary", "patient summary", "planning summary", "stock keeping summary" and "staffing summary". Pressing any of the summary buttons takes the user to the appropriate screen, which is outfitted with a return "home" button 248.

In general, a "treatment summary" button when pressed leads to a screen providing information for a single patient and a single treatment. The "patient summary" button when pressed leads to a screen providing information for a single patient over multiple treatments. The "planning summary" button when pressed leads to a screen that can be a daily, weekly, and/or monthly calendar showing planned dates for one or more patient's treatments. The "stock keeping summary" button when pressed can lead to a stock summary screen listing supply names, how many of each supply is in stock and how many of each supply is on back order. The "staffing summary" button when pressed can lead to a "staffing summary" screen listing all clinicians, nurses and doctors associated with the clinic, and which ones are currently at the clinic, their shift times, their technical specialties, and the like. Thus a nurse or clinician at any machine 12 of distributed database 10 can reach any of the above summaries of information, quickly and easily.

In one embodiment, a user such as a nurse or clinician must enter identification and receive authorization to review any information of the distributed databases of the present disclosure, including the summary information just described. For example, machine 12 between home screen 242 and clinician summary screen 246 can present an authentication screen (not illustrated), which requests the user's user identification and password. Machine 12 is programmed such that only after entry of an authorized username and password can the requesting nurse or clinician see clinician summary screen. It is likewise contemplated for the retrieval of any and all distributed database data, e.g., any medically related data as described above, to be username and password protected. Remote computers 170 and PCD's 175 may be subject to even more stringent authentication, such as being required to manually enter a Completely Automated Public Turing test to tell Computers and Humans Apart ("CAPTCHA") code generated at the remote computers 170 and PCD's 175. Strong authentication can also be required at machine 12 and/or at the remote computers 170 and PCD's 175, e.g., in the form of an authentication (e.g., login) based on something the requesting person knows (e.g., a password) and something the requesting person possesses (e.g., an authorization card). Moreover, it is contemplated that system 10 keep track, e.g., at one or more of machine 12, server 180, and/or personal computer 170, of a log of which people, e.g., of a clinic 130a to 130c, have accessed which data on distributed database system 10. In this manner, a listing of which individuals have accessed any particular data of system 10 can be generated.

Referring now to FIG. 9, method 250 illustrates one possible life cycle for machine prescription parameter or treatment output data ("data") acquired by distributed database system 10 via one of the methods discussed above in connection with FIGS. 4A to 6B. At oval 252, method 250 begins. At block 254, new data is acquired at one of machines 12a to 12j of distributed database system 10. At block 256, the newly acquired data is inputted into a moving average trend. For example, the data could be an amount of ultrafiltration ("UF") removed from the patient, which is entered as the latest or most recent UF entry in an ongoing or moving UF trend. The trend can include multiple trends, such as an actual data trend, a three-day moving average trend, a seven-day moving average trend, etc. System 10 of the present disclosure takes advantage of the compiling of data for multiple patients and multiple treatments, where trending and the calculation of averages are two examples.

At block 258, the new data and the updated trend are synchronized to the other machines 12 of distributed database system 10. The synchronization can be performed according to any of the methods discussed above in connection with the methods of FIGS. 4A to 6B. The nurse or clinician can then see the data in tabulated and trended form at each of machines 12a to 12j of distributed database system 10.

An optional step is provided at block 260 (shown in phantom line). The data here is backed up to one or more server computer 180 or personal computer 170. As discussed herein, distributed database system 10 can operate without any server computers. For example the backup at block 260 could instead be to an external memory storage device, e.g., a USB or flash drive. However, if the clinic 130 wants to connect a server computer 180 or personal computers 170 to LAN 150, distributed database system 10 provides the opportunity to do so, e.g., for use as backup memory devices.

At block 262, the data is purged from distributed database system 10 after a time period, e.g., six months or one year, as desired, and as dictated by the memory capacity of machines 12a to 12j of distributed database system 10. In this manner, the memory capacity of machines 12a to 12j does not have to be unduly large. However, even though the individual data points are purged, the data can still be maintained on machines 12 of LAN 150 as part of one or more trend. Also, the data can be backed-up and retrieved from memory storage at a later time if needed.

It should be noted that the memory or hard disk needed for most machines 12 will at the time of filing this application have a typical capacity from about thirty-two to sixty-four gigabytes. In many cases, the size of memory for machines 12 is selected based upon cost, where a larger memory can actually be less expensive than a smaller memory because the larger memory is in greater supply and/or is more readily available. If a typical treatment requires about two to four kilobytes of data, machines 12 can store on the order of million treatments. Assuming that a given machine 12 performs 5,000 treatments during its lifetime of, for example, ten years, that machine 12 can store treatment data for 200 machines. Nevertheless, data may need to be purged from system 10 reasons other than storage capacity. For example, medical regulations of certain jurisdictions can require that information about a patient be removed when the patient no longer has a relationship with a clinic. Thus at block 262, the designated time period may be due to a regulatory requirement rather than a memory storage issue.

To delete or remove data, system 10 in one embodiment deletes the data but leaves metadata attached to the data. System 10 uses the left-behind metadata to make sure the deleted data is not restored when a machine 12 that has been disconnected from the distributed database at the time of deletion is later reconnected. System 10 provides a hand shaking process to ensure that all deleted data is deleted from all machines 12 in the distributed database. Here, deleted data is given a new header or identifier and a trail for how and when the data has been deleted. The header and trail are propagated out to the other machines 12 according to any of methods discussed in connection with FIGS. 4A to 6B, so that the other machines can see that there is new "deleted" data and update their data in the same position with deleted data. It is further contemplated to provide an array in the header to track whether all machines 12 have deleted the data or not. Additional headers can be built to ensure that after all machines 12 have received the deleted data message, the data is actually deleted, freeing the cells in memory 18 (FIG. 10) to be used for new data.

At oval 264, method 250 ends.

FIGS. 10 and 11 provide detail on hemodialysis, hemodiafiltration and hemofiltration versions of machine 12. Much of the structure of renal failure therapy machines 12, e.g., user interface, processing, memory, pumps, is likewise provided on other types of machines. It is contemplated, however, that any of the input parameters and treatment output data associated with the renal failure therapy machines 12 discussed next be included in the updates data just described.

FIG. 10 illustrates that renal failure therapy machine 12 incudes a user interface 14, which allows a nurse or other operator to interact with renal failure therapy machine 12. User interface 14 can have a monitor screen operable with a touch screen overlay, electromechanical buttons, e.g., membrane switches, or a combination of both. User interface 14 is in electrical communication with at least one processor 16 and at least one memory 18. As discussed above, at least one memory 18 can have a capacity of thirty-two to sixty-four gigabytes. At least one processor 16 can have a standard processing speed known to those at the time of filing, e.g., two gigahertz. Processor 16 and memory 18 also electronically interact with, and where appropriate, control the pumps, valves and sensors described herein, e.g., those of dialysate circuit 30. At least one processor 16 and at least one memory 18 are referred to collectively herein as a logic implementer 20.

Dialysate circuit 30 includes a purified water inlet line 32, an acid ("A") concentrate line 34 and a bicarbonate ("B") concentrate line 36. Purified water inlet line 32 receives purified water from a purified water device or source 22. The water may be purified using any one or more process, such as, reverse osmosis, carbon filtering, ultraviolet radiation, electrodeionization ("EDI"), and/or ultrafiltering.

An A concentrate pump 38, such as a peristaltic or piston pump, pumps A concentrate from an A concentrate source 24 into purified water inlet line 32 via A concentrate line 34. Conductivity cell 40 measures the conductive effect of the A concentrate on the purified water, sends a signal to logic implementer 20, which uses the signal to properly proportion the A concentrate by controlling A concentrate pump 38. The A conductivity signal is temperature compensated via a reading from temperature sensor 42.

A B concentrate pump 44, such as a peristaltic or piston pump, pumps B concentrate from a B concentrate source 26 into purified water inlet line 32 via B concentrate line 36. Conductivity cell 46 measures the conductive effect of the B concentrate on the purified water/A concentrate mixture, sends a signal to logic implementer 20, which uses the signal to properly proportion the B concentrate by controlling B concentrate pump 44. The B conductivity signal is also temperature compensated via a reading from temperature sensor 48.

A heating tank 50 operates with a heater 52 controlled by logic implementer 20 to heat purified water for treatment to body temperature, e.g., 37° C. Heating the water in tank 50 will also degas the water. For ease of illustration, a separate degassing chamber and pump are not illustrated but may be provided to aid expansion tank 50 in removing air from the purified water. The fluid exiting conductivity cell 46 is therefore freshly prepared dialysate, properly degassed and heated, and suitable for sending to dialyzer 102 for treatment. A fresh dialysate pump 54, such as a gear pump, delivers the fresh dialysate to dialyzer 102. Logic implementer 20 controls fresh dialysate pump 54 to deliver fresh dialysate to dialyzer 102 at a specified flowrate as described in more detail below.

A drain line 56 via a used dialysate pump 58 returns used dialysate from the dialyzer to a drain 60. Logic implementer 20 controls used dialysate pump 58 to pull used dialysate from dialyzer 102 at a specified flowrate. An air separator 62 separates air from the used dialysate in drain line 56. A pressure sensor 64 senses the pressure of used dialysis fluid within drain line 56 and sends a corresponding pressure signal to logic implementer 20.

Conductivity cell 66 measures the conductivity of used fluid flowing through drain line 56 and sends a signal to logic implementer 20. The conductivity signal of cell 66 is also temperature compensated via a reading from temperature sensor 68. A blood leak detector 70, such as an optical detector, looks for the presence of blood in drain line, e.g., to detect if a dialyzer membrane has a tear or leak. A heat exchanger 72 recoups heat from the used dialysate exiting dialysate circuit 30 to drain 60, preheating the purified water traveling towards heater 52 to conserve energy.

A fluid bypass line 74 allows fresh dialysate to flow from fresh dialysate line 76 to drain line 56 without contacting dialyzer 102. A fresh dialysate tube 78 extends from renal failure therapy machine 12 and carries fresh dialysate from fresh dialysate line 76 to dialyzer 102. A used dialysate tube 80 also extends from renal failure therapy machine 12 and carries used dialysate from dialyzer 102 to drain line 56.

Fresh dialysate line also includes a conductivity sensor or cell 82 that senses the conductivity of fresh dialysate leaving a UF system control unit 90 and sends a corresponding signal to logic implementer 20. The conductivity signal of cell 82 is likewise temperature compensated via a reading from temperature sensor 84.

An ultrafilter 86 further purifies the fresh dialysate before being delivered via dialysate line 76 and fresh dialysate tube 78 to dialyzer 102. As discussed in more detail below, one or more ultrafilter 88 can be used to purify the fresh dialysate to the point where it can be used as substitution fluid to perform pre- or post-dilution hemofiltration or hemodiafiltration.

UF system 90 monitors the flowrate of fresh dialysate flowing to dialyzer 102 (and/or as substitution fluid flowing directly to the blood set (FIG. 11)) and used fluid flowing from the dialyzer. UF system 90 includes fresh and used flow sensors Q1$c$ and Q2$c$, respectively, which send signals to logic implementer 20 indicative of the fresh and used dialysate flowrate, respectively. Logic implementer 20 uses the signals to set used dialysate pump 58 to pump faster than fresh dialysate pump 54 by a predetermined amount to remove a prescribed amount of ultrafiltration ("UF") from the patient over the course of treatment. Fresh and used flow sensors Q1$p$ and Q2$p$ are redundant sensors that ensure UF system 90 is functioning properly.

Renal failure therapy machine 12 uses plural valves 92 (collectively referring to valves 92*a* to 92*l*) under the control of logic implementer 20 to selectively control a prescribed treatment. In particular, valve 92*a* selectively opens and closes bypass line 68, e.g., to allow disinfection fluid to flow from fresh dialysate line 76 to drain line 56. Valve 92*b* selectively opens and closes fresh dialysate line 76. Valve 92*c* selectively opens and closes used dialysate or drain line 56. Valve 92*d* selectively opens and closes drain line 56 to drain 60. Valve 92*e* selectively opens and closes purified water line 32 to purified water source 22. Valves 92*f* and 92*g* control A and B concentrate flow, respectively. Valves 92*h* to 92*k* operate with UF system 90.

FIG. 10 further illustrates a substitution line 96 (located inside the housing of machine) extending off of fresh dialysate line 76. Substitution line 96 is fluidly coupled to a substitution tube 98 of a blood set 100 discussed below. A valve 92l under control of logic implementer 20 selectively opens and closes substitution line 96. A substitution pump 94 under control of logic implementer 20 selectively pumps fresh dialysate from ultrafilter 86 through a second ultrafilter 88 to produce replacement or substitution fluid, which is delivered via substitution line 96 (within machine housing) and a substitution tube 98 (external to machine housing) to arterial blood line 106 and/or venous blood line 108 instead of fresh dialysate via line 76 (hemofiltration ("HF")) or in addition to fresh dialysate via line 76 (for hemodiafiltration ("HDF")).

FIG. 11 illustrates one embodiment of a blood set 100 that can be used with renal failure therapy machine 12. Blood circuit or set 100 includes a dialyzer 102 having many hollow fiber semi-permeable membranes 104, which separate dialyzer 102 into a blood compartment and a dialysate compartment. The dialysate compartment during treatment is placed in fluid communication with a distal end of fresh dialysate tube 78 and a distal end of used dialysate tube 80. For HF and HDF, a separate substitution tube, in addition to fresh dialysate tube 78, is placed during treatment in fluid communication with one or both of arterial line 106 and venous line 108. In HDF, dialysate also flows through dialysate tube 78 to dialyzer 102, while for HF, dialysate flow through tube 78 is blocked.

Arterial line 106 includes a pressure pod 110, while venous line 108 includes a pressure pod 112. Pressure pods 110 and 112 operate with blood pressure sensors (not illustrated) mounted on the machine housing, which send arterial and venous pressure signals, respectively, to logic implementer 20 (FIG. 10). Venous line 108 includes an air separation chamber or venous drip chamber 114, which removes air from the patient's blood before the blood is returned to patient 116.

Arterial line 106 of blood circuit or set 100 is operated on by blood pump 120, which is under the control of logic implementer 20 to pump blood at a desired flowrate. Renal failure therapy machine 12 also provides multiple blood side electronic devices that send signals to and/or receive commands from logic implementer 20. For example, logic implementer 20 commands pinch clamps 122a and 122b to selectively open or close arterial line 106 and venous line 108, respectively. A blood volume sensor 124 monitors how the patient's hematocrit changes over the course of treatment. Blood volume sensor 124 is in one embodiment placed in arterial line 106 upstream of the blood pump. Air detector 126 looks for air in the venous blood line. Substitution tube 98 as illustrated can be coupled to arterial line 106 for pre-dilution HF or HDF and/or venous line 108 for post-dilution HF or HDF.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A medical device system comprising:
    a plurality of medical devices each including a memory, the plurality of medical devices communicatively coupled such that the memories collectively form a distributed database; and
    a logic implementer associated with each medical device, wherein each logic implementer is programmed to automatically access the distributed database, so that each medical device of the system periodically (i) delivers at least one selected from the group consisting of prescription input parameters and treatment output data to at least one of the other medical devices and (ii) retrieves at least one selected from the group consisting of prescription input parameters and treatment output data from at least one of the other medical devices,
    wherein the medical devices are configured to communicate directly with at least one of the other medical devices via the distributed database,
    wherein at least one of the logic implementers is configured to periodically push at least one of the prescription input parameters or the treatment output data to at least one of the other medical devices without instruction from a centralized server,
    wherein at least one of the logic implementers is configured to periodically pull at least one of the prescription input parameters or the treatment output data from at least one of the other medical devices without instruction from a centralized server by
        after receiving a request to perform a renal failure treatment for a patient in a logic implementer of a selected one of the medical devices, compare, via the logic implementer a most recent time stamp of prescription input parameters related to the patient at the selected medical device to time stamps of prescription input parameters related to the same patient at the other medical devices,
        determine a most recent time stamp in one of the other medical devices,
        select the prescription input parameters corresponding to the most recent time stamp from the other medical device, and
        locally store in the selected medical device the prescription input parameters corresponding to the most recent time stamp to perform the renal failure treatment for the patient, and
    wherein the medical devices are renal failure therapy machines.

2. The medical device system of claim 1, wherein the medical devices are in data communication with each other via a local area network used in connection with the distributed database.

3. The medical device system according to claim 1, wherein each of the medical devices is updated to store the same at least one of the prescription input parameters or the treatment output data for each of a plurality of patients.

4. The medical device system according to claim 1, wherein the medical devices and the distributed database do not interact with a centralized server.

5. The medical device system according to claim 1, wherein the medical devices are provided by first and second manufacturers, and which includes an interface enabling the medical devices of the first and second manufacturers to communicate with one another.

6. The medical device system according to claim 1, wherein at least one selected from the group consisting of the (i) prescription input parameters and (ii) treatment output data is shared via the distributed database along with at least one other selected from the group consisting of (iii) technical input data, (iv) technical output data, and (v) administrative data.

7. The medical device system according to claim 1, wherein the distributed database also shares information from at least one medical equipment selected from the group consisting of: a weight scale, a blood pressure measurement device, a glucose sensor, a physiological sensor, an electrocardiogram device, water treatment equipment, a bed scale, an access disconnection device, a bioimpedance measurement device, a pH sensor, lab testing equipment, a blood sample analyzer, and an access flow measurement device.

8. The medical device system according to claim 1, wherein the distributed database is a first distributed database, and which includes a second distributed database that shares information from at least one medical equipment selected from the group consisting of: a weight scale, a blood pressure measurement device, a glucose sensor, a physiological sensor, an electrocardiogram device, water treatment equipment, a bed scale, an access disconnection device, a bioimpedance measurement device, a pH sensor, lab testing equipment, a blood sample analyzer, and an access flow measurement device.

9. The medical device system according to claim 1, wherein periodically delivering and retrieving prescription input parameters or treatment output data includes doing so in at least one selected from the group consisting of: real time, a matter of seconds, a matter of minutes, hourly, daily, weekly, monthly, at an end of a treatment, at an end of a treatment day, and at an end of a treatment shift.

10. The medical device system according to claim 1, which is configured to share operating software between the medical devices via the distributed database.

11. The medical device system according to claim 1, wherein the distributed database is a first distributed database, and which includes a second distributed database, wherein the logic implementer of at least one of the plurality of the medical devices is programmed to access the second distributed database.

12. The medical device system according to claim 11, wherein one of the distributed databases is a real time data database.

13. The medical device system according to claim 11, wherein one of the distributed databases is an administrative data database.

14. The medical device system according to claim 1, wherein each medical device is programmed to periodically verify the at least one of the prescription input parameters or the treatment output data.

15. The medical device system according to claim 14, wherein verification is performed via a comparison of hash sums.

16. The medical device system according to claim 1, wherein the plurality of medical devices are programmed to periodically synchronize the at least one of the prescription input parameters or the treatment output data.

17. The medical device system according to claim 16, wherein synchronization is performed via a comparison of at least one selected from the group consisting of record identifications, hash sums, and time stamps.

18. The medical device system according to claim 1, wherein at least one of the medical devices is programmed to display at least one summary screen showing at least one of the prescription input parameters and treatment output data for different medical devices of the system.

19. A medical device distributed database system comprising:
a plurality of medical devices each including a memory, the medical devices including renal failure therapy machines for preforming renal failure treatments;
a first distributed database automatically sharing first data generated or used by a plurality of first medical devices amongst the plurality of medical devices, the memories of the plurality of first medical devices collectively forming the first distributed database; and
a second distributed database automatically sharing (i) second data generated or used by the plurality of first medical devices amongst the plurality of medical devices, (ii) second data generated or used by a plurality of second medical devices amongst the plurality of medical devices, or (iii) second data generated or used by medical equipment, at least one of (a) the memories of the plurality of first medical devices or (b) the memories of the plurality of second medical devices collectively forming the second distributed database,
wherein at least one medical device of the plurality of first medical devices is configured to periodically push the first data including at least one of prescription input parameters or treatment output data to at least one of the other medical devices of the plurality of first medical devices without instruction from a centralized server, and
wherein at least one medical device of the plurality of first medical devices is configured to periodically pull the first data including at least one of the prescription input parameters or the treatment output data from at least one of the other medical devices of the plurality of first medical devices without instruction from a centralized server by
after receiving a request to perform a renal failure treatment for a patient in the at least one medical device, compare a most recent time stamp of prescription input parameters related to the patient at the at least one medical device to time stamps of prescription input parameters related to the same patient at the plurality of first medical devices,
determine a most recent time stamp in one of the plurality of first medical devices,
select the prescription input parameters corresponding to the most recent time stamp from the determined first medical device, and
locally store in the at least one medical device the prescription input parameters corresponding to the most recent time stamp to perform the renal failure treatment for the patient.

20. The medical device distributed database system according to claim 19, wherein one of the plurality of first medical devices and one of the second medical devices are configured to provide treatment to a same patient.

21. The medical device distributed database system according to claim 19, wherein one of the first medical devices and one of the medical equipment are configured to provide treatment to a same patient.

22. The medical device distributed database system according to claim 19, wherein the first medical devices are for providing treatment to a first group of patients and the second medical devices are for providing treatment to a second group of patients.

23. A medical device comprising:
at least one medical fluid pump;
a plurality of other medical devices including respective memories that form a distributed database, the plurality of other medical devices each including a renal failure therapy machine; and
a logic implementer including a memory and operating the at least one medical fluid pump so as to accept a pump input parameter and generate pump output data, the logic implementer programmed to (i) automatically share at least one selected from the group consisting of the pump input parameter and the pump output data with the plurality of other medical devices via the distributed database, and (ii) automatically receive at least one selected from the group consisting of a pump input parameter and pump output data from the plurality of other medical devices via the distributed database, wherein the memory of the logic implementer is configured to be communicatively coupled with the memories of the other medical devices to form the distributed database, such that the logic implementer is able to communicate directly with at least one of the other medical devices via the distributed database, wherein the logic implementer is configured to periodically push at least one of the pump input parameter or the pump output data to at least one of the other medical devices without instruction from a centralized server, and wherein the logic implementer is configured to periodically pull at least one of the prescription input parameters or the treatment output data from at least one of the other medical devices without instruction from a centralized server by
after receiving a request to perform a renal failure treatment for a patient in the logic implementer of the at least one medical fluid pump, compare, via the logic implementer a most recent time stamp of pump input parameters related to the patient at the at least one medical fluid pump to time stamps of pump input parameters related to the same patient at the plurality of other medical devices,
determine a most recent time stamp in one of the other medical devices,
select the pump input parameters corresponding to the most recent time stamp from the other medical device, and
locally store, in the at least one medical fluid pump, the pump input parameters corresponding to the most recent time stamp to perform the renal failure treatment for the patient.

24. The medical device of claim 23, wherein the logic implementer is programmed to synchronize at least one of the pump input parameter or the pump output data with the other medical devices via the distributed database.

25. The medical device of claim 24, wherein the logic implementer is programmed to compare a first corresponding hash sum thereof with a second corresponding hash sum of one of the other medical devices to synchronize at least one of the pump input parameter or the pump output data with that other medical device.

26. The medical device according to claim 23, wherein the logic implementer is programmed to send a hash sum for at least one of the pump input parameter or the pump output data to one of the other medical devices for comparison at the other medical device with a corresponding hash sum of the other medical device.

27. The medical device according to claim 23, wherein the logic implementer is programmed to verify at least one of the pump input parameter or the pump output data.

28. The medical device according to claim 27, wherein the verification includes comparing a newly calculated hash sum with a previously established hash sum for at least one of the pump input parameter or the pump output data.

29. The medical device according to claim 23, wherein the logic implementer is programmed to share at least one of the pump input parameter or the pump output data with at least one selected from the group consisting of a personal communication device, a personal computer, a server computer, and medical equipment via the distributed database.

30. The medical device according to claim 23, wherein the logic implementer is programmed to receive data from at least one selected from the group consisting of a personal communication device, a personal computer, a server computer, and medical equipment via the distributed database.

31. The medical device system according to claim 1, wherein each of the medical devices is configured to:
store a first hash sum based on at least one of previous prescription input parameters or previous treatment output data;
calculate a second hash sum based on at least one of the prescription input parameters or the treatment output data;
generate an error indicative of corrupted data when the first hash sum is different from the second hash sum; and
perform a synchronization procedure with at least one other medical device of the distributed database to replace the at least one of the prescription input parameters or the treatment output data with at least one of second prescription input parameters or second treatment output data.

32. The medical device system according to claim 1, further comprising a weight scale configured to weigh each patient prior to and after treatment by one of the plurality of medical devices,
wherein the distributed database is configured to support connectivity to the weight scale, and
wherein the distributed database is configured for:
sending a patient weight to each renal failure therapy machine of the system when each renal failure therapy machine is configured to maintain a record of patient weight; or
sending the patient weight to the renal failure therapy machine on which a patient is being treated that day and then sending the patient weight later, after treatment from the renal failure therapy machine, to each renal failure therapy machine of the system; or
storing the patient weight on a data storage device that is taken to the renal failure therapy machine on which a patient is being treated that day and then sending the patient weight later, after treatment from the renal failure therapy machine, to each renal failure therapy machine of the system.

* * * * *